(12) United States Patent
Hamadani

(10) Patent No.: US 11,634,706 B2
(45) Date of Patent: Apr. 25, 2023

(54) SINGLE-MOLECULE PHENOTYPE ANALYSIS

(71) Applicant: THE REGENTS OF THE UNIVERSITY OF CALIFORNIA, Oakland, CA (US)

(72) Inventor: Kambiz Hamadani, San Marcos, CA (US)

(73) Assignee: The Trustees of the California State University, Long Beach, CA (US)

( * ) Notice: Subject to any disclaimer, the term of this patent is extended or adjusted under 35 U.S.C. 154(b) by 1143 days.

(21) Appl. No.: 15/512,091

(22) PCT Filed: Sep. 15, 2015

(86) PCT No.: PCT/US2015/050272
§ 371 (c)(1),
(2) Date: Mar. 17, 2017

(87) PCT Pub. No.: WO2016/044328
PCT Pub. Date: Mar. 24, 2016

(65) Prior Publication Data
US 2017/0247686 A1 Aug. 31, 2017

Related U.S. Application Data

(60) Provisional application No. 62/052,175, filed on Sep. 18, 2014.

(51) Int. Cl.
| | |
|---|---|
| *C07K 1/13* | (2006.01) |
| *C12N 15/10* | (2006.01) |
| *C40B 40/08* | (2006.01) |
| *C40B 40/10* | (2006.01) |
| *C12Q 1/6874* | (2018.01) |

(52) U.S. Cl.
CPC ............ *C12N 15/1062* (2013.01); *C07K 1/13* (2013.01); *C12N 15/102* (2013.01); *C12N 15/1065* (2013.01); *C12Q 1/6874* (2013.01); *C40B 40/08* (2013.01); *C40B 40/10* (2013.01)

(58) Field of Classification Search
None
See application file for complete search history.

(56) References Cited

U.S. PATENT DOCUMENTS

| | | |
|---|---|---|
| 10,858,698 B2 | 12/2020 | Church et al. |
| 2009/0018029 A1 | 1/2009 | Miao et al. |
| 2010/0093024 A1 | 4/2010 | Goerke et al. |
| 2013/0295019 A1 | 11/2013 | Wu et al. |

FOREIGN PATENT DOCUMENTS

| | | |
|---|---|---|
| EP | 2060584 | 5/2009 |
| WO | WO2005007886 | 1/2005 |
| WO | WO2013130917 | 9/2013 |
| WO | WO2013136095 | 9/2013 |
| WO | WO2014075296 | 5/2014 |

OTHER PUBLICATIONS

Best (Biochemistry 48:6571-84) (Year: 2009).*
Murakami et al (Nature Methods 3:257-9) (Year: 2006).*
Milles et al (JACS 134:5187-95) (Year: 2012).*
Milles et al (JACS 134:5187-95 supporting information) (Year: 2012).*
"Correlative Single-Molecule FRET and DNA-Paint Imaging", NANO Letters, Jun. 26, 2018.
An in vitro tag-and-modify protein sample generation method for single-molecule fluorescence resonance energy transfer; J. Biol. Chem. (2017) 292(38) 15636-15648.
Frank, D. "BARCRAWL and BARTAB: software tools for the design and implementation of barcoded primers for highly multiplexed DNA sequencing" BMC Bioinformatics, Oct. 29, 2012 (Oct. 29, 2012), vol. 10, No. 362, pp. 1-13.
Schmidt-Dannert, C. "Directed Evolution of Single Proteins, Metabolic Pathways, and Viruses," Biochemistry, Nov. 6, 2001 (Nov. 6, 2001), vol. 40, No. 44, pp. 13125-13136.
Quail et al. "A tale of three next generation sequencing platforms: comparison of Ion Torrent, Pacific Biosciences and Illumina MiSeq sequencers," BMC Genomics, Jul. 24, 2012 (Jul. 24, 2012), vol. 13, No. 341, pp. 1-13.
PCT/US2015/050272, Written Opinion, dated Dec. 17, 2015.
Rodionov, Valentin O., et al.; Ligand-Accelerated Cu-Catalyzed Azide-Alkyne Cycloaddition: A Mechanistic Report; JACS Articles, Oct. 3, 2007.
Ligand-Accelerated Cu-Catalyzed Azide-Alkyne Cycloaddition: a Mechanistic Report; Valentin O. Rodionov, Stanislav Presolski, David D. Díaz, Valery V. Fokin, M.G. Finn Department of Chemistry and The Skaggs Institute of Chemical Biology The Scripps Research Institute, 10550 N. Torrey Pines Rd., La Jolla, CA 92037, USA; Supporting Information.
Analysis and Optimization of Copper-Catalyzed Azide-Alkyne Cycloaddition for Bioconjugation Vu Hong, Stanislav I. Presolski, Celia Ma, and M. G. Finn; Angew. Chem. Int. Ed. 2009, 48, 9879-9883.
Analysis and Optimization of Copper-Catalyzed Azide-Alkyne Cycloaddition for Bioconjugation; Supporting Information; Vu Hong, Stanislav I. Presolski, Celia Ma, and M. G. Finn; Angew. Chem. Int. Ed. 2009, 48, 9879-9883.
Quality control by the ribosome following peptide bond formation; Hani S. Zaher & Rachel Green; vol. 457 | Jan. 8, 2009 | doi:10.1038/nature07582.
Quality control by the ribosome following peptide bond formation, Supplementary Information; Hani S. Zaher & Rachel Green; vol. 457 | Jan. 8, 2009 | doi:10.1038/nature07582.

(Continued)

*Primary Examiner* — Christopher M Gross
(74) *Attorney, Agent, or Firm* — Sandra Thompson; Finlayson Toffer

(57) ABSTRACT

Aspects of the present disclosure include methods of producing modified polypeptides and modified polypeptide-ribosome or polypeptide-mRNA complexes, and methods of screening polynucleotide and polypeptide libraries. The present disclosure also provides polypeptide libraries useful in screening for single molecule phenotypes. Also provided are kits useful for producing polypeptides capable of being modified using methods disclosed herein.

9 Claims, 29 Drawing Sheets

Specification includes a Sequence Listing.

(56) References Cited

OTHER PUBLICATIONS

Copper-catalyzed azide-alkyne cycloaddition (CuAAC) and beyond: new reactivity of copper(I) acetylides Jason E. Hein and Valery V. Fokin; First published as an Advance Article on the web Mar. 4, 2010DOI: 10.1039/b904091a; Chem. Soc. Rev., 2010, 39, 1302-1315.

Biocompatible Copper(I) Catalysts for in Vivo Imaging of Glycans David Soriano del Amo,554 Wei Wang,† Hao Jiang,† Christen Besanceney,†Amy C. Yan,† Matthew Levy,† Yi Liu,‡ Florence L. Marlow,# and Peng Wu,†; JACS, 2010, 132 (16893-16899).

Biocompatible Copper(I) Catalysts for in Vivo Imaging of Glycans, Supplemental Information David Soriano del Amo,† Wei Wang,† Hao Jiang,† Christen Besanceney,†Amy C. Yan,† Matthew Levy,† Yi Liu,‡ Florence L. Marlow,# and Peng Wu,†; JACS, 2010, 132 (16893-16899).

Increasing the Efficacy of Bioorthogonal Click Reactions for Bioconjugation: A Comparative Study Christen Besanceney-Webler, Hao Jiang, Tianqing Zheng, Lei Feng, David Soriano del Amo, Wei Wang, Liana M. Klivansky, Florence L. Marlow, Yi Liu, and Peng Wu; Angew. Chem. Int. Ed. 2011, 50, 1-7.

Sulfated Ligands for the Copper(I)-Catalyzed Azide-Alkyne Cycloaddition Wei Wang,[a], Senglian Hong,[b] Andrew Tran,[a] Hao Jiang,[a] Rebecca Triano,[a] Yi Liu,[c] Xing Chen,[b] and Peng Wu[a]; Chem. Asian J. 2011, 6, 2796-2802.

Single-Molecule Techniques and Cell-Free Protein Synthesis: A Perfect Marriage Alexandros Katranidis, and Jörg Fitter; Anal. Chem. 2019, 91, 2570-2576.

N-Acetyllysine Transfer Ribonucleic Acid: A Biologically Active Analogue of Aminoacyl Transfer Ribonucleic Acids; Arthur E. Johnson, et al; Biochemistry, vol. 15, No. 3, 1976.

Benzimidazole and Related Ligands for Cu-Catalyzed Azide-Alkyne Cycloaddition; Valentin O. Rodionov, Stanislav I. Presolski, Sean Gardinier, Yeon-Hee Lim, and M. G. Finn; J. Am. Chem. Soc. 2007, 129, 12696-12704.

Benzimidazole and Related Ligands for Cu-Catalyzed Azide-Alkyne Cycloaddition, Supplemental Information; Valentin O. Rodionov, Stanislav I. Presolski, Sean Gardinier, Yeon-Hee Lim, and M. G. Finn; J. Am. Chem. Soc. 2007, 129, 12696-12704.

Evolution of Amber Suppressor tRNAs for Efficient Bacterial Production of Unnatural Amino Acid-Containing Proteins Jiantao Guo+, Charles E. Melançon III+, Hyun Soo Lee, Dan Groff, and Peter G. Schultz; Angew Chem Int Ed Engl. 2009 ; 48(48): 9148-9151. doi:10.1002/anie.200904035.

Polyspecific pyrrolysyl-tRNA synthetases from directed evolution; Li-Tao Guoa,1, Yane-Shih Wanga,1, Akiyoshi Nakamuraa,b,1, Daniel Eilera,1, Jennifer M. Kavrana, Margaret Wongc, Laura L. Kiesslingd, Thomas A. Steitza,b,e, Patrick O'Donoghuef,g,2, and Dieter Sölla,b,2; www.pnas.org/cgi/doi/10.1073/pnas.1419737111.

Genomically Recoded Organisms Expand Biological Functions Marc J. Lajoie et al.Science 342, 357 (2013);DOI: 10.1126/science. 1241459.

An orthogonal ribosome-tRNA pair via engineering of the peptidyl transferase center; Naihiro Terasaka, et al.; Nature Chemical Biology I vol. 10 I Jul. 2014 I www.nature.com/naturechemicalbiology.

Multiplex single-molecule interaction profiling of DNA barcoded proteins; Liangcai Gu1, Chao Li2, John Aach1, David E. Hill1,3, Marc Vidal1,3, and George M. Church1,2; Nature. Nov. 27, 2014; 515(7528): 554-557. doi:10.1038/nature13761.

Optimized orthogonal translation of unnatural amino acids enables spontaneous protein double-labelling and FRET; Kaihang Wang, et al.; Nature Chemistry, vol. 6, May 2014 (pp. 393-403).

Optimized orthogonal translation of unnatural amino acids enables spontaneous protein double-labelling and FRET, Supplemental Information; Kaihang Wang, et al.; Nature Chemistry, vol. 6, May 2014 (pp. 393-403).

Optimized Plasmid Systems for the Incorporation of Multiple Different Unnatural Amino Acids by Evolved Orthogonal Ribosomes; Christoph Lammers, Liljan E. Hahn, and Heinz Neumann[a]; ChemBioChem 2014, 15, 1800-1804.

\* cited by examiner

| sub-component mix | | nM | ug | Units of Activity |
|---|---|---|---|---|
| Factor mix | IF1 | 2738 | 1.45 | |
| | IF2 | 401 | 2 | |
| | IF3 | 1508 | 1.55 | |
| | EF-G | 255 | 1 | |
| | EF-Tu | 1344 | 5 | |
| | EF-Ts | 1344 | 5 | |
| | RF3 | 303 | 0.91 | |
| release factor mix | RF1 | 5 | 0.01 | |
| | RF2 | 5 | 0.01 | |
| | RRF | 10 | 0.011 | |
| aaRS/other mix | AlaRS | 38 | 0.186 | 94 |
| | ArgRS | 20 | 0.067 | 130 |
| | AsnRS | 364 | 1 | |
| | AspRS | 72 | 0.478 | 130 |
| | CysRS | 23 | 0.062 | |
| | GlnRS | 8.3 | 0.027 | 63 |
| | GluRS | 101 | 0.275 | 94 |
| | GlyRS(ab) | 167 | 0.946 | 250 |
| | HisRS | 4 | 0.02 | 31 |
| | IleRS | 105 | 0.561 | 130 |
| | LeuRS | 6.9 | 0.034 | 190 |
| | LysRS | 33 | 0.19 | 190 |
| | MetRS | 24 | 0.186 | 310 |
| | PheRS(ab) | 390 | 2.47 | 63 |
| | ProRS | 18 | 0.227 | 63 |
| | SerRS | 32 | 0.256 | 94 |
| | ThrRS | 53 | 0.204 | 63 |
| | TrpRS | 12.2 | 0.047 | 31 |
| | TyrRS | 1.8 | 0.009 | 31 |
| | ValRS | 7.4 | 0.04 | 156 |
| | MTF | 571 | 1 | |
| | AK | 116 | 0.15 | |
| | CK | 93 | 0.2 | |
| | NDK | 62 | 0.055 | |
| | PPiase | 69 | 0.068 | |
| seperately added | T7 RNA pol | 100 | 0.5 | |
| | Ribosomes | 1200 | 150 | |
| | e.coli tRNA | 90000 | 112 | |
| | FormylDonor | 78000 | 2 | |
| Amino Acid mix | | | Units | |
| | AA's | 0.3 | mM | |
| | Creatine Phosphate | 20 | mM | |
| | ATP | 2 | mM | |
| | GTP | 2 | mM | |
| | CTP | 1 | mM | |
| | UTP | 1 | mM | |
| Other components | | | | |
| | HEPES+Tris | 50 | mM | |
| | $K^+ + NH_4^+$ | 175 | mM | |
| | spermidine | 0.5 | mM | |
| | Putrescine | 8 | mM | |
| | $Mg^{2+}$ | 8 | mM | |
| | $ZnSO_4$ | 2 | uM | |
| | Tween-20 | 0.05 | % (v/v) | |
| | BME | 3 | mM | |

FIG. 5

| peak | residues | Predicted | | | Observed | | |
|---|---|---|---|---|---|---|---|
| | | +1 ion | +2 ion m/z | +3 ion | +1 ion | +2 ion m/z | +3 ion |
| 1 | 97-119 | 2391.30 | 1196.15 | 797.77 | | 1196.12 | 797.73 |
| 2 | 20-35 | 1780.90 | 890.95 | 594.30 | | 890.93 | 594.29 |
| 3 | 171-185 | 1717.90 | 859.45 | 573.30 | | 859.43 | 573.29 |
| 4 | 84-95 | 1375.75 | 688.38 | 459.25 | | 688.36 | 459.26 |
| 5 | 66-76 | 1247.63 | 624.32 | 416.54 | | 624.30 | |
| 6 | 126-135 | 1116.56 | 558.78 | 372.85 | | 558.77 | |
| 7 | 138-145 | 1078.50 | 539.75 | 360.17 | 1078.39 | 539.74 | |
| 8 | 163-170 | 1051.54 | 526.27 | 351.18 | | 526.26 | |
| 9+formyl | 1-8 | 1006.54 | 503.77 | 336.18 | | 503.73 | |
| 10 | 155-162 | 929.41 | 465.21 | 310.47 | | 465.20 | |
| 11 | 53-60 | 846.46 | 423.73 | 282.82 | 846.47 | 423.68 | |
| 12 | 36-43 | 787.42 | 394.21 | 263.14 | | | |
| 13 | 149-154 | 736.42 | 368.71 | 246.14 | | | |
| 14 | 9-14 | 702.37 | 351.69 | 234.79 | 702.36 | | |
| 15 | 120-124 | 629.40 | 315.20 | 210.47 | | | |
| 16 | 61-65 | 607.26 | 304.13 | 203.09 | | | |
| 17 | 44-48 | 591.29 | 296.15 | 197.76 | | | |

T4L construct used:
MGIFELLRIDEGLRLKIYKDTEGYYTIGIGHLLTKSPSLNAAKSELDKAIGRNTNGVITKMEA
EKLFNQDVDAAVRGILRNAKLKPVYDSLDAVRRAALINLVFQLGETGVAGFTNSLRLLQQ
KRVVDEAAVNLAKSRWYNQTPNRAKRVITTFRTGTWCAYKNLEFLPYRQFSTPVWISQA
QGIRAGPQ

FIG. 6

TABLE 4: General overview of the constructs used in this study

| Protein | backbone variants cp=circular permutants | Labelling sites | Side-chain variants | truncation points Used to study N-terminal fragments | C-term fusions Used to explore effects of a C-terminal helix (EK-peptide) on an N-terminal protein | C-term extensions Used to bring the nascent polypeptide out from the exit tunnel | released | Total # proteins |
|---|---|---|---|---|---|---|---|---|
| T4 Lysozyme-M -M=(M6L,M102L, M106,M120L, C54T,C97A) | wt | 1-only | wt | | | none | released | 192 |
| | | 1-38 | V75P | Δ74 | EK | secM | RNC | |
| | | 1-53 | R76P | | PEK | $(GS)_1$-secM | RNC | |
| | | 1-55 | G77A | Δ94 | GEK | $(GS)_3$-secM | RNC | |
| | | 1-61 | | Δ114 | none | $(GS)_5$-secM | RNC | |
| | | 1-159 | | Δ134 | | $(GS)_6$-secM | RNC | |
| NTD=N-terminal domain | | | | Δ154 | | $(GS)_{10}$-secM | RNC | |
| | | | | none | | $(GS)_{15}$-secM | RNC | |
| EK=highly-helical EK-peptide | cp13 (starts@12) | 12-only | wt | | EK | none | released | 75 |
| | | 12-38 | V75P | Δ74 (NTD) | PEK | secM | RNC | |
| | | 12-53 | R76P | | GEK | $(GS)_1$-secM | RNC | |
| | | 12-55 | G77A | none | none | $(GS)_5$-secM | RNC | |
| | | 12-61 | | | | $(GS)_5$-secM | RNC | |
| | | 12-159 | | | | $(GS)_6$-secM | RNC | |
| | | | | | | $(GS)_{10}$-secM | RNC | |
| | | | | | | $(GS)_{15}$-secM | RNC | |

FIG. 12A

TABLE 4: (CONT.)

| | cp81 (starts@81) | 81-only | wt | none | none | none | released | Total # proteins |
|---|---|---|---|---|---|---|---|---|
| | | 81-38 | G77A | | EK | secM | RNC | 60 |
| | | 81-53 | | | PEK | (GS)$_1$-secM | RNC | |
| | | 81-55 | | | | (GS)$_3$-secM | RNC | |
| | | 81-61 | | | | (GS)$_5$-secM | RNC | |
| | | 81-159 | | | | (GS)$_6$-secM | RNC | |
| | | | | | | (GS)$_{10}$-secM | RNC | |
| | | | | | | (GS)$_{15}$-secM | RNC | |
| Barnase | | 1-only | wt | Δ95 | none | none | released | Total # proteins |
| GCR=genetic code reprogramming | | 1-44 | | Δ100 | | secM | RNC | 32 |
| | | 1-66 | | Δ105 | | (GS)$_5$-secM | RNC | |
| | | 1-102 | | none | | (GS)$_{10}$-secM | RNC | |
| | | 44-102 (GCR) | | | | (GS)$_{15}$-secM | | |
| | | 66-102 (GCR) | | | | | | |
| Spectrin R16-R17;KH | | 1-only | wt | | EK | none | released | Total # proteins |
| KH = K1M, M15A, P60A, M132A | | 1-36 | L97A | Δ113 (R16) | PEK | (GS)$_5$-secM | RNC | 180 |
| | | 1-39 | G105A | | GEK | (GS)$_{10}$-secM | RNC | |
| | | 1-92 | | Δ135 (R16-R17a) | none | (GS)$_{15}$-secM | RNC | |
| | | 1-99 | | | | (GS)$_{20}$-secM | RNC | |
| Titin I28-M M60A, M74A | | 1-only | wt | none | none | none | released | Total # proteins |
| | | 1-70 | | | | | | 5 |
| | | 1-72 | | | | | | |
| | | 1-74 | | | | | | |
| | | 1-94 | | | | | | |
| | | | | | | | Total # proteins | 544 |

FIG. 12B

| Protein | HPG sites | Variant | C-terminal extension | PURE IVT system used | # S-E histograms | show rep smFRET hist |
|---|---|---|---|---|---|---|
| Barnase RNCs | M1 | wt | SecM | H | 2 | Y |
| Barnase RNCs | M1 | Δ105 | SecM | H | 2 | Y |
| Barnase RNCs | M1-M102 | wt | SecM | H | 7 | Y |
| Barnase RNCs | M1-M102 | wt | (GS)$_{15}$-SecM | H | 6 | Y |
| Barnase RNCs | M1-M44 | Δ95 | SecM | H | 7 | Y |
| Barnase RNCs | M1-M44 | wt | SecM | H | 7 | Y |
| Barnase RNCs | M1-M44 | wt | (GS)$_{15}$-SecM | H | 7 | Y |
| Barnase RNCs | M1-M66 | Δ95 | SecM | H | 7 | Y |
| Barnase RNCs | M1-M66 | wt | SecM | H | 7 | Y |
| Barnase RNCs | M1-M66 | wt | (GS)$_{10}$-SecM | H | 7 | Y |
| Barnase RNCs | M1 | wt | SecM | H | 2 | Y |
| Barnase RNCs | M1-M102 | wt | SecM | H | 2 | Y |
| Barnase RNCs | M1-M44 | wt | SecM | H | 2 | Y |
| Barnase RNCs | M1-M66 | wt | SecM | H | 2 | Y |
| Barnase (released) | M1 | wt | | C | 2 | Y |
| Barnase (released) | M1-M44 | wt | | C | 2 | Y |
| Barnase (released) | M1-M66 | wt | | C | 2 | Y |
| Barnase (released) | M1-M102 | wt | | C | 2 | Y |
| Spectrin R16 KH RNCs | M1 | wt | R17a-SecM | C | 2 | Y |
| Spectrin R16 KH RNCs | M1-M39 | wt | R17a-SecM | C | 2 | Y |
| Spectrin R16 KH RNCs | M1-M39 | wt | R17a-(GS)$_{15}$-SecM | C | 2 | Y |
| Spectrin R16 KH RNCs | M1-M92 | wt | R17a-SecM | C | 2 | Y |
| Spectrin R16 KH RNCs | M1 | wt | R17a-SecM | C | 1 | Y |
| Spectrin R16 KH RNCs | M1-M39 | wt | R17a-SecM | C | 2 | Y |
| Spectrin R16 KH RNCs | M1-M92 | wt | R17a-SecM | C | 1 | Y |
| Spectrin R16 KH RNCs | M1-M39 | wt | R17a-(GS)$_{15}$-SecM | C | 2 | Y |
| Spectrin R16 KH (released) | M1 | wt | R17a | C | 2 | Y |
| Spectrin R16 KH (released) | M1-M39 | wt | R17a | C | 2 | Y |
| Spectrin R16 KH (released) | M1-M92 | wt | R17a | C | 2 | Y |
| Spectrin R16 KH (released) | M1 | wt | EK peptide | C | 1 | Y |
| Spectrin R16 KH (released) | M1-M39 | wt | EK peptide | C | 2 | Y |
| Spectrin R16 KH (released) | M1-M39 | L97A | EK peptide | C | 1 | Y |
| Spectrin R16 KH (released) | M1-M39 | G105A | EK peptide | C | 1 | Y |
| Spectrin R16 KH (released) | M1-M39 | G105A | PEK peptide | C | 1 | Y |
| Spectrin R16 KH (released) | M1-M39 | wt | GEK peptide | C | 1 | Y |
| Spectrin R16 KH (released) | M1-M39 | G105A | GEK peptide | C | 1 | Y |
| Spectrin R16 KH RNCs | M1 | wt | R17a-SecM | C | 3 | Y |
| Spectrin R16 KH RNCs | M1-M36 | wt | R17a-SecM | C | 2 | Y |
| Spectrin R16 KH RNCs | M1-M39 | wt | R17a-SecM | C | 2 | Y |
| Spectrin R16 KH RNCs | M1-M92 | wt | R17a-SecM | C | 18 | Y |
| Spectrin R16 KH RNCs | M1-M99 | wt | R17a-SecM | C | 6 | Y |
| Spectrin R16 KH (released) | M1 | wt | R17a | C | 1 | Y |

FIG. 13A

| | | | | | | |
|---|---|---|---|---|---|---|
| Spectrin R16 KH (released) | M1 | wt | R17a | | C | 1 | Y |
| Spectrin R16 KH (released) | M1-M36 | wt | R17a | | C | 9 | Y |
| Spectrin R16 KH (released) | M1-M39 | wt | R17a | | C | 7 | Y |
| Spectrin R16 KH (released) | M1-M92 | wt | R17a | | C | 6 | Y |
| Spectrin R16 KH (released) | M1-M99 | wt | R17a | | C | 5 | Y |
| Spectrin R16 KH RNCs | M1 | wt | R17a-SecM | C | included in above count |
| Spectrin R16 KH RNCs | M1-M39 | wt | R17a-SecM | C | included in above count |
| Spectrin R16 KH RNCs | M1-M92 | wt | R17a-SecM | C | included in above count |
| Spectrin R16 KH (released) | M1-M39 | wt | R17a | C | included in above count |
| Spectrin R16 KH (released) | M1-M92 | wt | R17a | C | included in above count |
| Spectrin R16 KH RNCs | M1 | wt | R17a-SecM | C | 1 | Y |
| Spectrin R16 KH RNCs | M1-M39 | wt | R17a-SecM | C | 3 | Y |
| Spectrin R16 KH RNCs | M1-M92 | wt | R17a-SecM | C | 3 | Y |
| Spectrin R16 KH RNCs | M1-M39 | wt | R17a-(GS)$_{15}$-SecM | C | 3 | Y |
| Titin I28 (released) | M1 | wt | | C | 2 | Y |
| Titin I28 (released) | M1-M70 | wt | | C | 2 | Y |
| Titin I28 (released) | M1-M74 | wt | | C | 8 | Y |
| Titin I28 (released) | M1-M94 | wt | | C | 1 | Y |
| Titin I28 (released) | M1-M72 | wt | | C | 7 | Y |
| T4 Lysozyme (released) | M81-M38 | cp81 | | | 1 | N |
| T4 Lysozyme (released) | M81-M38 | cp81 | H6 | | 1 | N |
| T4 Lysozyme (released) | M81-M38 | cp81 | EK peptide-H6 | | 1 | N |
| T4 Lysozyme (released) | M81-M38 | cp81 | PEK peptide-H6 | | 1 | N |
| T4 Lysozyme (released) | M81-M38 | cp81, G77A | | | 1 | N |
| T4 Lysozyme (released) | M81-M38 | cp81, G7 | H6 | | 1 | N |
| T4 Lysozyme (released) | M81-M38 | cp81, G7 | EK peptide-H6 | | 1 | N |
| T4 Lysozyme (released) | M81-M38 | cp81, G7 | PEK peptide-H6 | | 1 | N |
| T4 Lysozyme (released) | M81-M38 | cp81 | | | 1 | N |
| T4 Lysozyme (released) | M81-M38 | cp81 | H6 | | 1 | N |
| T4 Lysozyme (released) | M81-M38 | cp81 | EK peptide-H6 | | 1 | N |
| T4 Lysozyme (released) | M81-M38 | cp81 | PEK peptide-H6 | | 1 | N |
| T4 Lysozyme (released) | M81-M38 | cp81, G77A | | | 1 | N |
| T4 Lysozyme (released) | M81-M38 | cp81, G7 | H6 | | 1 | N |
| T4 Lysozyme (released) | M81-M38 | cp81, G7 | EK peptide-H6 | | 1 | N |
| T4 Lysozyme (released) | M81-M38 | cp81, G7 | PEK peptide-H6 | | 1 | N |
| T4 Lysozyme NTD RNCs | M12 | wt-opt | CTD Δ94-GS-SecM | C | 2 | Y |
| T4 Lysozyme NTD RNCs | M12-M53 | wt-opt | EK peptide-GS-SecM | C | 2 | Y |
| T4 Lysozyme NTD RNCs | M12-M55 | wt-opt | EK peptide-GS-SecM | C | 2 | Y |
| T4 Lysozyme NTD RNCs | M12-M53 | wt-opt | PEK peptide-GS-SecM | C | 2 | Y |
| T4 Lysozyme NTD RNCs | M12-M55 | wt-opt | PEK peptide-GS-SecM | C | 2 | Y |
| T4 Lysozyme NTD RNCs | M12-M53 | wt-opt | EK peptide-(GS)$_3$-SecM | C | 1 | Y |
| T4 Lysozyme NTD RNCs | M12-M55 | wt-opt | EK peptide-(GS)$_3$-SecM | C | 1 | Y |
| T4 Lysozyme NTD RNCs | M12-M53 | wt-opt | PEK peptide-(GS)$_3$-SecM | C | 1 | Y |
| T4 Lysozyme NTD RNCs | M12-M55 | wt-opt | PEK peptide-(GS)$_3$-SecM | C | 1 | Y |
| T4 Lysozyme NTD RNCs | M12 | wt-opt | CTD 94-GS-SecM | C | 1 | Y |
| T4 Lysozyme NTD RNCs | M12-M53 | wt-opt | EK peptide-GS$_6$-SecM | C | 1 | Y |
| T4 Lysozyme NTD RNCs | M12-M55 | wt-opt | EK peptide-GS$_6$-SecM | C | 1 | Y |
| T4 Lysozyme NTD RNCs | M12-M53 | wt-opt | PEK peptide-GS$_6$-SecM | C | 1 | Y |

FIG. 13B

| T4 Lysozyme NTD RNCs | M12-M53 | wt-opt | PEK peptide-(GS)₆-SecM | C | 1 | Y |
|---|---|---|---|---|---|---|
| T4 Lysozyme NTD RNCs | M12-M55 | wt-opt | PEK peptide-(GS)₆-SecM | C | 1 | Y |
| T4 Lysozyme NTD RNCs | M12 | wt-opt | CTD Δ94-GS-SecM | C | 2 | Y |
| T4 Lysozyme NTD RNCs | M12-M53 | wt-opt | EK peptide-(GS)₆-SecM | C | 2 | Y |
| T4 Lysozyme NTD RNCs | M12-M55 | wt-opt | EK peptide-(GS)₆-SecM | C | 2 | Y |
| T4 Lysozyme NTD RNCs | M12-M53 | wt-opt | PEK peptide-(GS)₆-SecM | C | 2 | Y |
| T4 Lysozyme NTD RNCs | M12-M55 | wt-opt | PEK peptide-(GS)₆-SecM | C | 2 | Y |
| T4 Lysozyme NTD RNCs | M12 | wt-opt | CTD Δ94-SecM | H | 1 | Y |
| T4 Lysozyme NTD RNCs | M12-M53 | wt-opt | CTD Δ94-SecM | H | 1 | Y |
| T4 Lysozyme NTD RNCs | M12-M55 | wt-opt | CTD Δ94-SecM | H | 1 | Y |
| T4 Lysozyme NTD RNCs | M12-M53 | wt-opt | P-CTD Δ94-SecM | H | 1 | Y |
| T4 Lysozyme NTD RNCs | M12-M53 | wt-opt | PG-CTD Δ94-SecM | H | 1 | Y |
| T4 Lysozyme NTD RNCs | M12-M55 | wt-opt | PG-CTD Δ94-SecM | H | 1 | Y |
| T4 Lysozyme NTD RNCs | M12 | wt-opt | CTD Δ94-SecM | H | 1 | Y |
| T4 Lysozyme NTD RNCs | M12 | wt | CTD Δ94-SecM | H | 1 | Y |
| T4 Lysozyme NTD RNCs | M12-M53 | wt | CTD Δ94-SecM | H | 1 | Y |
| T4 Lysozyme NTD RNCs | M12-M55 | wt | CTD Δ94-SecM | H | 1 | Y |
| T4 Lysozyme NTD RNCs | M12 | wt | CTD Δ94-SecM | H | 1 | Y |
| T4 Lysozyme NTD RNCs | M12 | wt | CTD Δ94-SecM | H | 1 | Y |
| T4 Lysozyme NTD RNCs | M12-M53 | wt | CTD Δ94-SecM | H | 1 | Y |
| T4 Lysozyme NTD RNCs | M12 | wt | P-CTD Δ94-SecM | H | 1 | Y |
| T4 Lysozyme NTD RNCs | M12 | wt | CTD Δ94-SecM | H | 1 | Y |
| T4 Lysozyme NTD RNCs | M12-M53 | wt | CTD Δ94-SecM | H | 1 | Y |
| T4 Lysozyme NTD RNCs | M12 | wt | P-CTD Δ94-SecM | H | 1 | Y |
| T4 Lysozyme NTD RNCs | M12 | wt | CTD Δ94-SecM | H | 1 | Y |
| T4 Lysozyme NTD RNCs | M12-M53 | wt | CTD Δ94-SecM | H | 1 | Y |
| T4 Lysozyme NTD RNCs | M12 | wt | P-CTD Δ94-SecM | H | 1 | Y |
| T4 Lysozyme NTD RNCs | M12 | wt | CTD Δ94-SecM | H | 5 | Y |
| T4 Lysozyme NTD RNCs | M12-M53 | wt | CTD Δ94-SecM | H | 5 | Y |
| T4 Lysozyme NTD RNCs | M12 | wt | P-CTD Δ94-SecM | H | 5 | Y |
| T4 Lysozyme NTD RNCs | M12-M53 | wt | P-CTD Δ94-SecM | H | 5 | Y |
| T4 Lysozyme NTD RNCs | M12 | wt | CTD Δ94-SecM | H | 1 | |
| T4 Lysozyme NTD RNCs | M12-M53 | wt | CTD Δ94-SecM | H | 1 | |
| T4 Lysozyme NTD RNCs | M12 | wt | P-CTD Δ94-SecM | H | 1 | |
| T4 Lysozyme NTD RNCs | M12-M53 | wt | P-CTD Δ94-SecM | H | 1 | |
| T4 Lysozyme NTD RNCs | M12 | wt | CTD Δ94-SecM | H | 2 | Y |
| T4 Lysozyme NTD RNCs | M12-M53 | wt | CTD Δ94-SecM | H | 0 | |
| T4 Lysozyme NTD RNCs | M12 | wt | P-CTD Δ94-SecM | H | 2 | Y |
| T4 Lysozyme NTD RNCs | M12-M53 | wt | P-CTD Δ94-SecM | H | 0 | |
| T4 Lysozyme NTD RNCs | M12 | wt | P-CTD Δ94-SecM | H | 1 | |
| T4 Lysozyme NTD RNCs | M12 | wt | CTD Δ94-SecM | H | 1 | Y |
| T4 Lysozyme NTD RNCs | M12 | wt | P-CTD Δ94-SecM | H | 1 | Y |
| T4 Lysozyme NTD RNCs | M12-M38 | wt | CTD Δ94-SecM | H | 1 | |
| T4 Lysozyme NTD RNCs | M12-M53 | wt | CTD Δ94-SecM | H | 1 | |
| T4 Lysozyme NTD RNCs | M12-M55 | wt | CTD Δ94-SecM | H | 1 | |
| T4 Lysozyme NTD RNCs | M12-M61 | wt | CTD Δ94-SecM | H | 1 | |
| T4 Lysozyme NTD RNCs | M12 | wt | CTD Δ94-SecM | H | 1 | |

FIG. 13C

| Type | Col2 | Col3 | Construct | C/H | Num | Y |
|---|---|---|---|---|---|---|
| T4 Lysozyme NTD RNCs | M12 | wt | CTD Δ94-SecM | C | 1 | |
| T4 Lysozyme NTD RNCs | M12-M38 | wt | V75P CTD Δ94-SecM | C | 1 | |
| T4 Lysozyme NTD RNCs | M12-M53 | wt | V75P CTD Δ94-SecM | C | 1 | |
| T4 Lysozyme NTD RNCs | M12-M55 | wt | V75P CTD Δ94-SecM | C | 1 | |
| T4 Lysozyme NTD RNCs | M12-M61 | wt | V75P CTD Δ94-SecM | C | 1 | |
| T4 Lysozyme NTD RNCs | M12 | wt | V75P CTD Δ94-SecM | C | 1 | |
| T4 Lysozyme NTD RNCs | M12 | wt | CTD Δ94-SecM | C | | |
| T4 Lysozyme NTD RNCs | M12 | wt | V75P CTD Δ94-SecM | H | | |
| T4 Lysozyme NTD RNCs | M12-M53 | wt | CTD Δ94-SecM | H | | |
| T4 Lysozyme NTD RNCs | M12-M53 | wt | V75P CTD Δ94-SecM | H | | |
| T4 Lysozyme NTD RNCs | M12-M53 | wt | V75P R76P CTD Δ94 | H | | |
| T4 Lysozyme NTD RNCs | M1 | wt | CTD Δ94-SecM | H | 3 | Y |
| T4 Lysozyme NTD RNCs | M1 | wt | V75P CTD Δ94-SecM | H | 3 | Y |
| T4 Lysozyme NTD RNCs | M1-M53 | wt | CTD Δ94-SecM | H | 3 | Y |
| T4 Lysozyme NTD RNCs | M1-M53 | wt | V75P CTD Δ94-SecM | H | 3 | Y |
| T4 Lysozyme NTD RNCs | M1-M53 | wt | V75P R76P CTD Δ94 | H | 3 | Y |
| T4 Lysozyme NTD RNCs | M1-M38 | | V75P CTD Δ94-SecM | H | 3 | |
| T4 Lysozyme NTD RNCs | M1-M38 | | V75P R76P CTD Δ94 | H | 3 | |
| T4 Lysozyme NTD RNCs | M1 | | V75P CTD Δ94-SecM | H | 3 | |
| T4 Lysozyme NTD RNCs | M1-M38 | | V75P R76P CTD Δ94 | H | 3 | |
| T4 Lysozyme NTD RNCs | M1-M53 | | V75P CTD Δ94-SecM | H | 7 | |
| T4 Lysozyme NTD RNCs | M1-M53 | | V75P R76P CTD Δ94 | H | 7 | |
| T4 Lysozyme RNCs | M1 | wt | SecM | H | 5 | Y |
| T4 Lysozyme RNCs | M1-M38 | wt | SecM | H | 5 | Y |
| T4 Lysozyme RNCs | M1 | D159 | (GS)$_{10}$-SecM | H | | |
| T4 Lysozyme RNCs | M1-M61 | D159 | (GS)$_{10}$-SecM | H | | |
| T4 Lysozyme RNCs | M1 | D159 | SecM | H | 1 | |
| T4 Lysozyme RNCs | M1-M61 | D159 | SecM | H | 1 | |
| T4 Lysozyme RNCs | M1-M159 | | SecM | H | 1 | |
| T4 Lysozyme RNCs | M1 | D159 | (GS)$_{15}$-SecM | H | 1 | |
| T4 Lysozyme RNCs | M1-M61 | D159 | (GS)$_{15}$-SecM | H | 1 | |
| T4 Lysozyme RNCs | M1 | D159 | SecM | H | | |
| T4 Lysozyme RNCs | M1-M38 | wt | CTD Δ94-SecM | H | 2 | Y |
| T4 Lysozyme RNCs | M1-M53 | wt | CTD Δ94-SecM | H | 2 | Y |
| T4 Lysozyme RNCs | M1-M55 | wt | CTD Δ94-SecM | H | 2 | Y |
| T4 Lysozyme RNCs | M1-M61 | wt | CTD Δ94-SecM | H | 2 | Y |
| T4 Lysozyme RNCs | M1 | wt | CTD Δ94-SecM | H | 2 | Y |
| T4 Lysozyme RNCs | M12-M38 | wt | CTD Δ94-SecM | H | 2 | Y |
| T4 Lysozyme RNCs | M12-M53 | wt | CTD Δ94-SecM | H | 2 | Y |
| T4 Lysozyme RNCs | M12-M55 | wt | CTD Δ94-SecM | H | 2 | Y |
| T4 Lysozyme RNCs | M12-M61 | wt | CTD Δ94-SecM | H | 2 | Y |
| T4 Lysozyme RNCs | M12 | wt | CTD Δ94-SecM | H | 2 | Y |
| T4 Lysozyme RNCs | M1-M38 | wt | (GS)$_{15}$-SecM | H | 13 | Y |
| T4 Lysozyme RNCs | M1 | | (GS)$_{15}$-SecM | H | 13 | Y |
| T4 Lysozyme RNCs | M1-M38 | wt | SecM | H | | |
| T4 Lysozyme RNCs | M1 | | SecM | H | | |

FIG. 13D

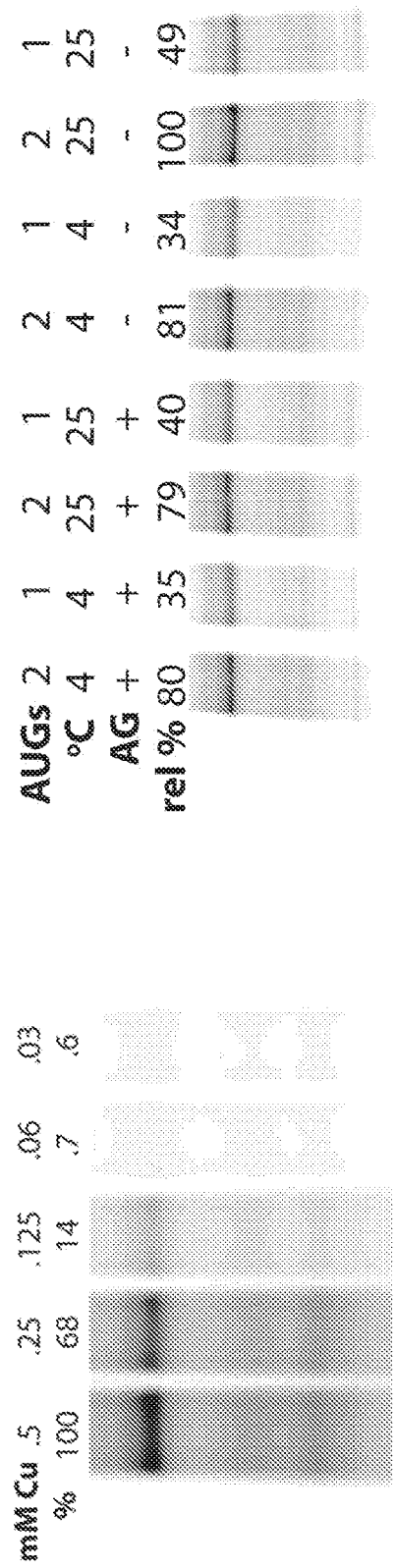
FIG. 23
FIG. 25
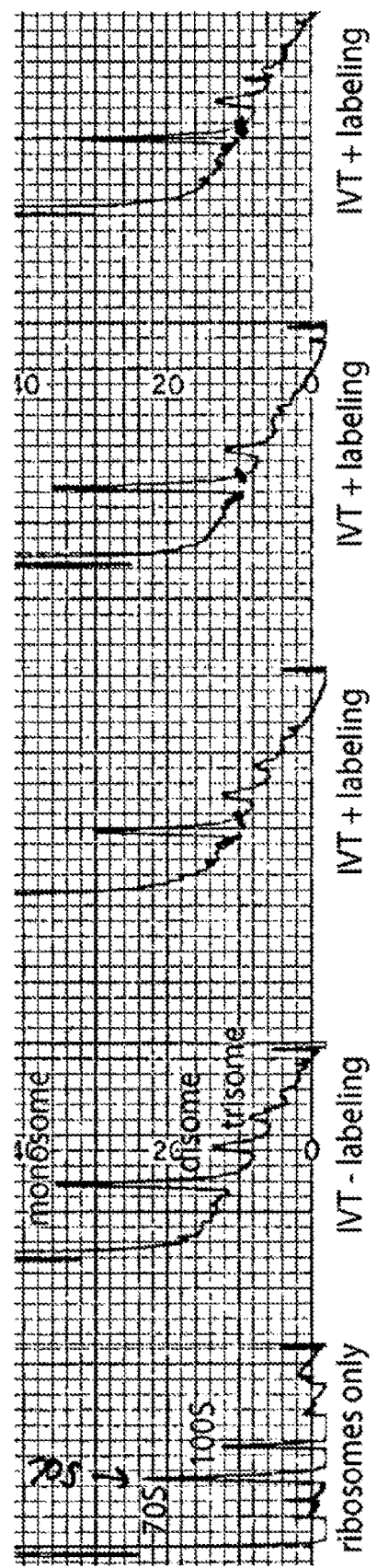
FIG. 24

SINGLE-MOLECULE PHENOTYPE ANALYSIS

CROSS-REFERENCE

This application claims the benefit of U.S. Provisional Patent Application No. 62/052,175, filed Sep. 18, 2014, which application is incorporated herein by reference in its entirety.

STATEMENT REGARDING FEDERALLY SPONSORED RESEARCH

This invention was made with government support under Grant No. GM050945 and Grant No. GM065050 awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "BERK-234WO_SeqList_ST25.txt" created on Sep. 15, 2015 and having a size of 3 KB. The contents of the text file are incorporated by reference herein in their entirety.

INTRODUCTION

Single molecule spectroscopies are invaluable tools in the study of complex biological systems due to their unique ability to dissect spatial and temporal heterogeneities present within ensembles of biomolecules. Such complex biological systems include the dynamic properties of individual molecules, e.g., multi-step processive catalysis, transient interactions, conformational fluctuations, folding mechanisms, cooperative structural transitions, etc., that are often lost to traditional ensemble averaging. For example, single molecule fluorescence resonance energy transfer (smFRET) has the ability to reveal dynamic conformational processes such as protein folding because of its sub-nanometer spatial and low-nanosecond temporal resolutions at the single molecule level. In addition, multi-labeling single molecules for smFRET at various positions further promises to reveal structural information and allow for identification of conformationally distinct single molecules. Despite their power and popularity, and as a direct consequence of their exquisite sensitivity, the preparation of protein samples, particularly at high-throughput, for single molecule biophysics applications remains a challenging rate-limiting barrier to progress.

Single molecule fluorescence studies place stringent demands on sample labeling specificity, efficiency, and homogeneity. For example, sample preparation for smFRET requires the dual-labeling of target biomolecules with pairs of donor and acceptor fluorescent dyes and is consequently a particularly low-throughput and inefficient process.

In vivo production of proteins for such applications typically requires the expression, purification, and dual-labeling of nanomole quantities of target proteins despite the fact that single molecule experiments consume only femtomoles of labeled sample. For cytotoxic, protease-sensitive, or aggregation-prone samples (e.g., intrinsically disordered proteins) in vivo expression already presents significant challenges. For example, standard in vivo sample generation for smFRET involves the steps of: 1) identification of suitable (i.e. solvent-accessible and non-perturbing) dye/probe-labeling sites; 2) plasmid-based cloning of genes encoding chemically-reactive (and often unnatural) amino acids at these desired sites; 3) transformation of these plasmids into an appropriate expression strain; 4) culture growth, induction, and lysis; 5) purification of the target protein to homogeneity; 6) efficient and specific dye attachment; and finally 7) sample post-processing to remove any excess unconjugated free-dyes/probes or compositional sample heterogeneity. All of these steps introduce significant variability and inefficiency necessitating a minimum of two weeks for the production of a single dual-labeled protein sample suitable for smFRET applications and often requiring additional purifications to supplement inefficiencies in steps 4-7. For these reasons, in vivo sample preparation hampers the execution of many single molecule protein biophysics studies.

Regarding the dye attachment step, the current methods for site-specific dual-probe attachment, such as enzymatic dye coupling and unnatural amino acid (UAA)-tagging offer high specificity and sensitivity but the large peptide tags required by these approaches can often perturb protein structure/function. Furthermore, overall specificity and efficiency of such approaches is entirely dependent on low-throughput target purification due to the necessity to purify away non-target endogenous host proteins and truncated proteins that have incorporated the UAA-tag.

A number of extract-based In vitro translation (IVT) systems have also been used for the co-translational incorporation of visibly-excitable fluorescent UAAs at efficiencies sufficient for ensemble-based detection. While economical and scalable, extract-based IVT and co-translational labeling has major limitations with respect to single molecule applications. For example, extract-based IVT are not ribonuclease and protease-free and thereby hinder the directed evolution of proteins and peptidomimetics by ribosome/mRNA display. Furthermore, extract-based IVT systems do not allow for total control over the local environment for nascent polypeptide folding or the translational apparatus, which is necessary for quantitative, codon-specific, and target-specific UAA incorporation.

Thus there remains a need for non-extract-based IVT methods, e.g., high-throughput non-extract-based IVT methods, for use in production of dual-labeled protein samples for single molecule analysis, e.g., smFRET applications, and advances in screening pipelines to facilitate the use of such samples in biophysics applications.

SUMMARY

Aspects of the present disclosure include methods of producing modified polypeptides and modified polypeptide-ribosome or polypeptide-mRNA complexes, and methods of screening polynucleotide and polypeptide libraries. The present disclosure also provides polypeptide libraries useful in screening for single molecule phenotypes. Also provided are kits useful for producing polypeptides capable of being modified using methods disclosed herein.

In practicing the methods according to certain embodiments of the present disclosure, an unnatural amino acid containing a reactive group, e.g., an azide or alkyne reactive group, is incorporated into a growing polypeptide by use of an in vitro cell-free translation reaction. In some instances, the translation reaction producing the growing polypeptide is stalled so as to produce a polypeptide-ribosome or polypeptide-mRNA complex. In yet other embodiments, the reactive group on the incorporated unnatural amino acid is utilized for the attachment of a heterologous moiety to the unnatural amino acid, and thus the polypeptide, by a chemical reaction, e.g., by a click chemistry reaction, e.g., copper (I)-catalyzed azide-alkyne cycloaddition, ligand-assisted copper catalyzed azide-alkyne cycloaddition (CuAAC), strain-promoted azide-alkyne cycloaddition (SPAAC), etc.

Kits containing reagents for performing a cell-free in vitro translation reaction in the presence of an unnatural amino acid, such that the unnatural amino acid is incorporated into a growing polypeptide, are also provided in the present disclosure. In some embodiments, the unnatural amino acid contains a reactive group, e.g., an azide reactive group, useful in producing a modified polypeptide by the attachment of a heterologous moiety through a click chemistry reaction.

Also disclosed are methods of screening polynucleotide libraries for single molecule phenotypes. In certain embodiments, a polynucleotide library is used to generate a modified polypeptide library by methods described herein. In some embodiments, the growing polypeptides of the polypeptide library are stalled to produce polypeptide-ribosome or polypeptide-mRNA complexes and the untranslated polynucleotides of the stalled complex are used to identify the polynucleotide of the polynucleotide library from which the polypeptide-ribosome or polypeptide-mRNA complex was derived. For example, sequencing the untranslated polynucleotides of polypeptide-ribosome or polypeptide-mRNA complex serves to identify the polypeptide-ribosome or polypeptide-mRNA complex. In some instances a single molecule phenotype of the generated polypeptide is detected, wherein detection is made possible by a heterologous moiety attached to the polypeptide through click chemistry, e.g., copper(I)-catalyzed azide-alkyne cycloaddition, utilizing a reactive group, e.g., a azide or alkyne reactive group, on an unnatural amino acid incorporated into the polypeptide by a cell-free in vitro translation reaction.

The present disclosure also provides methods for producing a library of multi-modified polypeptides, e.g., polypeptides modified at two or more residues, from a polynucleotide library useful in the screening for single molecule phenotypes. In certain instances, the multi-modified polypeptide is generated through the incorporation of unnatural amino acids into the growing polypeptide during a cell-free in vitro translation reaction. For example, the incorporated unnatural amino acids may contain azide or alkyne reactive groups useful for attaching at least two heterologous moieties to the unnatural amino acids and thus the polypeptide. In certain embodiments an in vitro translation reaction is stalled thus producing a multi-modified polypeptide-ribosome or polypeptide-mRNA complex that remains associated with untranslated polynucleotide of the polynucleotide library. In certain instances, multiple heterologous moieties attached to a single polypeptide-ribosome or polypeptide-mRNA complex interact to produce a detectable phenotype. In certain embodiments, untranslated polynucleotide associated with the multi-modified polypeptide-ribosome or polypeptide-mRNA complex is sequenced so as to identify the multi-modified polypeptide-ribosome or polypeptide-mRNA complex. In certain instances, a single molecule phenotype detected by the interaction of heterologous moieties attached to a polypeptide-ribosome or polypeptide-mRNA complex is correlated with the sequenced polynucleotide associated with the polypeptide-ribosome or polypeptide-mRNA complex thus identifying the polynucleotide of the library that is correlated with the detected phenotype.

The present disclosure also provides a method for screening a polypeptide library for a phenotype, wherein each polypeptide of the library is attached to a polynucleotide which serves as a barcode to allow for the identification of each polypeptide of the library and each polypeptide of the library also contains at least one incorporated unnatural amino acid containing a reactive group, e.g., an azide or alkyne reactive group. In certain embodiments a heterologous moiety is attached to each member of the polypeptide library by a chemical reaction, e.g., a cycloaddition reaction, by means of the reactive group, e.g., an azide or alkyne reactive group, of the incorporated unnatural amino acid. In certain instances a second library of molecules, in which each molecule is also attached to a polynucleotide barcode and a second heterologous moiety, is introduced to the first library and the heterologous moieties of the two libraries interact to produce a detectable signal, e.g., a FRET signal. In certain embodiments the polynucleotide barcodes of the members of a detected interaction, e.g., a polypeptide of the first library that interacts with a molecule of the second library, are sequenced in order to identify one or more of the interacting members.

Also provided is a polypeptide library wherein each polypeptide of the library contains an attached polynucleotide barcode, an incorporated unnatural amino acid with an azide or alkyne reactive group, and an attached moiety useful in binding the polypeptide to a substrate. As described in more detail below, in certain instances attachment to a substrate allows for the single molecule sequencing of attached polynucleotide barcodes and thus the identification of single molecules displaying a phenotype or the molecular partners of a single molecular interaction.

BRIEF DESCRIPTION OF THE DRAWINGS

FIG. 5 provides (Table 1) components, concentrations, submix compositions, and aminoacyl-tRNA synthetase activities of the home-made Protein Synthesis Using Recombinant Elements (PURE) reaction.

FIG. 6 provides (Table 2) liquid chromatography-mass spectrometry detected ions (right) of predicted peptide fragments (left) for stalled RNC complexes of T4L wt*-M D61M D159C-secM and the T4L construct used (SEQ ID NO:1).

FIGS. 12A-12B provide Table 4 which provides a general overview of proteins labeled for single molecule biophysical studies using the methods described herein.

FIGS. 13A-13D provides Table 5 which provides a detailed list of constructs used in testing the methods for PURE-IVT-based generation of dual-labeled smFRET polypeptides.

FIG. 23 depicts similar kinetics to FIG. 22 at varied copper concentrations while holding the Cu:BTTP concentration constant.

FIG. 24 depicts chromatographs of analytical sucrose gradient analyses of various IVT reactions.

FIG. 25 shows the effects of varied conditions on BTTP/CuAAC reactions.

DEFINITIONS

Figure 1:
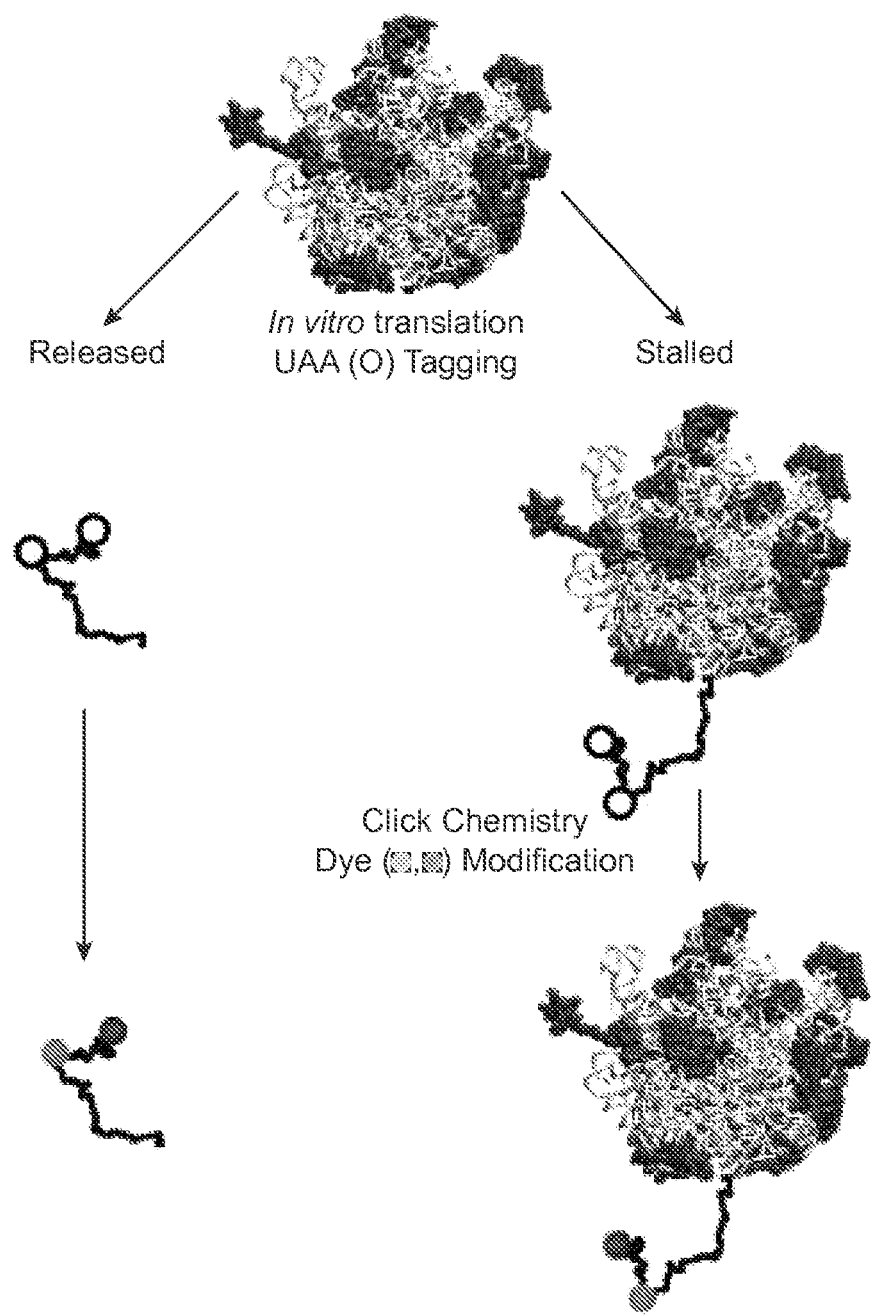
FIG. 1 depicts a sample generation strategy for single molecule Forester resonance energy transfer (FRET). High-throughput in vitro translation (IVT) and unnatural amino acid (UAA) tag (○) incorporation are carried out using a customized purified and reconstituted E. coli IVT system. Purification of stalled ribosome-bound nascent chains (RNCs) (right branch) or released protein samples (left branch) from other translation components is facilitated by the defined and reconstituted nature of the IVT system. Finally, quantitative post-translational fluorescent dye conjugation to all UAA tags on RNCs or released proteins is achieved using a highly efficient ligand-assisted Cu-catalyzed azide-alkyne cycloaddition (CuAAC) click-chemistry reaction.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to a binding domain of a polypeptide) refers to a non-covalent interaction between macromolecules (e.g., between two proteins). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Binding interactions are generally characterized by a dissociation constant (Kd) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower Kd.

"Crosslinking" may refer to ionic bonding or covalent bonding and may, in some cases, refer to the linking of two polymers or the linking of a polymer to a heterologous moiety. In some instances, crosslinking may refer to the stabilization of transient interactions into non-transient interaction or the conversion of a reversible interaction into an irreversible interaction. For example, in some instances, two molecules held in close proximity, e.g., by a binding reaction, may be cross-linked, e.g., by covalent interaction, so as to render the two molecules attached.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different manners. To determine sequence identity, sequences can be aligned using various methods and computer programs (e.g., BLAST, T-COFFEE, MUSCLE, MAFFT, etc.), available over the world wide web at sites including ncbi(dot)nlm(dot)nili(dot)gov/BLAST, ebi(dot)ac(dot)uk/Tools/msa/tcoffee/, ebi(dot)

ac(dot)uk/Tools/msa/muscle/, mafft(dot)cbrc(dot)jp/alignment/software/. See, e.g., Altschul et al. (1990), *J. Mol. Biol.* 215:403-10.

The term "naturally-occurring" or "unmodified" or "native" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is naturally occurring. Accordingly, a biomolecule or organism may be "unnatural" or "non-naturally-occurring", e.g., where a biomolecule, e.g., a nucleic acid, a polypeptide, e.g., or a cell, or an organism, is intentionally modified by a human, e.g., in the laboratory.

"Heterologous moiety," as used herein in the context of a macromolecule comprising a heterologous moiety, refers to a moiety that is not found in the macromolecule in nature, e.g., a moiety that is attached to a macromolecule in the laboratory by human intervention or activity. For example, according to the definition provided herein, a fluorescent molecule, e.g., Alexa Fluor 488 Azide (Life Technologies, Grand Island, N.Y.), is a heterologous moiety when attached to a macromolecule, e.g., a polypeptide, that is not attached to the fluorescent molecule in nature. In some instances, a heterologous moiety may be a light activated or light deactivated heterologous moiety. Such light activated or light deactivated heterologous moieties may, in some instances, be cross-linked to a molecule or interest or used in the cross-linking of a molecular of interest to a second molecule or substrate.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms. Alternatively, DNA sequences encoding RNA that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment.

The term "polypeptide-ribosome complex" or "ribosome-bound nascent chain" or "RNC" as used herein refers to the collection of molecules that constitute a ribosome attached to the polypeptide being synthesized by the ribosome. Polypeptide-ribosome complexes are produced in the laboratory by the stalling of translation by any convenient method of ribosome stalling. Common methods of ribosome stalling are known in the art and described herein. For example, in some instances ribosome stalling may be achieved through the use of a SecM sequence or a truncated codon, e.g., a truncated mRNA without an in-frame stop codon. Such a generated and stalled polypeptide-ribosome complex may be stabilized by any convenient chemical means, e.g., through lowering the temperature of the complex and/or the addition of cations, e.g., magnesium ions. Ribosome display may be performed through the production of a polypeptide-ribosome complex which remains bound to the polynucleotide from which a subject polypeptide is being translated.

The term "polypeptide mRNA complex" or "protein-mRNA complex" as used herein refers to the collection of molecules that constitute a mRNA attached to the polypeptide from which the polypeptide is synthesized. Polypeptide mRNA complexes may in some cases encompass polypeptide-ribosome complexes, as described above, and, in other instances, may not have an attached ribosome or may only transiently have an attached ribosome. In some instances, a polypeptide mRNA complex may be produced from generating a polypeptide from an mRNA and linking the mRNA to the generated polypeptide, e.g., before, during, or after the mRNA and polypeptide dissociate from the ribosome. Convenient methods of attaching a polypeptide to its parent mRNA are known in the art and may include but are not limited to, e.g., puromycin mediated linking which includes attachment via a puromycin moiety.

The term "polynucleotide barcode" or "barcode" or "polynucleotide tag" are used interchangeably and, according to the present disclosure, as used herein refer to a sequence of nucleotides, i.e., an oligonucleotide, an oligomer, or an oligo. According to the present disclosure a barcode is attached to a subject molecule. An attached polynucleotide barcode finds use in tagging or labeling a single macromolecule, e.g., a polynucleotide, a polypeptide, a ribonucleoprotein, a carbohydrate, a lipid, a complex, and the like. A single polynucleotide barcode also finds use in tagging or labeling a plurality of macromolecules, e.g., a group of related polynucleotides, a group of related polypeptides, a group of related ribonucleoproteins, a group of related carbohydrates, a group of related lipids, a group of related complexes, and the like. Unique barcodes are used to individually differentiate members of a group from one another, e.g., unique barcodes attached to individual ribonucleoproteins serves to individually differentiate each ribonucleoprotein from every other ribonucleoprotein. Unique barcodes are also used to differentiate groups of related members, e.g., derived from the same species, derived from the same individual, derived from the same library, derived from the same experiment, derived from the same sample, etc., from other groups. For example, the same unique barcode is attached to a first plurality of related ribonucleoproteins and a second unique barcode is attached to a second plurality of related ribonucleoproteins such that when the first and second pluralities of related ribonucleoproteins are mixed the barcodes serve to indicate the group to which each ribonucleoprotein belongs. A polynucleotide barcode may be of any useful length, e.g., about 1-100 nucleotides, about 5-10 nucleotides, about 10-15 nucleotides, about 10-18 nucleotides, about 18-25 nucleotides, or about 25-50 nucleotides, depending on the particular contexts in which the barcode is being used and how many individual members or individual groups are preferably differentiated. In certain instances the barcode is between about 17 to about 22 nucleotides in length, e.g., about 17 nucleotides, about 18 nucleotides, about 19, nucleotides about 20 nucleotides, about 21 nucleotides, or about 22 nucleotides. For example, the use of a barcode about 1 nucleotide in length differentiates 4 individual members or groups, about 2 nucleotides in length differentiates 16 individual members or groups, about 3 nucleotides in length differentiates 64 individual members or groups, about 4 nucleotides in length differentiates 256 individual members or groups, about 5 nucleotides in length differentiates 1024 individual members or groups, and so on. Thus the use of a barcode over about 9 nucleotides in length differentiates over 1 million unique individual members or groups and a barcode over about 14 nucleotides in length differentiates over 1 billion unique individual members or groups.

The term "sequencing" as used herein and as applied to polynucleotides, refers to the determination of the order of nucleotides in a polynucleotide. Unless specifically noted, sequencing may refer to any appropriate sequencing method that may be used in the context of the invention where it is described. In certain instances, sequencing of long reads, e.g., from about 50 to about 500 nucleotides, e.g., from about 100 to about 500 nucleotides, may be used to determine the nucleotide sequence of an entire gene or gene product, e.g., a coding sequence (CDS), an mRNA, a cDNA, a gene locus, a miRNA, an allele, a mutant, a synthetic construct, and the like. Sequencing of long reads may also include the sequencing of any polynucleotide barcode or polynucleotide tag attached to a gene or gene product so as to correlate a barcode with a gene or gene product, as described elsewhere herein.

In certain instances, sequencing of sort reads, e.g., less than about 100 nucleotides, e.g., from about 17 to about 25 nucleotides or from about 1 to about 17 nucleotides, may be used to determine the nucleotide sequence of a short portion of a longer sequence or a short oligomer, e.g., a barcode or tag. As such, in some instances, sequencing of a short sequence may serve to identify a longer sequence with which the short sequence is correlated without the necessity for sequencing the longer sequence, e.g., the sequencing of an associated barcode may serve to identify a longer sequence, e.g., a coding sequence, with which the barcode is associated without the need to sequence the barcode.

Common sequencing methods include sequencing-by-synthesis, Sanger or gel-based sequencing, sequencing-by-hybridization, sequencing-by-ligation, or any other available method. Sequencing may be performed on any applicable platform, such non-limiting examples include: pyrosequencing, sequencing-by-synthesis, single-molecule sequencing, nanopore sequencing, sequencing-by-ligation, or sequencing-by-hybridization. Non-limiting applicable commercially available platforms include those available from Illumina (RNA-Seq) and Helicos (Digital Gene Expression). "Next generation" sequencing methods include, but are not limited to those commercialized by: Roche Lifesciences including but not limited to the methods and apparatus described in Margulies et al., Nature (2005) 437:376-380 (2005); and U.S. Pat. Nos. 7,244,559; 7,335,762; 7,211,390; 7,244,567; 7,264,929; 7,323,305; 2) Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058; Applied Biosystems (e.g. SOLiD sequencing); Dover Systems (e.g., Polonator G.007 sequencing); Illumina as described U.S. Pat. Nos. 5,750,341; 6,306,597; and 5,969,119; and Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764.

In certain instances the term "single molecule direct sequencing" is used to refer to the determination of the nucleotide sequence of a single polynucleotide directly. References to single molecule direct sequencing may include multiplexed and massively multiplexed single molecule direct sequencing where the nucleotide sequence of many individual polynucleotides is determined simultaneously. Common methods of single molecule direct sequencing include sequencing-by-synthesis, optical sequencing and mapping, nanopore sequencing, and the like and are known in the art, see, e.g., Thompson & Milos (2011) *Genome Biology,* 12:217. "Single molecule sequencing" platforms include, but are not limited to, those commercialized by: Helicos BioSciences including but not limited to the methods and apparatus described in U.S. Pat. Nos. 8,367,377, 7,994,304, 7,948,625, 7,897,345, 7,767,805, 7,767,400, 7,666,593, 7,635,562, 7,491,498, 7,482,120, 7,282,337, 7,220,549, and 7,169,560; Pacific Biosciences (SMRT technology) including but not limited to the methods and apparatus described in Levene et al. (2003) *Science,* 299:682-686, U.S. Pat. Nos. 8,603,741, 8,501,405, 8,481,264, 8,455,193, 8,420,366, 8,370,079, 8,367,159, 8,304,191, 8,153,375, 7,960,116, 7,939,256, 7,901,889, 7,858,311, 7,745,116, 7,476,503, 7,462,452, 7,315,019, 7,313,308, and 7,302,146; and Life Technologies (StarLight) including but not limited to the methods and apparatus described in U.S. Pat. Nos. 8,632,975, 8,603,792, 8,536,099, 8,314,216, 8,173,198, 8,058,414, 8,017,338, and 7,329,429. In certain instances, the term "sequencing" as applied to polypeptides may also refer to the determination of the order of amino acids in polypeptide sequence. All references are herein incorporated by reference. Such methods and apparatuses are provided here by way of example and are not intended to be limiting.

The term "single molecule" or "single-molecule" as used herein as it applies to single molecule studies, e.g., single molecule sequencing, single molecule spectroscopies, single molecule analysis, single molecule fluorescence, etc., is used according to its ordinary meaning in the art. In certain instances, single molecule studies may be performed on more than one molecule at a time, e.g., single molecule studies may be performed in parallel, e.g., multiplexed, or may be performed in massively parallel studies, e.g., massively multiplexed. In certain instances, a single molecule analysis may be performed on a single molecule that is complexed with one or more additional molecules.

The term "attachment" or "attached" as used herein and as applied to atoms, molecules, nucleotides, polynucleotides, amino acids, peptides, polypeptides, proteins, moieties, and the like may refer to reversible or irreversible attachment and strong or weak attachments. For example, irreversible attachments may refer to covalent attachments or chemical bonds or linkages or of two or more molecules that may not be disassociated without the breaking of chemical bonds. In other examples, reversible attachments may refer to strong associations, e.g., molecular binding interactions or attractive interactions, of two or more molecules that may be disassociated without the breaking of covalent bonds. It will be clear to one skilled in the art, from the nature of the attachment or the nature of the attachment partners, where irreversible or reversible attachments are described herein.

The term "interaction" or "interacts" as used herein and as applied to the interaction of two or more particles or atoms or molecules, or parts of atoms or molecules, refers to a mutual or reciprocal action or influence of the entities on one another. Interactions may or may not require two entities coming into physical contact. For example, an interaction between two molecules may involve the molecules coming into physical contact with one another, e.g., binding one another. In other examples, an interaction may involve two molecules coming into proximity to one another such that one molecule can influence the other, e.g., energy may be transferred from one molecule to the other.

The term "phenotype" as used herein and as it applies to a single molecule phenotype refers to any subject chemical characteristic, biochemical characteristic, physical characteristic, biophysical characteristic, or other characteristic or property of a subject molecule that is deemed either desirable or undesirable for a particular purpose. Single molecule phenotypes of the instant disclosure are observed or detected properties of a single molecule and may, in some instances, include transient or dynamic characteristics of a particular single molecule as described herein. For example, preferred phenotypes of polypeptides may include desirable structural characteristics, e.g., a particular three dimensional conformation, steric availability of an active site, steric unavailability of an active site, and the like. Other, non-exclusive examples of preferred phenotypes may include active characteristics of a molecule (e.g., characteristics that uniquely distinguish a molecule based on its dynamic properties and/or based on a resolvable difference it may have with other members of its ensemble), e.g., binding affinity with a particular ligand or target, on/off rates with a particular binding partner, folding speed of a polypeptide, conformational conversion rate, fluorescent characteristics of a fluorescent protein, processivity of a particular enzyme, thermostability of a particular enzyme, and the like.

General methods in molecular and cellular biochemistry can be found in such standard textbooks as Molecular Cloning: A Laboratory Manual, 3rd Ed. (Sambrook et al., Cold Spring Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a," "an," and "the" include plural referents unless the context clearly dictates otherwise. Thus, for example, reference to "a polypeptide" includes a plurality of such polypeptides and reference to "the amino acid" includes reference to one or more amino acid and equivalents thereof known to those skilled in the art, and so forth.

It is also noted that definitions provided in one section of this application (e.g., the "Definitions" section) may also apply to embodiments described in another section of the application (e.g., the "Examples" section) even if a term is described as applying to an embodiment of a particular section.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflict with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

DETAILED DESCRIPTION

Aspects of the present disclosure include methods of in vitro production of modified polypeptide-ribosome or polypeptide-mRNA complexes, kits for the in vitro production of readily modified polypeptides, methods of screening polynucleotide libraries by producing modified polypeptide-ribosome or polypeptide-mRNA complexes, methods of screening libraries of modified polypeptides, and readily modified polypeptide libraries useful in screening for phenotypes. In practicing methods according to certain embodiments, readily modified polypeptides are generated through the incorporation of unnatural amino acids, containing reactive groups, e.g., azide or alkyne reactive groups, into growing polypeptides during cell-free in vitro translation reactions. Such reactive groups are useful in the attachment of heterologous moieties by click chemistry. According to other aspects of the present disclosure, modified polypeptides are screened for detectable phenotypes and identified by sequencing, e.g., sequencing of encoding nucleic acids or portion thereof, sequencing of polynucleotide barcodes attached to the modified polypeptides, etc. Identification of molecules displaying a single molecule phenotype and/or involved in a single molecular interaction performed by immobilizing the modified polypeptide on a substrate compatible with single-molecule direct sequencing is also described.

Methods of Cell-Free In Vitro Translation

The present disclosure provides for methods of cell-free in vitro translation (IVT). Such IVT provides for the production of a polypeptide from a polynucleotide template in a defined reaction mixture. In certain instances, the polynucleotide template is an RNA template, e.g., a synthetic mRNA or an isolated mRNA, and IVT is performed independently of or in the absence of transcription. In certain instances, the polynucleotide template is a DNA template, e.g., a plasmid, a vector, a PCR product, ligated DNA, isolated DNA, genomic DNA, cDNA, etc., and IVT is performed in combination with a transcription reaction such that a transcription reaction is utilized to generate an RNA template immediately prior to or concomitant with the initiation of translation. In some instances, recombinant templates derived from natural sources, e.g., through molecular cloning, may be altered with the addition of heterologous sequence elements or internal mutations that alter particular codons, e.g., changing the amino acid coded for at a particular site. In one embodiment, the template, e.g., PCR-generated template, for IVT is subject to mutagenesis in order to generate a plurality of mutated templates and such mutagenesis may be exhaustive or non-exhaustive. Any convenient method for generating such mutated templates may be employed, including but not limited to, e.g., overlap-extension PCR.

Translation, i.e., protein or peptide synthesis, is a well understood cellular process which is described in detail in standard textbooks such as Molecular Biology of the Cell. 4th Ed. (Alberts et al., New York: Garland Science; 2002); Biochemistry. 5th Ed. (Berg et al., New York: W H Freeman; 2002); and Molecular Cellular Biology. 4th Ed. (Lodish et al., New York: W H Freeman; 2000), the disclosures of which are incorporated herein by reference. Such understanding has led to the development of Protein Synthesis Using Recombinant Elements (PURE) WT systems, for example, see Shimizu, Y. et al. (2001) Cell-free translation reconstituted with purified components. *Nature Biotechnology*, 751-755, and Shimizu Y. et al. (2005) Protein synthesis by pure translation systems, 299-304, the disclosures of which are incorporated herein by reference.

The present disclosure provides for protein synthesis by means of a PURE IVT reaction useful in practicing related methods disclosed herein. In certain aspects of the present disclosure, a PURE IVT reaction includes recombinant or isolated elongation factors (EF), initiation factors (IF), release factors (RF), ribosome recycling factor (RRF), aminoacyl-tRNA synthetases (aaRS), methionine transformylase (MTF), adenylate kinase (AK), creatine kinase (CK), nucleoside diphosphate kinase (NDK), inorganic pyrophosphatase (PPiase), ribosomes, and the like. In certain embodiments, a PURE IVT of the present disclosure includes all or some of the components listed in Table 1 provided in FIG. 5. In certain instances the PURE IVT components listed in Table 1 are also referred to as a "home-made" PURE IVT system.

One skilled in the art will recognize that the concentrations and amounts of each component of the PURE IVT mix provided in Table 1 may be altered or optimized to function in a particular PURE IVT reaction. Such alteration or optimization for a particular PURE IVT reaction may involve the increase or decrease of the final concentration or amount of any component of the PURE WT reaction provided in Table 1 by anywhere from about 0 to about 10 times, e.g., about 0.001 to about 0.01 times, about 0.01 to about 0.1 times, about 0.1 to about 1 times, about 1 to about 2 times, about 2 to about 3 times, about 3 to about 5 times, about 5 to about 7 times, about 7 to about 10 times, or as much as about 100 times the concentration or amount of the reagent as provided in Table 1. Such alterations and/or optimizations are performed such that robust IVT is maintained according to that described herein, including robust and/or quantitative incorporation of any desired UAA included in the IVT reaction.

One skilled in the art will also recognize that particular components of the PURE IVT reaction provided in Table 1 may be removed or substituted according to the specifics of a particular PURE IVT reaction. For example, when a polynucleotide template is utilized for a PURE IVT reaction that does not encode one or more particular amino acids, that particular amino acid(s) and the relevant aaRS may be excluded from the PURE IVT reaction. Likewise, one skilled in the art will also recognize that where in vitro transcription is unnecessary, because an RNA template is provided for protein synthesis, components of the reaction related to transcription may be excluded. One skilled in the art will also recognize functionally equivalent components to those provided in Table 1 that may be exchanged or added without inhibiting protein synthesis, e.g., functionally equivalent components to those components listed in Table 1 under "other components", functionally equivalent components to those components listed in Table 1 under "separately added", analogs of nucleoside triphosphates, functionally equivalent IFs, EFs, RFs, RRs, RRFs, ribosomes and the like.

The cell-free in vitro translation of the present disclosure provides for the codon-specific or residue specific and co-translational robustly quantitative incorporation of unnatural amino acids (UAAs) into a growing polypeptide with the use of unnatural aminoacyl-tRNAs (UAA-tRNAs). Such UAA-tRNAs are generated by charging a tRNA, e.g., a native tRNA or a synthetic tRNA, with an UAA using an aaRS, e.g., an endogenous/native aaRS or a mutant/modified aaRS. In certain instances, an UAA is charged onto a native tRNA by an endogenous or native aaRS. In certain instances, an UAA is charged onto a synthetic tRNA by an endogenous or native aaRS. In certain instances, an UAA is charged onto a synthetic tRNA by a mutant or modified aaRS. In certain instances, an UAA is charged onto a native tRNA by a mutant or modified aaRS. Orthogonal aaRS/tRNA pairs and pre-acylated UAA-tRNAs suitable for use in the methods described herein include those known in the art, see, e.g., Liu, C. & Schultz (2010) *Annual Review of Biochemistry,* 413-444; Davis & Chin (2012) *Nature Reviews Molecular Cell Biology,* 168-182; Gubbens, et al., (2010) *Rna-a Publication of the Rna Society,* 1660-1672; Miura, et al. (2010) *Bulletin of the Chemical Society of Japan,* 546-553; Lee, et al. (2000) *Nature Structural Biology,* 28-33; and Hendrickson, et al. (2004) *Annual Reviews of Biochemistry,* 147-176; the disclosures of which are incorporated herein by reference.

In some instances, the Flexizyme method may be used to incorporate UAA into polypeptides, e.g., nascent polypeptide chains, according to the methods disclosed herein such that UAA is sufficiently efficient for single molecule studies as described. Suitable methods of Flexizyme UAA incorporation include those known in the art, see, e.g., Goto et al. (2011) *Nature Protocols.* 6:779-790, the disclosure of which is incorporated herein by reference.

One skilled in the art will recognize that any suitable UAA can be incorporated into any suitable polypeptide through the use of a suitable UAA-tRNA and by use of the PURE WT methods described herein. In certain instances, UAAs incorporated into a polypeptide are analogs of methionine, e.g., azidohomoalanine (AHA) and homopropargylglycine (HPG), such molecules are represented by but are not limited to the chemical structures provided in FIG. 8. In certain instances, UAAs that may be incorporated into a polypeptide are analogs of aliphatic amino acids, e.g., glycine, alanine, valine, leucine, and isoleucine; hydroxyl or sulfur/selenium-containing amino acids, e.g., serine, cysteine, selenocysteine, threonine, and methionine; cyclic amino acids, e.g., proline; aromatic amino acids, e.g., phenylalanine, tyrosine, and tryptophan; basic amino acids, e.g., histidine, lysine, and arginine; or acidic amino acids, e.g., aspartate, glutamate, asparagine, and glutamine.

A UAA includes, e.g., a naturally occurring non-genetically encoded L-amino acids, synthetic L-amino acids or D-enantiomers of an amino acid. For example, UAAs include, but are not limited to, hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, 6-amino valeric acid, and 2,3-diaminobutyric acid.

For example, a genetically encoded amino acid can be substituted with a UAA. The following are non-limiting examples:

a) substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from $C_1$-$C_{10}$ carbons including branched, cyclic and straight chain alkyl, alkenyl or alkynyl substitutions;

b) substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains, including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination) carboxylic acids or any of the many well-known activated derivatives such as acid chlorides, active esters, active azolides and related derivatives) and lysine, ornithine, or 2,3-diaminopropionic acid;

d) substitution of acidic amino acids, including aspartic acid, glutamic acid, homoglutamic acid, tyrosine, alkyl, aryl, arylalkyl, and heteroaryl sulfonamides of 2,4-diaminoprionic acid, ornithine or lysine and tetrazole-substituted alkyl amino acids;

e) substitution of side chain amide residue, including asparagine, glutamine, and alkyl or aromatic substituted derivatives of asparagine or glutamine; and f) substitution of hydroxyl containing amino acids, including serine, threonine, homoserine, 2,3-diaminopropionic acid, and alkyl or aromatic substituted derivatives of serine or threonine.

In one embodiment, reaction conditions of a PURE IVT are optimized such that the ratio of UAA, e.g., methionine analogs (AHA) and homopropargylglycine (HPG), incorporation to analogous natural amino acid (AA), e.g., methionine, incorporation is about 1:1. One skilled in the art will recognize from the disclosure of robustly quantitative UAA incorporation methods provided herein that reaction conditions, e.g., monovalent ion concentrations, divalent ion concentrations, polyamine concentrations, and the like, may be adjusted to achieve a desired ratio of UAA to AA incorporation at maximal efficiency. One skilled in the art will also recognize from the disclosure of robustly quantitative UAA incorporation methods provided herein that a desired ratio of UAA to AA incorporation may also be achieved by altering relative concentrations of subject UAAs and AAs in order to achieve maximal incorporation efficiency at the desired ratio. In certain cases, desired ratios of UAA to AA incorporation may vary depending on the particular practical application and may be higher or lower than about 1:1, e.g., about 1:2, about 1:3, about 1:4, about 1:5, about 1:10, about 1:100, about 2:1, about 3:1, about 4:1, about 5:1, about 10:1, or about 100:1. The ordinary skilled artisan will further recognize from the disclosure of robustly quantitative UAA incorporation methods provided herein where altering factors affecting the UAA incorporation ratio will negatively impact incorporation efficiency, thus negatively impacting single molecule studies.

Methods of Generating Modified Polypeptides and Polypeptide-Ribosome or Polypeptide-mRNA Complexes The present disclosure provides methods for the generation of polypeptides that are readily modified. As it pertains to the present disclosure, by "readily modified" is meant modified easily, i.e., without the requirement for undue experimentation or an undue number of chemical or biochemical steps. A modification of a readily modified polypeptide may be performed in few chemical steps, e.g., in as few as 10 steps, in as few as 6 to 10 steps, in as few as 1 to 5 steps, in as few as 5 steps, in as few as 4 steps, in as few as 3 steps, in as few as 2 steps, or in as few as 1 step.

Furthermore, the present disclosure provides methods for the generation of readily modified polypeptides under conditions, e.g., reaction conditions or environmental conditions, which allow for normal activity and/or function of the readily modified polypeptide and/or target or binding partners of the readily modified polypeptide.

The present disclosure provides for the modification of a polypeptide with an incorporated UAA, the incorporation of which can be achieved by methods provided herein. In some instances, an incorporated UAA may be referred to as a tag, a UAA tag or a bio-orthogonal tag and the process of UAA incorporation may be referred to as tagging, UAA tagging, metabolic tagging, site-specific tagging, etc. In certain embodiments, modification of a polypeptide makes use of a reactive group on an incorporated UAA, e.g., attachment of a heterologous moiety to an incorporated UAA by a chemical reaction. In some instances, incorporation of a UAA and subsequent chemical attachment, e.g., covalent attachment, of a heterologous moiety is referred to as tag-and-modify labeling or chemical labeling. Non-limiting examples of chemical reactions useful in modifying incorporated UAAs are provided in Table 3, along with the components, chemical characteristics, and practical consideration of such reactions.

TABLE 3

Bio-orthogonal Tag-and-Modify labeling chemistries

| Chemistry | UAA Tag | Conjugate | Rate Constant $(M * s)^{-1}$ | Comments |
| --- | --- | --- | --- | --- |
| Oxime Ligation | Ketone/ Aldehyde | alkoxyamine-X | .001 (no catalyst) .061 (@ .1M catalyst) | Given rates at pH 7. Small linker regioselective. |
| CBT condensation | 1,2-aminothiol | CBT-X | 9 | Reversible background thiol reactivity. Large linker. |
| Tetrazine ligation | Strained alkene/ Strained alkyne | tetrazine-X | 1-17000 | Tetrazine-dye quenching (turn-on fluorescence upon reaction). Large linker. Generally not regioselective. |
| SPAAC | Azide | DIMAC-X | .003 | Azide reduction/inactivation during translation. Large rigid linker. Significant background thiol-yne reactivity. Generally not regioselective but often symmetric. |
| | | DIBO-X | .057 | |
| | | DIFO-X | .076 | |
| | | BCN-X | .29 | |
| | | BARAC-X | .96 | |
| | Strained alkyne | Azide-X | .001-.29 | |
| Ligand-assisted CuAAC | Azide | Alkyne-X | ~3 (*TBTA*) | Small linker. Regioselective. Potential oxidative damage to sample. Rates shown are assumed to be linearly dependent on $[Cu]^2$ and are calculated at [Cu] = .5 mM, [L] = 1 mM without competing Cu-center aggregation. |
| | Alkyne | Azide-X | ~8000 (*BPS*) | |
| | | | ~32000 (BHPTA) | |
| | | | ~1250 (*THPTA*) | |
| | | | ~400 (BTTES) | |
| | | | ~800 (BTTAA) | |
| | | | ~500 (BTTP) | |
| | | | ~533 (BTTPS) | |
| | Alkyne | Picolyl azide-X | ~10750 (BTTPS) | |

Chemically-reactive UAA functionalities compatible with robustly-quantitative sense-codon reassignment (bold) and suppression-based genetic-code expansion (underlined) are indicated, as are all commercially available dye conjugates (italics). Cyanobenzothiazole (CBT), Strain-promoted azide-alkyne cycloaddition (SPAAC), copper-catalyzed azide-alkyne cycloaddition (CuAAC), 6,7-dimethoxyazacyclooct-4-yne (DIMAC), difluorinated cyclooctyne (DIFO), bicyclononyne (BCN), biarylazacyclooctynones (BARAC), Tris(benzyltriazolyl-methyl)amine (TBTA), Bathophenanthroline disulfonic acid (BPS), Bis(3-hydroxypropyltriazolylmethyl)amine (BHPTA), Tris(3-hydroxypropyltriazolyl-methyl)amine (THPTA), Bis(tertbutyl)-tris(triazolylmethyl)amine-ethane sulfonic acid (BTTES), Bis(tertbutyl)-tris(triazolylmethyl)amine-propanol (BTTP).

In certain embodiments, modification of a polypeptide through covalent attachment of a heterologous moiety to a reactive group on an UAA is achieved by a ligation reaction, e.g., an oxime ligation, a Staudinger ligation, a solid phase peptide synthesis, and the like. In certain embodiments, modification of a polypeptide through covalent attachment of a heterologous moiety to a reactive group on a UAA is achieved by a cycloaddition reaction, e.g., a cyanobenzothiazole condensation, a tetrazine ligation, a strain-promoted azide-alkyne cycloaddition, a copper catalyzed cycloaddition, a ligand-assisted copper catalyzed cycloaddition, and the like. In certain embodiments, the cycloaddition reaction used to attach a heterologous moiety to the UAA is a copper catalyzed cycloaddition, e.g., a subject copper catalyzed cycloaddition is a cycloaddition represented by the following:

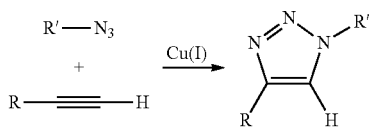

One skilled in the art will recognize that substitutions to individual atoms of the above chemical structures may be made, e.g., atom substitutions between atoms with similar chemical properties, in order to alter or optimize a reaction to specific preferred reaction conditions, e.g., other non-metals (e.g., C, N, O, P, S, or Se) or metalloids (B, Si, Ge, As, Sb, Te, or Po) may be substituted for N or C. One skilled in the art will also recognize that substitutions between metal catalysts of the above chemical reaction may be made, e.g., metal substitutions between metals with similar chemical properties, in order to alter or optimize a reaction to specific preferred reaction conditions, e.g., copper of other oxidation states (e.g., Cu(II) or Cu(III)).

In other embodiments, the cycloaddition reaction used to attach a heterologous moiety to the UAA is a copper-free cycloaddition (i.e., a copper-free click chemistry reaction), e.g., a subject copper-free cycloaddition is a reaction represented by the following:

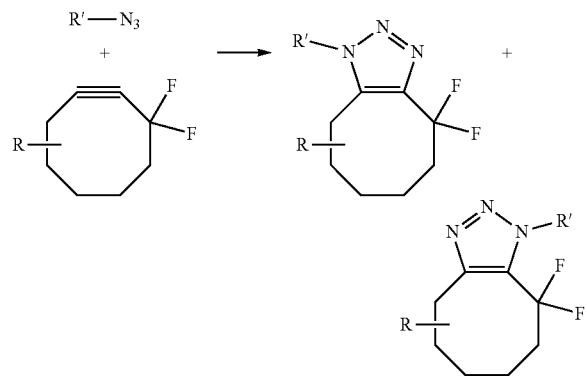

One skilled in the art will recognize that substitutions to individual atoms of the above chemical structures may be made, e.g., atom substitutions between atoms with similar chemical properties, in order to alter or optimize a reaction to specific preferred reaction conditions, e.g., other halogens (e.g., Cl, Br, I, or At) may be substituted for F. Such bio-orthogonal reactivity, e.g., bio-orthogonal click chemistry, is known in the art, see, e.g., U.S. Pat. No. 8,519,122; Bundy & Schultz (2010) Bioconjugate Chem, 255-263; Liu & Schultz (2010) Annual Review of Biochemistry, 413-444; and Davis & Chin Nature Reviews Molecular Cell Biology, 168-182; the disclosures of which are incorporated by reference herein.

In certain instances, the attachment of one or more heterologous moieties, e.g., the attachment of two heterologous moieties, may serve as a method of evaluating the sensitivity and specificity of a particular attachment reaction. For example, in one embodiment, the dual-labeling efficiency of IVT-produced polypeptide-ribosome complexes or polypeptide-mRNA complexes may serve as an effective measure for the sensitivity and specificity of the attachment reaction used to dual-label the polypeptide-ribosome complexes or polypeptide-mRNA complexes. In one embodiment, the dual-labeling efficiency of IVT-produced polypeptide-ribosome complexes or polypeptide-mRNA complexes may serve as an effective measure for the sensitivity and specificity of the click-chemistry or cycloaddition reaction used to dual-label the polypeptide-ribosome complexes or polypeptide-mRNA complexes, e.g., to evaluate the performance of particular click-chemistry or cycloaddition reagents.

In certain embodiments, such attachment reactions and such incorporation reactions as are described herein are utilized to incorporate a heterologous moiety for performing a crosslinking reaction, e.g., a cross-linking moiety. Such cross-linking moieties, as described herein, may be utilized for the covalent attachment of the cross-linking moiety containing molecule to any desired agent or substrate. In certain embodiments, a cross-linking moiety incorporated into or attached to a first macromolecule of the present disclosure may be utilized to link a first macromolecule to a second macromolecule by a cross-linking reaction. For example, in one embodiment, two macromolecules of the present disclosure may be cross-linked through the use of one or more crosslinking moieties upon interaction, e.g., to irreversibly link two binding partners, e.g., upon detection of a binding reaction or an association reported by any of the methods as described herein. In some instances, a cross-linking moiety incorporated into or attached to a macromolecule of the present disclosure may be utilized to link the macromolecule to a substrate, including but not limited to, e.g., a surface, a slide, a well, a bead, etc. Chemically reactive groups that find use as crosslinking moieties of the present disclosure are well known in the art and include but are not limited to, e.g., NHS ester crosslinkers, thio-cleavable crosslinkers, imidoester crosslinkers, malemide crosslinkers, amine-to-amine crosslinkers, amine-to-sulfhydryl crosslinkers, carboxy-to-amine crosslinkers, photoreactive crosslinkers, sulfhydryl-to-carbohydrate crosslinkers, sulfhydryl-to-hydroxyl crosslinkers, sulfhydryl-to-sulfhydryl crosslinkers, etc.

In some instances, a photoreactive crosslinker may be used to crosslink two macromolecules of the present disclosure or to crosslink one macromolecule to a substrate after an interaction of molecules is detected or after a single molecule phenotype is detected. Any convenient method of activating a photoreactive crosslinker may be employed in instances where crosslinking is desired and may include but is not limited exposing the photoreactive crosslinker to light of an appropriate wavelength, e.g., by positioning a macromolecule containing a photoreactive crosslinker within the field of an activated zero-mode waveguide.

Methods of Tagging Using Polynucleotide Barcodes

The present disclosure provides methods of tagging or barcoding using polynucleotide tags or polynucleotide barcodes and macromolecules with attached polynucleotide tags or barcodes. Attached polynucleotide barcodes, as defined herein, serve to uniquely differentiate individual members or groups of macromolecules. Any method of attachment of a polynucleotide barcode to a macromolecule may find use in the methods described herein.

In some instances, methods of the present disclosure provide methods of attaching a single molecule with a specific single molecule phenotype to the genotype of the specific molecule so that the detected phenotype may be associated with the molecule via its genotype. In some instances, a tag or barcode as described herein provides for the genotype of a particular single molecule. In some instances, a plurality of single molecules are each associated with an individual molecular indicator of their genotype, thus generating a plurality of genotype-associated-single molecules that upon detection of one or more molecules of the plurality having a particular phenotype, the individual genotype associated with the phenotype may be determined.

In certain instances, a polynucleotide barcode is attached to a polynucleotide by a ligation reaction, e.g., a plurality of barcodes is ligated to a plurality of polynucleotides in a single ligation reaction such that each polynucleotide is ligated to at least one unique barcode. In certain instances, a plurality of DNA polynucleotides is ligated to a plurality of DNA barcodes. In certain instances, a plurality of RNA polynucleotides is ligated to a plurality of RNA polynucleotide barcodes. Once uniquely barcoded, copies of individual polynucleotides may be produced by any convenient means, e.g., DNA copies of barcoded RNA polynucleotides are produced by reverse transcription (e.g., RT-PCR), RNA copies of barcoded DNA polynucleotides are produced by transcription, DNA copies of DNA polynucleotides are produced by PCR, etc. In certain instances, a DNA polynucleotide coding sequence (CDS) is ligated, e.g., 3' ligated, to a DNA barcode (e.g., the barcode is ligated to the 3' end of the CDS, e.g., to the 3' UTR). A plurality of polynucleotides may be referred to herein as a "polynucleotide library" and a barcoded plurality of polynucleotides may be referred to herein as a "barcoded polynucleotide library".

In certain embodiments, a barcoded polynucleotide is pre-sequenced or a barcoded polynucleotide library is pre-sequenced, e.g., deep sequenced or sequenced by next-generation sequencing. In certain instances, such pre-sequencing serves to correlate each individual polynucleotide with the bound barcode thus the polynucleotide is further identified in subsequent steps by the sequencing, e.g., re-sequencing, of the barcode. Sequencing technologies, including sequencing technologies involving tags or barcodes, are known to those skilled in the art, e.g., see Harbers & Kahl, *Tag-based Next Generation Sequencing* (John Wiley & Sons) 2012, the disclosure of which is incorporated by reference herein.

In certain embodiments, a barcoded mRNA, e.g., a mRNA with a barcode attached to the 3' end of a 3' UTR, is generated from a barcoded DNA polynucleotide by in vitro transcription. In some instances, an mRNA is ligated to a DNA polynucleotide, e.g., a barcode, by a ligase, e.g., a T4 ligase, e.g., a T4 RNA ligase 2, to generate a DNA/RNA hybrid. In one embodiment, a barcoded mRNA is ligated to a DNA polynucleotide, e.g., to form a hybrid DNA barcode-mRNA fusion. In some instances, a hybrid DNA barcode-mRNA fusion may contain palindromic sequence, e.g., through the end-to-end generation or attachment of identical sequence, thus generating a hybrid palindromic DNA barcode-mRNA fusion. In certain instances a puromycin functionality is incorporated into the ligated RNA/DNA hybrid polynucleotide, e.g., a hybrid palindromic DNA barcode-mRNA fusion that contains a puromycin functionality near an encoded termination site.

In certain embodiments, multiple barcodes, e.g., two barcodes, are ligated to a subject polynucleotide or plurality of polynucleotides. In certain instances barcodes are ligated to each end of polynucleotide. In other embodiments multiple barcodes are ligated to the same end of a polynucleotide. In certain instances, multiple barcodes serve multiple functions, e.g., a first barcode differentiates each member of a plurality of polynucleotides and second barcode differentiates each group of a plurality of groups to which each polynucleotide belongs.

In certain embodiments, a barcoded macromolecule or plurality of barcoded macromolecules is produced by incomplete translation of a barcoded polynucleotide or a plurality of barcoded polynucleotides. According to the methods described herein, a barcoded macromolecule may be generated by in vitro translation, e.g., PURE IVT, from a barcoded polynucleotide as described herein. In certain instances, translation of a barcoded polynucleotide is stalled, thus preventing translation of 3' polynucleotides of the barcoded polynucleotide. In certain instances, stalling of translation prevents the disassociation of the barcoded polynucleotide from a ribosome and a nascent polypeptide, e.g., a polypeptide produced by translation of the 5' end of the barcoded polynucleotide, thus producing a barcoded ribosome-bound polypeptide complex. In certain instances, the IVT used to produce the barcoded macromolecule does not contain or contains an insufficient amount of release factors thus increasing the number of ribosome associated complexes, i.e. ribosome-bound polypeptides.

In some instances, stalling of the translation of a barcoded polynucleotide provides for switching the genetic code by which the barcoded polynucleotide is being translated. For example, in some instances a barcoded polynucleotide being translated according to a first genetic code may be stalled using any of the methods of stalling as described herein and the translation may be re-initiated following stalling with a second genetic code. Any convenient number of stalling events and genetic code switches may find use in methods of generating polynucleotide bound polypeptide of the present disclosure.

In certain instances of the present disclosure, polypeptides or pluralities of polypeptides are barcoded with oligonucleotide barcodes by the direct attachment of a barcode to an amino acid or reactive side-chain of an amino acid through a biochemical reaction. In certain instances, the attachment of a barcode to a polypeptide is indirect, e.g., requiring an intermediate linker with reactive groups used to link the polypeptide and a barcode. Examples of such linkers include but are not limited to: amino acid linkers, unnatural amino acid linkers, oligonucleotide linkers, nanoparticle linkers, biopolymer linkers, and the like. In one embodiment, such a linker may be a puromycin linker or a linker that is a puromycin derivative or a puromycin analog, including but not limited to, e.g., dC-puromycin conjugates, O-Propargyl-puromycin, Biotin-dC-puromycin, 6-FAM-dC-puromycin, and the like.

As an alternative to biochemical linking of a barcode to a polypeptide, in some instances, a barcode is chemically conjugated to a polypeptide by any convenient method, e.g., post-synthetic conjugation (e.g., post-assembly conjugation or fragment coupling strategy), total stepwise synthesis (e.g., on-line solid phase synthesis), native ligation, template-directed ligation, carbodiimide chemistry, maleimido/thiol chemistry, hydrazinonicotinamide chemistry, and the like. In certain instances, conjugating a barcode to a polypeptide is achieved through the use of synthetic nucleoside derivatives or synthetic amino acid derivatives, e.g., unnatural amino acids. For example, in some embodiments a reactive group on an UAA, e.g., an azide or alkyne reactive group, incorporated into a polypeptide is utilized in a chemical reaction, e.g., a cycloaddition reaction, to attach a barcode to a polypeptide. Methods of peptide-to-nucleoside conjugation and conjugation by synthesis are known in the art, see, e.g., Gogoi et al. (2007) *Nucleic Acids Research*, e139; and Williams & Chaput (2010) *Curr. Protoc. Nucleic Acid Chem.*; the disclosures of which are incorporated by reference herein.

The present disclosure provides methods for utilizing a polynucleotide barcode attached to a macromolecule or a plurality of polynucleotide barcodes attached to a plurality of macromolecules to identify a macromolecule by sequencing the attached barcode, e.g., by single-molecule direct sequencing. Methods of single-molecule direct sequencing applicable to identification of macromolecules with attached polynucleotide barcodes include, e.g., sequencing by synthesis methods and optical sequencing methods, see, e.g., Thompson & Milos (2011) *Genome Biology*, 217, the disclosure of which is incorporated by reference herein. In certain instances, a barcoded macromolecule is attached to a substrate compatible with single molecule direct sequencing, e.g., an optically clear surface (e.g., a glass surface or a quartz surface) or an optical waveguide (e.g., a zero-mode waveguide). Such substrates compatible with single molecule direct sequencing represent substrates capable of limiting illumination or excitation of a fluorescent molecule to a single addressable unit. Non-limiting examples of such substrates are substrates capable of being used in conjunction with total internal reflectance fluorescence (TIRF) or Förester resonance energy transfer (FRET). In certain instances, a barcoded macromolecule is attached, e.g., directly attached, to a substrate, e.g., a surface, e.g., a glass surface, e.g., a flow cell, compatible with TIRF such that single molecule-direct sequencing is used to determine the sequence of the attached barcode. In certain instances, a barcoded macromolecule is attached, e.g., indirectly attached, to a substrate, e.g., a surface, e.g., a glass surface, e.g., a flow cell, compatible with TIRF such that single molecule-direct sequencing is used to determine the sequence of the attached barcode. In certain instances, a barcoded macromolecule is attached, e.g., directly attached, to a substrate, e.g., a zero-mode waveguide, compatible with single-molecule direct sequencing such that single-molecule direct sequencing is used to determine the sequence of the attached barcode. In certain instances, a barcoded macromolecule is attached, e.g., indirectly attached, to a substrate, e.g., a zero-mode waveguide, compatible with single-molecule direct sequencing such that single-molecule direct sequencing is used to determine the sequence of the attached barcode. In some instances macromolecules, e.g., polypeptides, are made synthetically on the compatible substrate itself, e.g., through combinatorial solid-phase synthesis methods, or e.g., through IVT with an immobilized or bound ribosome. For example, in some instances a polynucleotide-bound polypeptide, e.g., a ribosome-nascent chain or a mRNA-polypeptide complex, may be tagged, e.g., through conjugation chemistry, with an immobilization moiety capable of being used to immobilize the polynucleotide-bound polypeptide to a substrate, e.g., for single molecule screening. Method of attachment, e.g., direct attachment, e.g., indirect attachment, of macromolecules to substrates compatible with single-molecule direct sequencing and method of single molecule direct sequencing are known in the art, see, e.g., PCT publication WO 2010/144150, U.S. Pat. No. 8,609,421, PCT publication WO 2007/075873, and PCT publication WO 2009/145818, the disclosures of which are incorporated by reference herein.

Kits

The present disclosure provides kits suitable for practicing the methods of the present disclosure, e.g., for use in generating readily modified or modified polypeptides. In some instances, kits at least include an amount of a reagent for carrying out a cell free in vitro translation reaction with an unnatural amino acid that contains a reactive group and an amount of a reagent for performing a cycloaddition reaction for the attachment of a heterologous moiety to the reactive group on the unnatural amino acid. In some instances, a readily modifiable polypeptide is a polypeptide with an incorporated unnatural amino acid that comprises a reactive group useful in a cycloaddition reaction, e.g., an azide group. According to other embodiments, the reactive group may comprise an alkyne reactive group useful in a cycloaddition reaction. Commonly used cycloaddition reactions that find use in kits of the present invention are disclosed elsewhere herein but briefly include but are not limited to copper-catalyzed cycloaddition, ligand-assisted copper catalyzed cycloaddition, copper-free cycloaddition, and the like. Examples of ligands useful in ligand-assisted copper catalyzed cycloaddition reaction are known in the art, and include but are not limited to, e.g., 3-[4-({bis [(1-tert-butyl-1H-1,2,3-triazol-4-yl)methyl]amino}methyl)-1H-1,2, 3-triazol-1-yl]propanol (BTTP) and 3-[4-({bis[(1-tert-butyl-1H-1,2,3-triazol-4-yl)methyl]amino}methyl)-1H-1,2,3-triazol-1-yl]propyl hydrogen sulfate (BTTPS), which are described by Wang et al. (2011) *Chem. Asian J.* 6:2796-2802, the disclosure of which is incorporated herein by reference.

In addition to the above components, the subject kits may further include the heterologous moiety that is attached via cycloaddition. Any desired heterologous moiety with compatible chemistry, or desired molecule modified to be compatible, may be utilized. In certain instances heterologous moieties compatible with a cycloaddition reaction comprise a reactive group, e.g., an azide or an alkyne reactive group. In certain instances, a heterologous moiety may be a fluorescent molecule, e.g., a fluorescent small molecule or a fluorescent protein, compatible with fluorescent microscopy or advanced fluorescent imaging techniques, e.g., FRET or BRET. In other embodiments, the heterologous moiety contains a linker for further chemical reactions, e.g., addition of at least one additional moiety by a chemical reaction other than a cycloaddition, e.g., a cross-linker moiety.

In addition to the above components, the subject kits may further include master mixes and/or sub-component master mixes. Such master mixes may include concentrated components, present either singly or in combination with related components for ease of storage or ease of performance of methods of the invention disclosed herein. In particular preferred embodiments, master mixes of the present kits include but are not limited to initiation/elongation factor mixes (e.g., concentrated to about 5 to 50 times the preferred reaction concentration, including but not limited to 5 times, 10 times, 20 times, 25 times, 30, times, 40 times or 50 times the preferred reaction concentration), release/recycling factor mix (e.g., concentrated to about 5 to 50 times the preferred reaction concentration, including but not limited to 5 times, 10 times, 20 times, 25 times, 30, times, 40 times or 50 times the preferred reaction concentration), aaRS/other mix (e.g., concentrated to about 5 to 50 times the preferred reaction concentration, including but not limited to 5 times, 10 times, 20 times, 25 times, 30, times, 40 times or 50 times the preferred reaction concentration), and amino acid/NTP/creatine phosphate mix (e.g., concentrated to about 1 to 6 times the preferred concentration including but not limited to about 5 times, about 6 times, about 5.5 times, about 5.6 times, etc. the preferred reaction concentration).

In addition to the above components, the subject kits of the present disclosure may also include an amount of a reagent for carrying out an in vitro transcription reaction. In certain embodiments, such reagents for carrying out in vitro transcription are used to generate a mRNA template from which in vitro translation is performed. Reagents for carrying out in vitro transcription for use in the methods described herein include those that are well known in the art, including as non-limiting examples, those commercially available from Life Technologies (e.g., MAXIscript), New England Biolabs (e.g., RNA Synthesis kits), Thermo Scientific (e.g., TranscriptAid).

In addition to the above components, the subject kits of the present disclosure may also include an amount of a recombinant vector useful in cloning and altering a subject polynucleotide subsequently used in in vitro transcription and in vitro translation reactions in accordance with herein described embodiments of the subject kits. In certain instances, a vector included in the subject kits comprises a polynucleotide sequence that encodes for a ribosome stalling element. Ribosome stalling elements, e.g., ribosome stalling sequences, are well known in the art, see, e.g., Peil et al. (2013) *PNAS*, 15265-70, Tanner et al. (2009) *J Biol Chem*, 34809-18, Woolstenhulme et al. (2013) *PNAS*, E878-87, and Spevak et al. (2010) *J Biol Chem*, 40933-42, the complete disclosures of which are incorporated herein by reference. In some instances, a vector comprises a polynucleotide sequence that codes for the ribosome stalling sequence represented by a polypeptide with at least 90% sequence identity to FSTPVWISQAQGIRAGPQ (SEQ ID NO:2). In certain embodiments, the vector also includes at least one regulatory element, e.g., a stem-loop element; an epsilon enhancer element; and a ribosome-binding site element, and the like.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), etc., on which the information has been recorded. Yet another form of these instructions that may be present is a website address which may be used via the internet to access the information at a removed site.

Libraries and Screening

The present disclosure provides polynucleotide and polypeptide libraries and methods of screening for molecular phenotypes, e.g., single molecule phenotypes, in the polypeptides of a polypeptide library or the polypeptides produced from a polynucleotide library. A polypeptide or polynucleotide library may represent any related or unrelated plurality of polypeptides or polynucleotides. As non-limiting examples, a library may represent a plurality of polypeptide drug candidates or a plurality of polynucleotides encoding for a plurality of polypeptide drug candidates, e.g., possessed by a particular entity. In other instances, a library may represent mutants of a particular polypeptide generated by mutagenesis of a parent molecule. As described in certain embodiments herein, a library may be barcoded with polynucleotide barcodes and sequenced to as to produce a listing, e.g., a database containing a listing, of barcodes correlated with each particular member of the library. In certain instances, libraries may also be generated from collected and isolated naturally occurring polynucleotide sequences. In yet other embodiments, libraries may comprise a plurality of synthetically generated polynucleotides or polypeptides, e.g., synthetically generated polynucleotide or polypeptide based on rational design which may be based on a chemical or physical structure or model of a target or parent molecule.

The present disclosure also provides for methods of screening libraries, e.g., analyzing libraries in order to detect a desirable molecular phenotype. Methods of screening libraries and desirable phenotypes applicable to particular fields will be readily apparent to those skilled in the art in each particular field. In some embodiments, phenotypes are detected through the microscopic or spectroscopic detection of a fluorescent molecule, e.g., detection of fluorescence of a particular wavelength, detection of fluorescence of a particular intensity, detection of fluorescence in a particular area or region, and the like. In certain instances, detected fluorescence may be derived from a fluorescent small molecule or a fluorescent protein. In particular preferred embodiments, desirable molecular phenotypes, e.g., particular polypeptide molecular conformations or structural characteristics, are detected by the interaction of closely oriented chromophores, e.g., resonance energy transfer (RET). In certain embodiments, a phenotype is detected through the use of FRET. In certain instances, FRET is performed through the interaction of two variants of green fluorescent protein, e.g., cyan fluorescent protein and yellow fluorescent protein. In other instances, FRET is performed through the interaction of two of the same fluorescent molecules, e.g., by Homo-FRET. In yet other instances, phenotype detection is through the detection of bioluminescence, e.g., BRET. Any convenient method of the detection of single molecules known in the art may be utilized, non-limiting examples of which include: detection of radioactive molecules (e.g., radio-labels), detection of small particle labeling (e.g., gold, silver, or other nanoparticle labels), enzymatic labeling, and the like.

The present disclosure provides methods for the molecular evolution, e.g., directed evolution, of subject molecules through the repeated screening and evolution of a library. According to particular embodiments of the present disclosure, a polynucleotide library, e.g., a plurality of mutants of a particular subject molecule, may be screened to detect a molecule displaying a particular desired phenotype and mutants of the detected molecule may be produced for subsequent rounds of screening. Iterative rounds of screening, selection, and mutation generate molecules with increased or strengthened expression of a selected phenotype. One skilled in the art will recognize that the number of rounds useful for molecular evolution will depend on the particular desired phenotype and the particular molecules being screened. In certain embodiments, molecular evolution of a molecule is performed using reverse transcription of a polynucleotide found to encode for a polypeptide with a desirable phenotype. In other embodiments of the present disclosure, a molecule with a detected desirable phenotype, e.g., a polypeptide, is correlated with a polynucleotide copy of the molecule through the sequencing of a polynucleotide barcode, e.g., by comparison of a barcode sequence to a reference set of full length sequences that are correlated with unique barcodes, and the polynucleotide copy is subsequently amplified and/or mutated to generate a new library for an additional round of evolution and screening. General principles of methods of directed molecular evolution are known in the art, see, e.g., Cobb et al. (2012) *Curr Opin Chem Biol*, 285-91 and Bloom & Arnold (2009) *PNAS*, 9995-10000, the disclosures of which are incorporated by reference herein.

Utility

Methods, kits, and polynucleotide and polypeptide libraries of the present disclosure find use in research applications and in diagnostic applications, which are described below.

Methods of the present disclosure are useful in single molecule studies including but not limited to single molecule studies of cytotoxic, protease-sensitive, intrinsically disordered, or aggregation-prone proteins which are often difficult to express, purify, and label using traditional methods.

Methods of the present disclosure are also useful in a number of applications where the combination of high-throughput protein sample generation and single molecule fluorescence detection has the potential to yield unique biological insights or capabilities. For example, the methods of the present disclosure are useful in the detection of desirable single molecule phenotypes from large libraries and/or the molecular evolution of desirable single molecule phenotypes.

Methods of the present disclosure for site-specific UAA incorporation strategies and subsequent cycloaddition mediated labeling are useful for single molecule FRET studies of proteins and RNCs previously generated in eukaryotic and/or mammalian extract-based IVT systems and live cell systems. The methods of the present disclosure provide for robust and/or quantitative site-specific UAA incorporation that increases the quality and/or throughput of single-molecule studies including the detection and/or directed molecular evolution of desired single molecule phenotypes.

Kits of the present disclosure are useful in research, industrial, and laboratory applications for the generation of readily modified polypeptides that, when modified, can be analyzed at the single molecule level.

Polypeptide and polynucleotide libraries of the present disclosure are useful in research, industrial, and laboratory applications for the rapid screening of intramolecular and intermolecular interactions and phenotypes which, when selected, can be further subjected to directed evolution to produce macromolecules with preferred characteristics.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Purified and Reconstituted In-vitro Translation System Components

Cloning: *E. coli* translation factors, aminoacyl-tRNA synthetases (aaRSs), adenylate kinase (AK), nucleotide diphosphate kinase (NDK), and methionine transformylase (MTF) were each PCR amplified from *E. coli* MG1655 genomic DNA (A.T.C.C.) and LIC-cloned into the ampicillin-resistant plasmids pET-His6-TEV-LIC-(2B-T) (www(dot)addgene(dot)org) and pJL-H6 yielding, respectively, N-terminal 6×His-TEV-tagged and C-terminal 6×His-tagged expression constructs. In the case of the multi-subunit synthetases, PheRS and GlyRS, the alpha and beta subunits were tagged respectively. Untagged EF-Ts was also cloned into a kanamycin-resistant variant of pJL-H6 for co-expression with tagged EF-Tu.

Protein Expression: Transformed BL21-Star(DE3) cells were grown to an OD of 0.5-0.9 in 1 L Luria-Bertani (LB) broth. Isopropyl-β-D-thiogalactoside (IPTG) was added to a final concentration of 0.1 mM, and cells were grown for an additional 4-8 hrs at 37° C. (48 hrs at 22° C. for EF-Tu/EF-Ts co-expression, and 4 hrs at 22° C. for ArgRS). Induced cell pellets were harvested, flash-frozen in liquid nitrogen, and stored at −80° C. until ready for purification.

Component Purifications: For the various purification buffers: 1 μM ATP was added for all aaRSs; 10 μM ZnCl was added for aaRSs which require zinc as a co-factor; 50 μM GDP was added for EF-G, EF-Tu/EF-Ts, IF-2, and RF-3; and the EF-Tu/EF-Ts purification buffers lacked $Mg^{2+}$ ions. N-terminally his-tagged T7 RNA polymerase was also purified using established affinity and ion exchange chromatography. Apart from these excepts, stored cell pellets were resuspended in ice-cold lysis buffer [50 mM HEPES-KOH (pH 7.6), 1 M NH4Cl, 10 mM MgCl2, 0.3 mg/mL lysozyme, 0.1% Triton X-100, 1× protease inhibitors, and 7 mM β-mercaptoethanol (BME)], incubated at 4° C. for 30 min to generate spheroplasts, lysed by sonication (3 minutes at 15 W, 10 sec on 10 sec off), and clarified by centrifugation at 18,000 g for 30 min at 4° C. Supernatants were then applied to $Ni^{2+}$-precharged 5 mL HisTrap HP columns, washed with 30-50 mL wash buffer [50 mM HEPES-KOH (pH 7.6), 1 M NH4Cl, 10 mM MgCl2, and 7 mM BME, 20 mM imidazole], and eluted with a linear gradient of 20 mM to 400 mM imidazole. Fractions containing the desired proteins were concentrated, applied onto a pre-equilibrated HiPrep 16/60 Sephacryl S-200 or S300 HR size exclusion column (GE Healthcare), eluted into storage buffer [50 mM HEPES-KOH (pH 7.6), 100 mM KCl, 10 mM MgCl2, 30% glycerol, and 7 mM BME], reconcentrated, quantified, aliquoted, flash-frozen, and stored at −80° C. MRE600 (untagged) and JE28 (His-tagged L12) ribosomes were purified without the removal of protein S1.

Additional Components: Rabbit muscle creatine kinase (Roche) and *E. coli* inorganic pyrophosphatase (Sigma) were dissolved in storage buffer [50 mM HEPES/KOH (pH 7.6), 100 mM KCl, 10 mM MgCl2, 7 mM BME, 30% Glycerol], aliquoted, flash frozen, and stored at −80° C. *E. coli* MRE600 tRNA (Roche) was dissolved in tRNA storage buffer [10 mM KOAc, 2 mM MgOAc, (pH 4.5)], aliquoted, flash frozen, and stored at −80° C. Acid-stabilized 5,10-methenyl-THF (m-THF) formyl-donor precursor was synthesized from folinic acid (Sigma) and converted to active 10-formyl-THF (f-THF) prior to each IVT reaction. Stocks of amino acids, NTPs, and creatine phosphate (Sigma) were dissolved in 50 mM HEPES-KOH (pH 7) (10 mM BME was added for cysteine and methionine stocks), neutralized, and flash frozen before storage at −80° C.

Aminoacyl-tRNA synthetase activity assays: The initial aminoacylation rates of 18 purified aaRSs (all except cysteinyl-RS and asparaginyl-RS) were each determined using $^3$H or $^{14}$C-labeled amino acid (Moravek Biochemicals, Inc) charging assays followed by TCA precipitation and quantification by liquid scintillation counting. The aaRS activity loss upon successive rounds of freeze-thawing and the pmols of amino-acid specific tRNA acceptor activity per $A_{260}$ unit of bulk E. coli tRNA were determined similarly. Assay conditions included 50 mM HEPES-KOH (pH 7.6), 100 mM KOAc, 13 mM Mg(OAc)$_2$, 10 mM ATP, 1 mM DTT, 2 mM spermidine, 0.01% Tween-20 or 1 mg/mL BSA, and saturating concentrations of tRNA and amino acid substrates (typically 2.5-10 times the reported $K_m$ values). 1 Unit of activity is defined as the amount of enzyme that catalyzes the formation of 1 pmol of aa-tRNA per minute at 37° C.

Component concentrations and master mixes: The final component concentrations and/or activities in the reconstituted PURE WT system are given in Table 1 (FIG. 5). To facilitate the routine use of the home-made PURE IVT system the various translation components were divided into four sub-component master mixes: initiation/elongation factor mix (50×), release/recycling factor mix (50×), aaRS/other mix (50×), and amino acid/NTP/creatine phosphate mix (5.6×). Ribosomes, tRNA, T7 RNA polymerase, formyl-donor, and other small-molecule additives—including buffering agent, salts, polyamines, and Tween-20 detergent—were added separately.

DNA and mRNA templates for IVT reactions: Genes for T4 Lysozyme (T4L) and Barnase were subcloned into pET-LIC-(2A-T) (www(dot)addgene(dot)org) which contained the 17-residue secM stalling sequence (FSTPVWISQAQGIRAGPQ) (SEQ ID NO:2) fused in-frame to the C-terminus of each coding sequence. The wild-type T4L construct (wt*-M) contained the following mutations relative to the native sequence: C54T and C97A (to remove native cysteines), and M6L, M102L, M106L, and M120L (to remove native internal methionines). Barnase does not contain any native cysteine or internal methionine residues. The catalytically inactive H102A Barnase mutant was used to avoid Rnase-induced translation inhibition. Linearized DNA templates were generated via two-step nested PCR enabling the addition of regulatory 5'-UTR elements—including a stable 5'-mRNA hairpin structure (GGGAGACCACAACGGUUUCCC) (SEQ ID NO:3), the epsilon enhancer element (UUAACUUUA), and a strong ribosome-binding site (AGAAGGAGA). PCR products were ethanol precipitated, resuspended in RNase-free 10 mM Tris-HCl (pH 7.6), quantified, and diluted to 4 µM before storage at −20° C. mRNA templates were generated from these DNA templates using T7 RNA polymerase in vitro transcription protocols. mRNAs were then ethanol precipitated, quantified, and diluted to 20 µM in mRNA storage buffer (10 mM KOAc (pH 4.5) prior to flash-freezing and storage at −80° C.

Home-made PURE IVT Reactions

The final optimized concentrations of all PURE IVT components are given in Table 1 (FIG. 5). A spreadsheet was used to keep track of the salt, reducing agent, glycerol, and EDTA contributions of all stock solutions to the final reaction conditions. Prior to each PURE IVT reaction, m-THF was converted to f-THF by neutralizing the 21 mM m-THF stock with 0.1 M KOH and 125 mM Tris-HOAc (pH 7.8) in a 1:1:8 ratio for 15 minutes at RT. The 70S ribosome stock was also heat reactivated at 40° C. for 10 minutes in the presence of 20 mM Mg(OAc)$_2$ and 200 mM NH$_4$OAc and then quenched on ice. The following components were added to a master mix in this order: RNase-free water, Tris-HOAc (pH 7.6), NH$_4$OAc, Mg(OAc)$_2$, spermidine, putrescine, ZnSO$_4$, BME/DTT, and Tween-20. The sub-component master mixes (amino acid mix, aaRS mix, factor mix, and—for multi-turnover reactions—release factor mix) were then thawed on ice and added to the pre-chilled master mix. Finally, tRNAs, ribosomes, UAAs/Met, and (for DNA-programmed reactions) T7 RNA polymerase were added. For mRNA-templated reactions mRNAs were heat-denatured at 65° C. for 3 minutes and then quenched on ice before their addition to the IVT master mix to initiate translation. Reactions were placed in a dry, dark, 37° C. incubator for 45 min or 2 hrs to generate single-turnover stalled RNCs or multi-turnover released protein products, respectively. Since properly SecM-stalled RNCs are puromycin insensitive, prematurely-stalled RNC products due to polysome formation could be eliminated by a 5 min, 37° C., 1 mM puromycin treatment following all single-turnover IVTs.

Commercial PURE IVT Reactions

Commercial PURExpress A(aa, tRNA) IVT kit (New England Biolabs) reactions were set up as directed, with minor modifications. The reactions included pre-synthesized mRNAs rather than DNA templates and an amino acid mix which, when diluted to its final working concentration, yielded 0.3 mM of each amino acid (except methionine) and 0.3 mM HPG.

PURE IVT Sample Processing Protocols

For liquid chromatography-mass spectrometry (LC-MS): 125 µL-scale PURE IVT reactions were set up as described above using an all-natural amino acid mix and programmed with either a linear DNA template encoding T4L wt*-M D61M D159C-secM or no added DNA template. Reactions were quenched on ice and 400 µL ice-cold RNC stabilization buffer [20 mM Bicine (pH 7.0), 50 mM Mg(OAc)$_2$, 75 mM NH$_4$OAc, 120 mM KOAc, 0.05% Tween-20] with 1 mM TCEP was added. Most IVT components were washed away from the desired RNC product via repeated washing (3×10 minutes) with additional RNC stabilization buffer on a 100 kDa Amicon ultrafiltration device (Millipore). The final concentrated sample (~30 µL) was treated with RNase A/EDTA and subjected to SDS PAGE on a 12% BisTris-MES gel to resolve most ribosomal proteins from the T4L nascent chain product. The product band—visible only in the templated reaction following coomasie brilliant blue staining—was excised from the gel, trypsin-digested using standard protocols and submitted for LC-MS analysis.

For Radioactive $^{14}$C-Phe incorporation: 25-50 µL PURE IVT reactions were set up as described except that 50 µm 14C-Phe (100 Ci/mol) was used instead of 0.3 mM non-radioactive Phe. Following each IVT reaction, $^{14}$C-Phe-tRNAs and peptidyl-tRNAs were optionally degraded using RNase A/EDTA and samples were then subjected to SDS PAGE on a 12% Bis-Tris-MES gel followed by exposure to a storage phosphor screen and autoradiographic imaging on a STORM 840 phosphorimager (Molecular Dynamics). IVT samples were also RNaseA/EDTA-treated, TCA precipitated, and acid-insoluble (i.e. proteinacious) radioactivity was quantified by liquid scintillation counting on a Tri-Carb 2700TR (Packard/Perkin Elmer).

For Fluorescence labeling: 25-50 µL PURE IVT reactions were set up as described with 0.3 mM HPG in place of methionine. For stalled RNC products, 1 vol. ice-cold 2×RNC stabilization buffer was added and RNCs were pelleted away from other IVT components via ultracentrifugation for 75 min at 90 krpm across a 70 uL 1M sucrose cushion on a TLA-100 rotor (Beckman Coulter). Pellets were then washed once with additional RNC stabilization buffer to remove any residual BME. For non-stalled/multi-turnover IVT reactions, HPG-tagged proteins were separated from unincorporated HPG using a Micro Bio-Spin P6 size-exclusion column (Bio-Rad) as per the manufacturer's instructions. Further purification of HPG-tagged proteins away from ribosomes and His-tagged translation factors was achieved using a 30 kDa Amicon ultrafiltration device (Millipore) followed by reverse Ni:NTA purification of any remaining His-tagged translation factors away from HPG-tagged protein samples. HPG-tagged RNC pellets or aqueous protein samples were then labeled anaerobically using the CuAAC reaction.

Liquid Chromatography-Mass Spectrometry (LC-MS)

Trypsin-digested peptides were analyzed using an ultra-performance liquid chromatograph (nanoAcquity UPLC, Waters, Milford, Mass.) that was connected in-line with a quadrupole time-of-flight mass spectrometer equipped with a nanoelectrospray ionization (nanoESI) source (Q-Tof Premier, Waters). The UPLC was equipped with $C_{18}$ trapping (20 mm×180 µm, 5 µm particles, Waters Symmetry) and analytical (100 mm×100 µm, 1.7 µm particles, Waters BEH130) columns and a 10 µL sample loop. Solvent A was 99.9% ultrapure water/0.1% formic acid and solvent B was 99.9% acetonitrile/0.1% formic acid (v/v). Following sample injection, trapping was performed for 5 min with 100% A at a flow rate of 3 µL/min. The elution program consisted of a linear gradient from 5% to 35% B over 60 min, a linear gradient to 95% B over 0.33 min, isocratic conditions at 95% B for 5.67 min, a linear gradient to 1% B over 0.33 min, and isocratic conditions at 1% B for 14.67 min, at a flow rate of 500 nL/min. The analytical column and sample compartment were maintained at 35° C. and 8° C., respectively. The column exit was connected to a Universal NanoFlow nanoESI emitter mounted in the ion source of the Q-Tof Premier. External mass calibration was performed prior to analysis. Mass spectra were acquired in the positive ion mode and were processed using MassLynx software (version 4.1, Waters).

Optimized Copper(I)-catalyzed Azide-alkyne Cycloaddition (CuAAC) Reaction

HPG-tagged and purified proteins or RNC pellets together with Alexa488-azide, Alexa647-azide (Life Technologies, Inc), or Atto647N-azide (ATTO-TEC GmbH) dye stocks (100-200 µM) were brought into a vinyl anaerobic (<10 ppm $O_2$) chamber (Coy Laboratory Products). RNC pellets were gently dissolved in RNC stabilization buffer to a ribosome concentration of ~1.2 µM (~0.4-0.8 µM RNCs). Donor and acceptor azido-dye conjugates were added to a final total concentration of 5-10 µM (~10-20 fold excess over RNCs). Samples were then deoxygenated for ~1 hr. To initiate the CuAAC reaction, equal volumes of 10 mM $CuSO_4$ and (for BTTES and BTTP) 20 mM ligand were mixed together and then added to the deoxygenated samples to a final concentration of 0.5 mM copper. Finally, a pre-weighed and anaerobically-stored dry aliquot of ascorbic acid was dissolved in $ddH_2O$ to 10 mM and then added to a final concentration of 1 mM to initiate the reaction. After 1-2 hours, 1 µL of the reaction containing a total of ~5-10 pmols of dyes was removed and saved as a control for in-gel fluorescence quantification of the labeling efficiency. The rest of the reaction was brought up to ~30 µL with RNC stabilization buffer. Unreacted free dyes, copper, ascorbate, and ligand were then removed using a Micro Bio-Spin P6 size-exclusion column (Bio-Rad) as per the manufacturer's instructions. An $A_{260}$ measurement was subsequently taken to ensure the efficient recovery of ribosomes during sample processing (generally >80% from IVT to final labeled RNC sample).

In-gel Fluorescence Quantification of Dye Labeling Efficiency

All three dye-conjugates used in the present study migrate near the dye front in the BisTris-MES (pH, 6.5) SDS PAGE gel system used. The intensities of dye samples treated with Cu and ascorbate were identical to untreated dye samples indicating that the combination of these reagents does not irreversibly affect dye fluorescence intensities. The degree of labeling in a given sample was quantified by normalizing product band intensities by the integrated intensities from defined quantities of each free-dye. The analysis assumes that the quantum yields of the free unreacted dye and the dye-labeled peptide or peptidyl-tRNA within the gel environment are identical.

Labeled RNC samples and free-dye quantification controls were loaded onto 12% BisTris-MES (pH 6.5) gels, separated by SDS-PAGE, detected using a Typhoon Trio gel scanner (GE Healthcare), and the pmols of dye within each sample band was calculated using ImageQuant TL software (GE Healthcare) together with the known amounts and integrated intensities of the free-dye bands in the quantification controls samples.

Diffusion-Based Single Molecule FRET with Alternating Laser Excitation (smFRET-ALEX)

Figure 10:
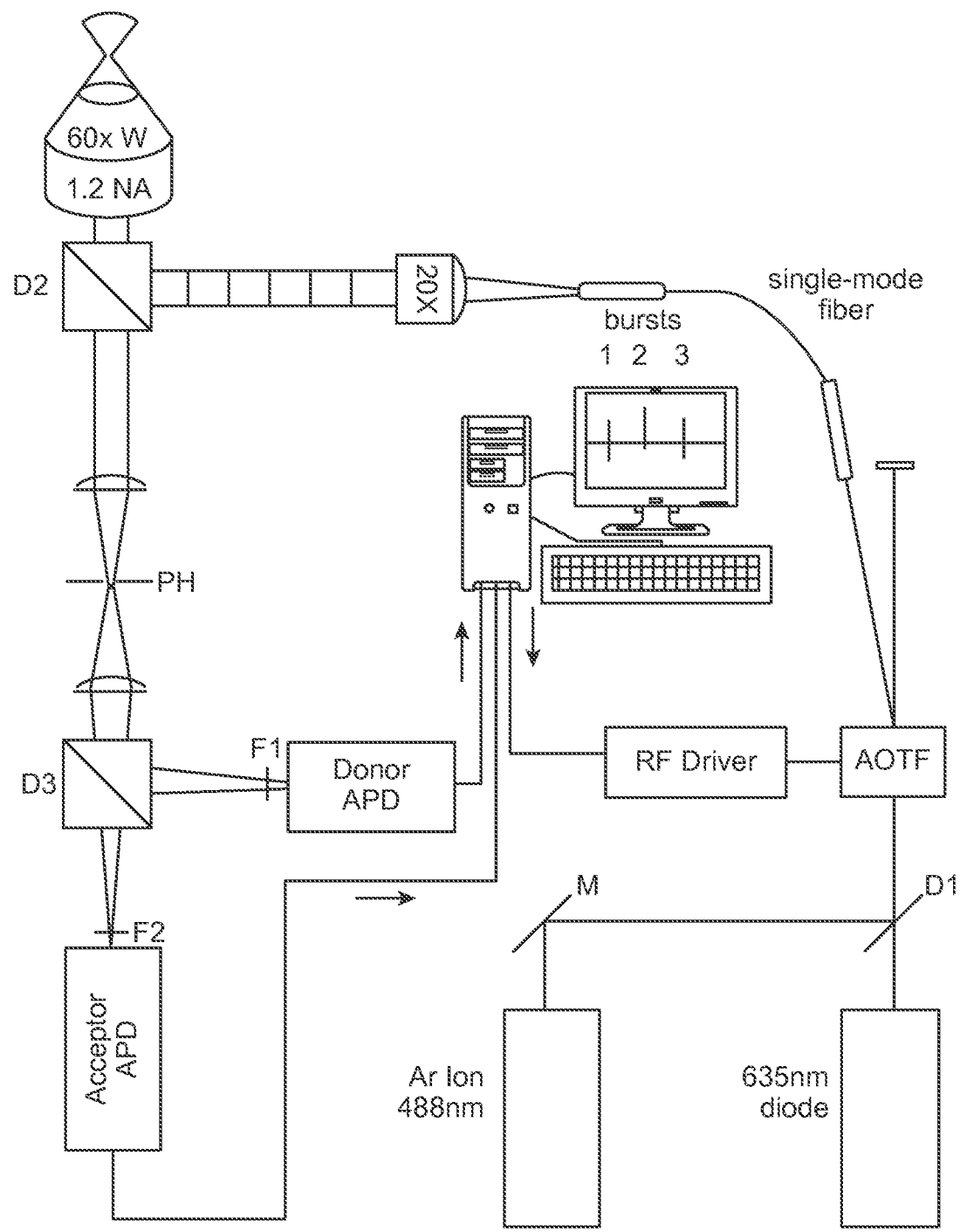
FIG. 10 depicts a schematic of the sm-FRET-ALEX instrumentation, showing the diffusion-based confocal microscope with alternating laser excitation capabilities, the acousto-optic tunable filter (AOTF), the dichroic (D), the filter (F), the mirror (M), the avalanche photo-diode (APD), and the pinhole (PH).

FIG. 10 illustrates the basic elements of the smFRET-ALEX microscope that was custom-built for the present study. The 488-nm line of an argon ion laser (Midwest Laser Products) and a 635-nm diode laser (Coherent) were combined using a 600 dcxr dichroic minor (D1, Chroma). The combined beams were passed through an acousto-optic tunable filter (AOTF, Neos Technologies) to enable microsecond (rise times of ~2-3 µs) alternating laser excitation (µsALEX). The deflected beams were coupled into an appropriately-positioned single-mode fiber (Thor Labs), the output of which was collimated, reflected off of an immobilized high-quality z488/543/633rpc triple-band polychroic minor (D2, Chroma Corp.) and underfilled (β~3) into the back aperture of an infinity-corrected PSF-grade UplanS apochromat 60×1.2 NA water-immersion objective (Olympus America) thereby defining the multiple (donor and acceptor direct) excitation volumes of the smFRET-ALEX microscope system. The objective was mounted onto a custom-made ultra-stable microscope body such that realignment of the excitation beam path from the fiber launcher into the objective was not required for up to 6 months at a time. The input laser powers during single molecule data acquisition (typically 5-15 minutes per sample) were ~40-50 µW for the 488 nm line and 12-15 µW for the 635 nm line. Emitted bursts of fluorescence from freely diffusing species were collected in epi-fluorescence mode, focused onto a 100 µm pinhole (PH), collimated, spectrally separated into donor and acceptor emission paths using a 630 dcxr dichroic (D3, Chroma), and refocused onto the active areas of two avalanche photodiode (APD) detectors (Perkin Elmer Optoelectronics). The voltage spikes resulting from each single photon detection event were relayed onto the gates of a PCI-6602 counter-timing board (National Instruments) enabling 12.5 nsec resolution time-stamping of each photon detection event using the EnLighten single molecule data acquisition and analysis software suite. The same software and counter timer board was also used to send control signals to the AOTF driver and alternate at a 25 µsec periodicity between the donor and acceptor excitation beams. Finally, a 3-axis nanopositioning sample scanning stage (Mad City Labs) enabled bead-scanning point spread function imaging measurements which directly quantify the degree of overlap between the multiple excitation and detection volumes. For smFRET-ALEX data acquisition, samples were typically diluted to approximately 100 pM ribosomes in RNC stabilization buffer containing 5 mM $Mg^{2+}$ and data was acquired for 10-15 minutes per sample. No oxygen scavengers or coupled reducing and oxidizing system reagents were required in the present study due to the robust photophysical properties of Atto647N.

Data analysis consisted of first defining the donor and acceptor laser excitation windows of the alternation cycle. Next, a sliding-photon window burst search algorithm was applied to the sum of all photons detected within either the donor or acceptor laser excitation windows of the alternation period. This burst search was defined using the following parameters: a 10 kHz total count rate (i.e. a 0.2 ms interphoton time delay) sustained for at least 30 consecutive photons.

E. Coli In-vitro Translation System Purification, Reconstitution, and Validation A fully-customizable PURE WT system was developed in order to exert maximal control over both protein synthesis and the local folding environment of a nascent polypeptide chain. Each protein component was cloned, expressed, and purified using affinity and size-exclusion chromatography. Translation elongation factor EF-Tu was co-expressed and purified as a complex with EF-Ts. RNase-free 70S ribosomes were isolated according to established protocols with minor modifications. In addition, the activities of 18 out of the 20 purified aminoacyl-tRNA synthetase (aaRS) enzymes were quantified in separate amino-acid charging assays. Table 1 (FIG. 5) lists the final concentrations and (where determined) activities of each component in the customized E. coli PURE WT system used here.

Barnase, a 110-residue ribonuclease, and variants of T4 lysozyme (T4L), a 164-residue glycosyl hydrolase were used as model systems. Stalled RNC complexes were generated using the 17-residue secM stalling sequence. For a typical IVT reaction, translation-component stocks were thawed on ice, mixed together, programmed using either DNA or mRNA templates, and placed in a 37° C. incubator for either 45 min for single-turnover stalled RNC products or 2 hours for multi-turnover released protein products (FIG. 1). Following translation, samples were processed depending on the sample type (single vs. multi-turnover) as well as the intended downstream application: radioactivity assays, mass spectroscopic analysis, in-gel fluorescence, or smFRET.

Figure 2:
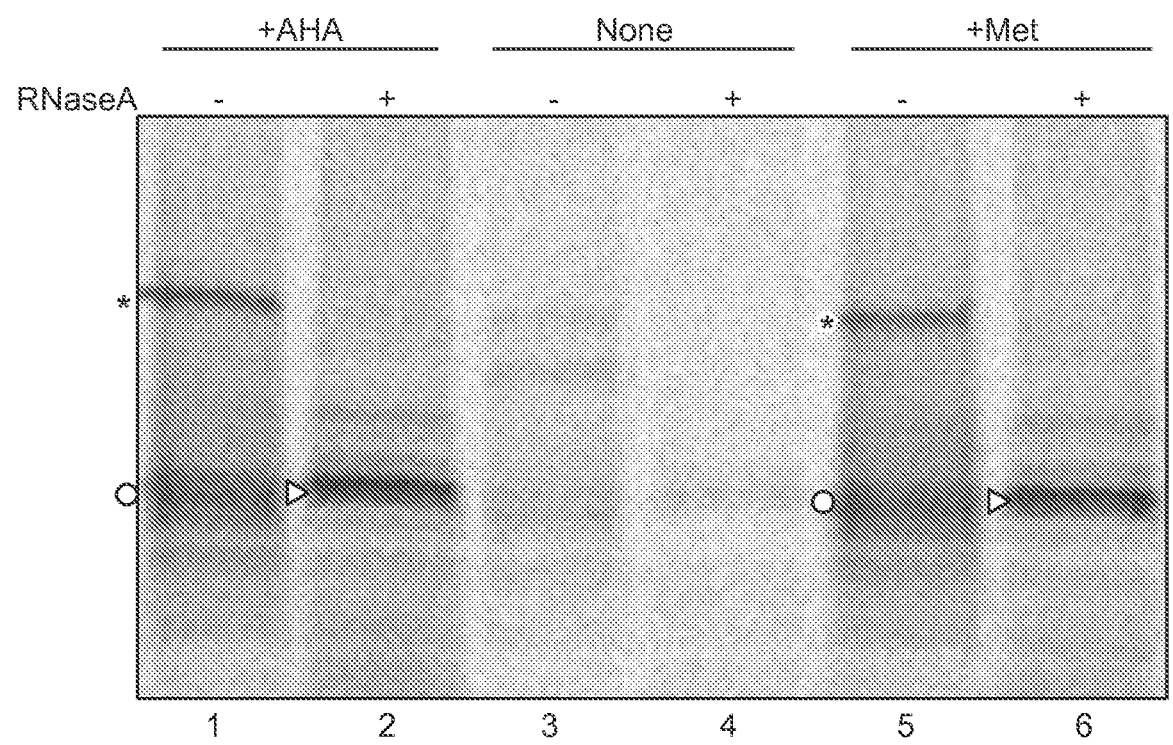
FIG. 2 depicts SDS-PAGE $^{14}$C-Phe autoradiographs of IVT reactions programmed with T4L*(-M/D61M/D159C)-secM mRNA templates and containing either azido-homo-alanine (AHA) (lanes 1-2), no methionine analogue (lanes 3-4), or methionine (lanes 5-6). RNaseA/EDTA treatment (lanes 2, 4, and 6) results in peptidyl-tRNA (*) hydrolysis and full-length peptide (▶) release. Some peptidyl-tRNA is hydrolyzed during sample loading even without RNaseA/EDTA treatment (•)
Figure 7:
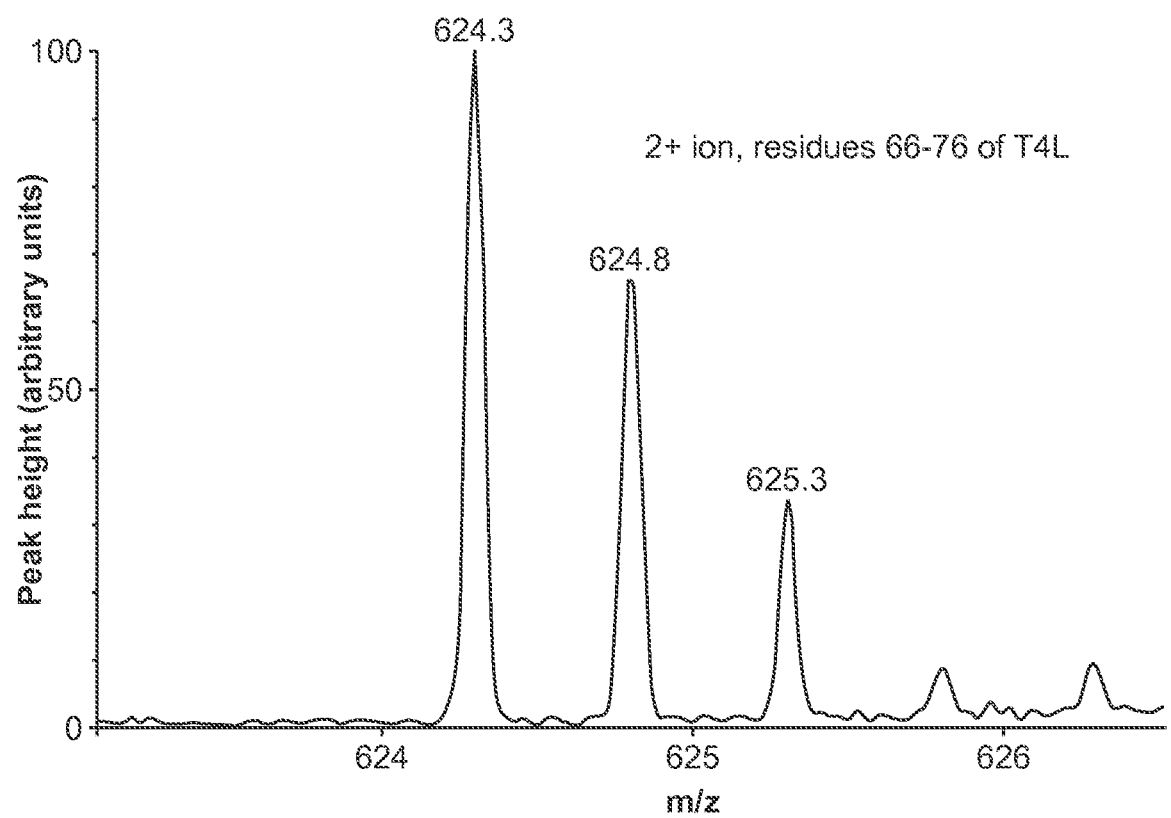
FIG. 7 depicts a peptide mass fingerprint for the +2 ion peaks of T4L residues 66-76 representative of the identified peaks provided in Table 2.

To verify the fidelity of the customized PURE IVT system, secM-stalled T4L nascent chains were translated and RNCs were purified away from most other translation components by repeated concentration and washing on a 100 kDa Amicon ultrafiltration device (Millipore). The resulting T4L nascent chains (~3 µM) were then analyzed by liquid chromatography-mass spectrometry. All expected tryptic peptides—including the N-terminal formyl-methionine peptide—were identified by the spectral fingerprints of their z=+1, +2, and/or +3 ions (see Table 2 (FIG. 6) and FIG. 7). From a 50 µL single-turnover IVT reaction containing 60 pmols of ribosomes, ~20-45 pmols of nascent chains was typically obtained as determined by total trichloroacetic acid (TCA)-precipitable $^{14}$C-Phe incorporation corresponding to a 33-75% active fraction of ribosomes. SDS-PAGE followed by $^{14}$C-Phe autoradiography also confirmed that greater than 90% of the products generated were full-length properly-stalled RNCs (FIG. 2).

Figure 14:
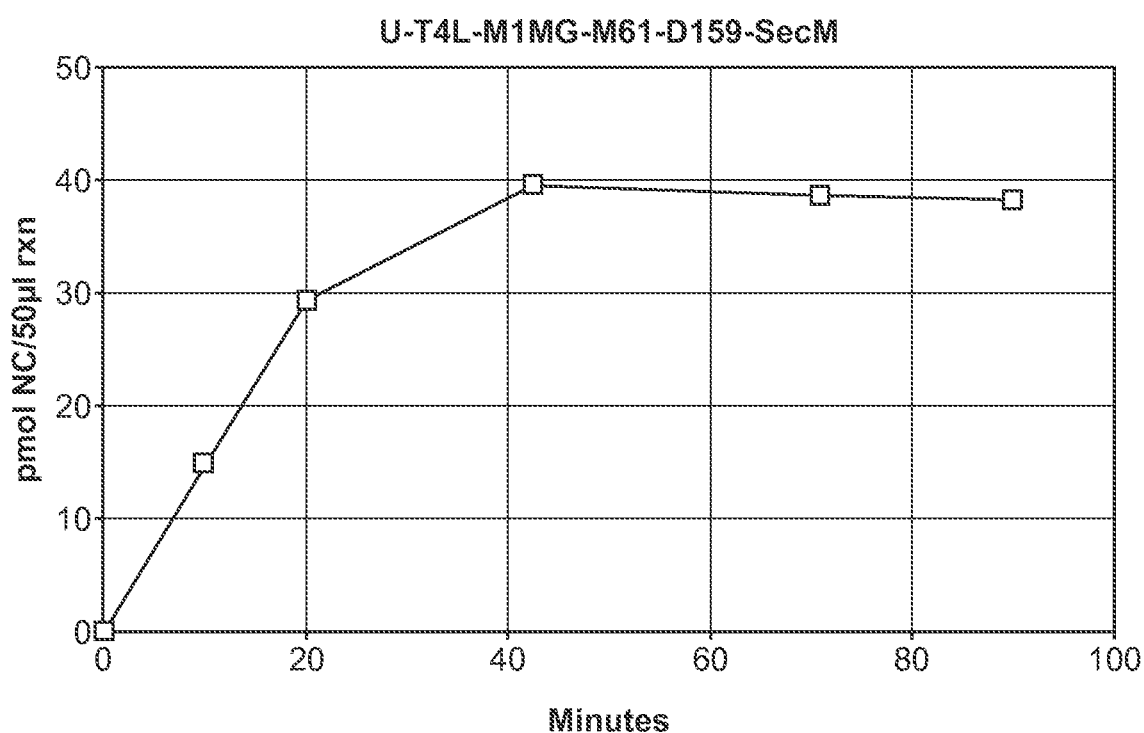
FIG. 14 depicts the kinetics of protein synthesis during PURE IVT.

Representative single-turnover mRNA-programmed PURE-IVT reaction for a T4 Lysozyme RNC construct was quantified by $^{14}$C-Phe incorporation into TCA-precipitated product. The results indicated a ribosome active fraction of 66% and an EF-Tu/ternary complex-limited maximal protein production rate of ~0.1 aa's/sec per actively translating ribosome (FIG. 14).

Unnatural Azide and Alkyne Amino Acid Incorporation

Figure 8:
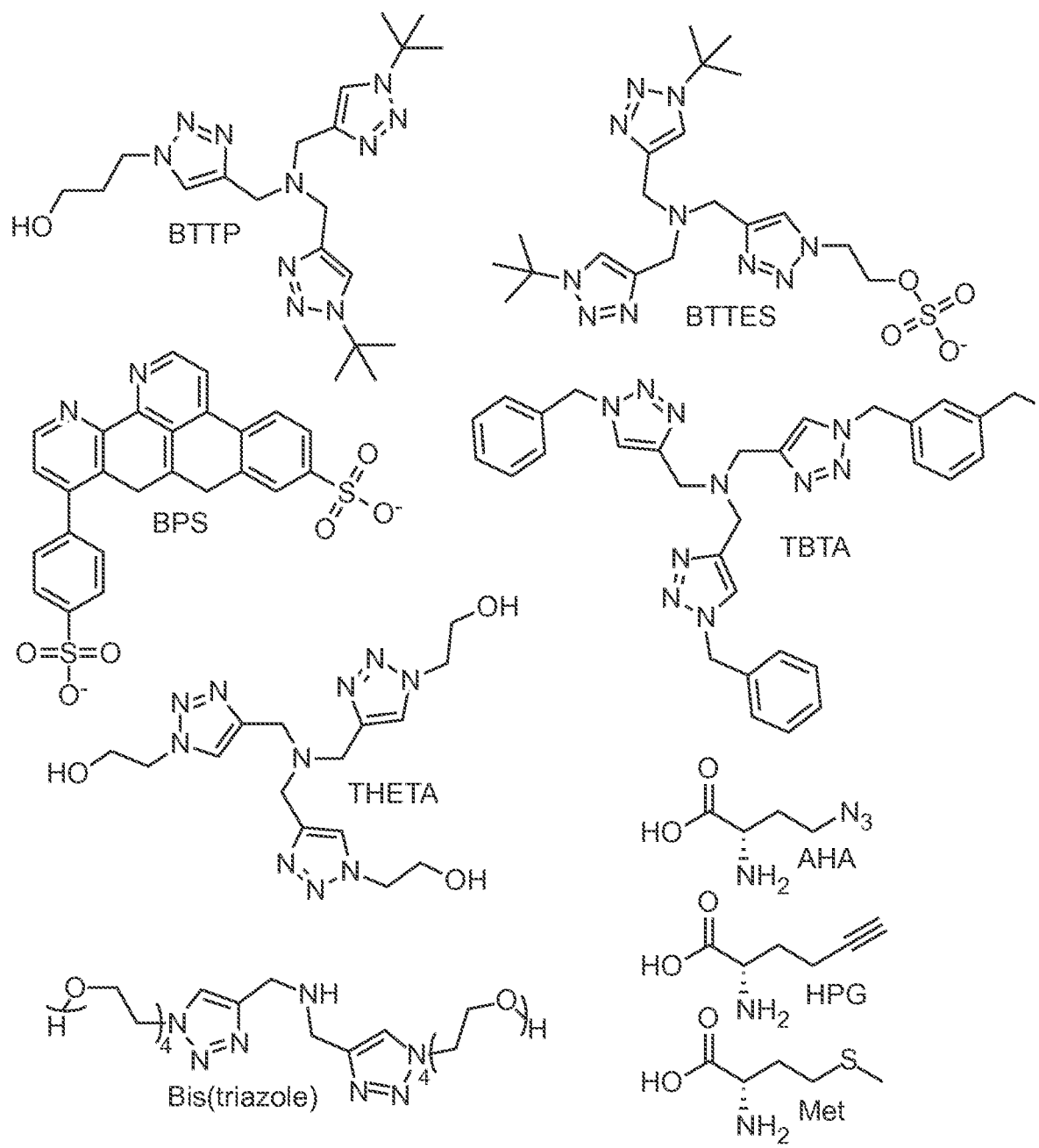
FIG. 8 depicts chemical structures of Click chemistry reagents Bathophenanthrolinedisulfonate (BPS), Tris-(benzyltriazolylmethyl)amine (TBTA), Tris-(hydroxyethyltriazolylmethyl)amine (THETA), 2-[4-([bis([tert-butyltriazol-4-yl]methyl)-amino]methyl)-triazol-1-yl]ethyl sulfate (BTTES), 3-[4-([bis([tert-butyltriazol-4-yl]methyl)amino]methyl)-triazol-1-yl]propanol (BTTP), azido-homoalanine (AHA), and homopropargylglycine (HPG).

For UAA incorporation, a simple and residue-specific metabolic tagging approach was used in which the click-compatible azide and alkyne-bearing methionine analogs azidohomoalanine (AHA) and homopropargylglycine (HPG) are efficiently charged onto native tRNAfMet and tRNAMet by endogenous E. coli MetRS (FIG. 8). UAAs were therefore incorporated into nascent proteins at all methionine codons in the encoding DNA or mRNA. This approach can easily be modified to enable site-specific tagging through genetic code reprogramming with orthogonal aaRS/tRNA pairs or pre-acylated UAA-tRNAs.

The ionic conditions of the translation reactions were optimized in order to achieve robustly quantitative UAA tagging of RNC complexes, varying all monovalent ([K+] and [NH4+]), divalent ([Mg2+] and [Zn2+]), and polyamine (spermidine and putrescine) concentrations (Table 1 (FIG. 5)). Conditions were chosen to maximize the yields of RNCs while minimizing the levels of aberrant products initiated with natural non-canonical amino acids, which would result in sub-quantitative UAA-tagging of the RNCs. Under these optimized conditions, full-length product yields were similar (~20 pmols/50 µL IVT reaction) in the presence of methionine or AHA (FIG. 2). No product was formed in the absence of both methionine and AHA (FIG. 2), indicating that background aberrant initiation with natural non-canonical amino acids is negligible under the optimized WT reaction conditions and that product formation is AHA-dependent. RNaseA/EDTA treatment of each AHA-tagged T4L-RNC sample resulted in the loss of peptidyl-tRNA bands ("*" in FIG. 2) and the appearance of full-length released protein products as expected (FIG. 2).

Several lines of evidence suggest that the IVT reactions using AHA likely result in significant unwanted side reactions that are not a problem in the HPG reactions. Under the reducing conditions required for IVT, both free and incorporated AHA residues can be reduced to click-inactive 2,4-diaminobutyrate. Comparisons between AHA, HPG, and methionine-containing IVT reactions conducted in the presence of DTT, BME, and reduced glutathione demonstrated that, under the optimized IVT reaction conditions, these side reactions are a significant problem. Acid-precipitable 14C-Phe product yields decreased dramatically with increasing AHA concentration from ~22 pmols/50 µL IVT at 30 µM AHA to 11 pmols/50 µL IVT at 1.5 mM AHA, consistent with AHA-specific inhibition of translational activity via the oxidation of reducing agents and translation-essential cysteines in the IVT system. In contrast, IVT reactions with HPG consistently gave higher yields of nascent chains, ~45 pmols/50 µL IVT at 250 µM HPG, equivalent to those obtained with methionine. To avoid these redox-sensitive issues HPG-tagging was used.

Ligand and Cu(I)-catalyzed Azide-Alkyne Cycloaddition (CuAAC)

The use of the ligand-assisted CuAAC reaction for bioconjugations in complex biochemical environments is often complicated by the wide variety of unwanted side reactions induced by the combination of copper, ascorbate, and molecular oxygen. For example, in vivo imaging applications are often limited by the cytotoxicity of copper and have motivated the development of copper-free azide-alkyne cycloaddition reagents. For in vitro bioconjugations, the production of reactive oxygen species together with the potential for hydrolytic damage to sensitive protein and RNA substrates poses significant challenges. A further complication for single molecule FRET applications is that copper may induce dye photophysics (i.e. blinking and bleaching) via a wide variety of mechanisms. Finally, copper(II) efficiently catalyzes amino-acyl-tRNA bond hydrolysis complicating RNC labeling applications. Despite these potential pitfalls a variety of ligand-assisted CuAAC reactions were examined for their ability to provide rapid, complete, and specific labeling of tagged RNCs.

Tris-triazolyl ligands play a mechanistic role during catalysis as well as a crucial role in protecting samples from reactive oxygen species produced during aerobic bioconjugations. These ligands can either enhance or inhibit the reaction depending on their relative tendency to form catalytically-active binuclear $[L](Cu^I)_2$ complexes to which azide substrates have access versus catalytically-inactive polymeric copper acetylides that often precipitate from aqueous solutions. The complex interdependence of target properties, solution conditions, and ligand choice also often necessitates the optimization of bioconjugation reaction conditions for each target or application.

For each target protein, the effect of various tris-triazole ligands on the degree of reaction completion under conditions known to stabilize RNC complexes was evaluated. FIG. 8 lists the structures of the ligands tested. Initial trials with TBTA in air-saturated reactions induced rapid and quantitative RNC sample degradation and aggregation. All further labeling reactions were therefore conducted in a glove bag under anaerobic conditions (typically <10 ppm O2) to minimize the unwanted generation of reactive oxygen and carbonyl species. In addition, copper-induced hydrolytic cleavage of rRNA, tRNA, and peptidyl-tRNA bonds was mitigated by the addition of an excess of competing magnesium ions and the maintenance of a neutral pH.

Figure 9:
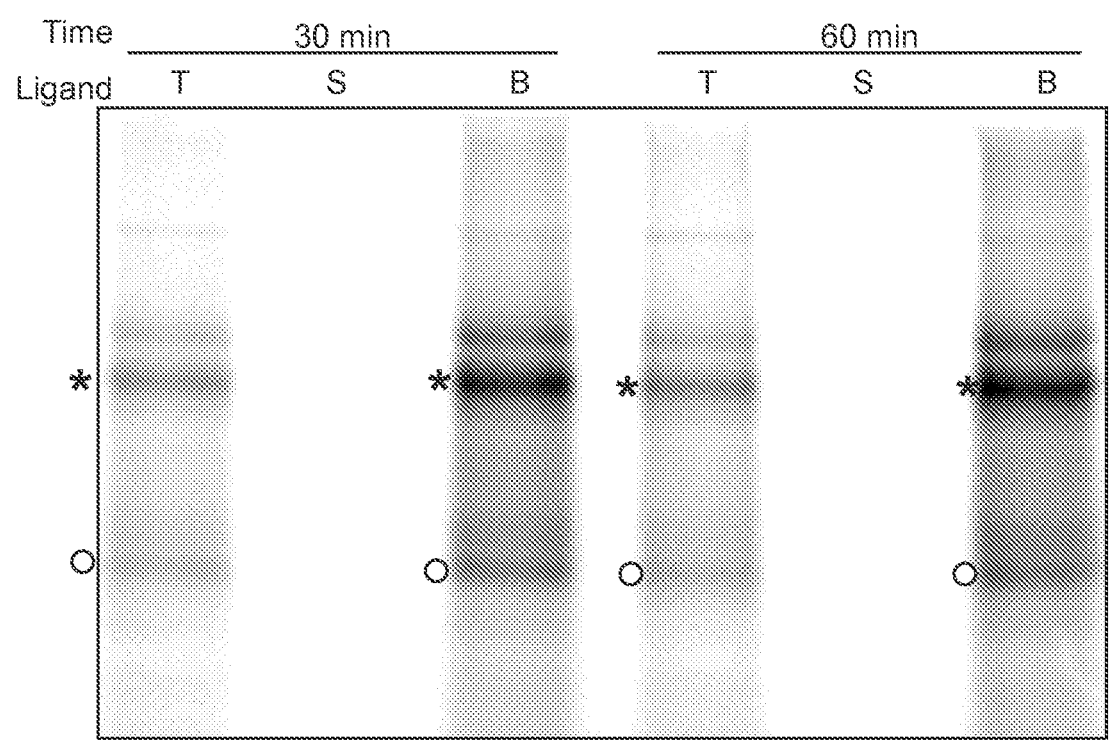
FIG. 9 depicts AHA-tagged T4L labeled with ~6 μM Alexa647-alkyne by CuAAC reaction using either 1 mM of THETA (T), BPS (S), or BTTP (B) together with 0.5 mM Cu(I)Br in RNC stabilization buffer (pH 7.0) for the indicated times. Peptidyl-tRNA (*) and released T4L peptide bands (•) are indicated.

Using HPG-tagged RNCs, the choice of accelerating ligand, total copper concentration, copper-to-ligand ratio, source of catalytic Cu(I) ions, sample deoxygenation protocol, concentrations of donor and acceptor azido-dyes, and buffer conditions were optimized in order to maximize the rate and degree of completion of the CuAAC reactions while minimizing potential oxidative or hydrolytic damage to the RNC complexes. These optimizations resulted in robustly quantitative fluorescent dye incorporation into RNCs in the presence of the accelerating bis(tert-butyl)tris-triazolyl ligands BTTES and BTTP (see FIG. 8). These ligands have many advantages over other accelerating ligands: they are more water soluble and thus more compatible with aqueous bioconjugations than TBTA; they are less oxygen and pH sensitive than BPS (FIG. 9) and other bis(triazolyl) ligands; and, the two bulky tert-butyl groups in this class of ligands efficiently inhibit the formation of polymeric copper acetylide species thereby sustaining higher catalytic rates and degrees of completion than are possible with THETA. This ultimately enables the high levels of reaction completion and dual labeling that are required for smFRET applications (FIG. 9).

Figure 3:
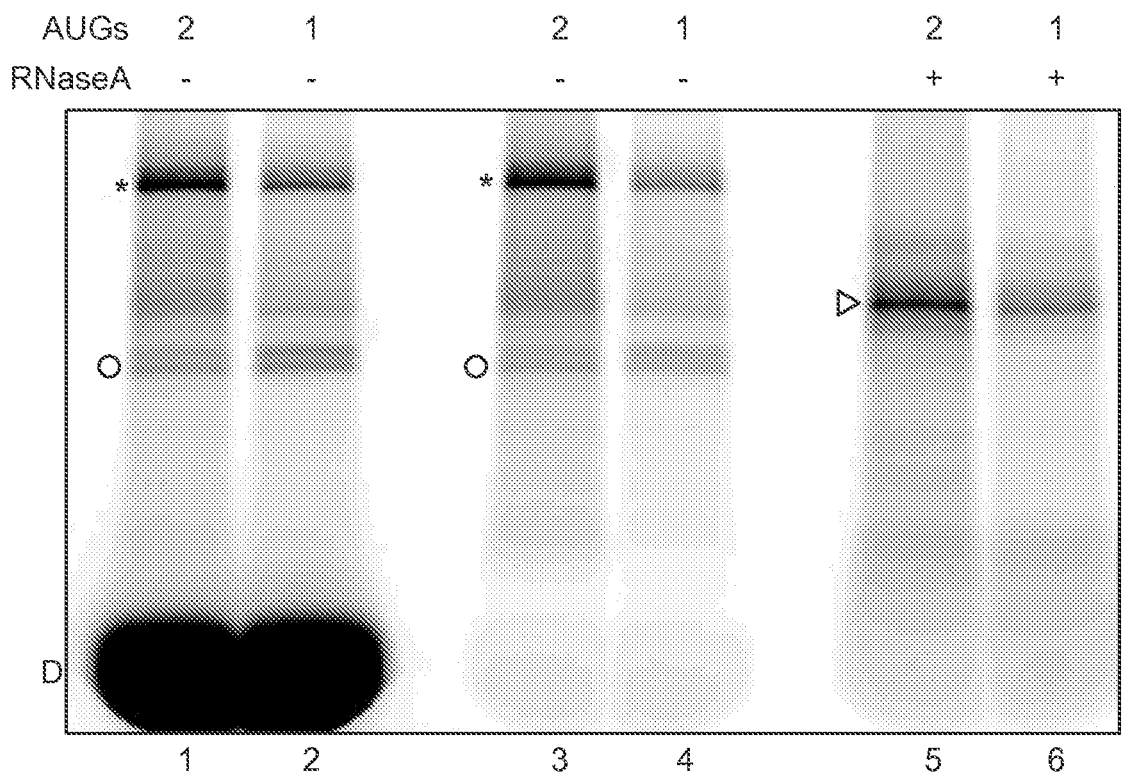
FIG. 3 depicts SDS-PAGE fluorography of efficient post-translational dye attachment to ribosome-bound nascent proteins using ligand-assisted Cu(I)-catalyzed azide-alkyne cycloaddition. Fluorescently-labeled T4L*(-M)-secM ribosome-nascent chain samples from IVTs containing HPG and programmed with mRNAs encoding either one (lanes 2, 4, and 6) or two (lanes 1, 3, and 5) AUGs following the different steps of sample preparation: before free dye removal (lanes 1-2), after free dye removal (lanes 3-4), or following RNaseA/EDTA treatment. Peptidyl-tRNA (*), initiator and elongator methionyl-tRNAs (•), released protein (▶), and the free dye (D) are indicated.

These parameters together with the inherent advantages of the bis(tert-butyl)tris-triazolyl-ligands ultimately provided samples with a labeling efficiency of about 70% (see FIG. 3). Random labeling at each of the two HPG sites with donor and acceptor fluorescent dye conjugates should yield a mixture of donor-only (i.e. D-, -D, and DD at the two sites), acceptor-only (i.e. A-, -A, and AA), and dual-labeled FRET-active species (DA, and AD) which obeys a binomial distribution. A 70% labeling efficiency would correspond to a minimal FRET-active (DA and AD) population of (0.7)2/2~25% which is sufficient for most smFRET applications. These data also indicate that less than 30% of the initial ribosome-bound secM-stalled peptidyl-tRNAs are hydrolyzed during the CuAAC reaction. Sucrose density gradient analysis of labeled RNCs confirmed that ribosomal subunits do not dissociate or aggregate as a result of the CuAAC reaction. Finally, no irreversible bleaching of dye fluorescence as a result of the CuAAC click reaction was observed.

Figure 20:
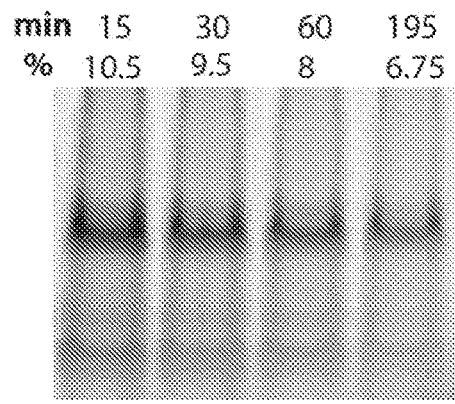
FIG. 20 depicts BPS/CuAAC labeling of AHA-tagged T4 lysozyme.
Figure 21:
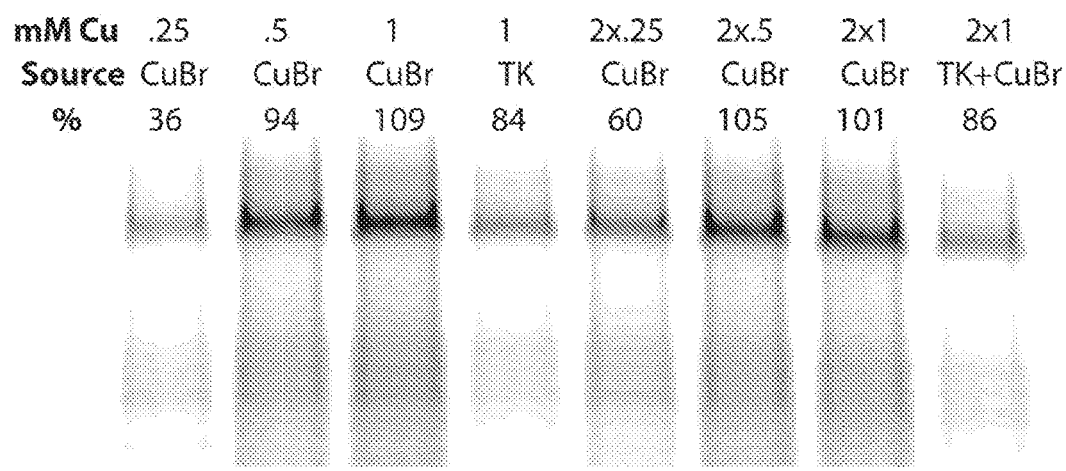
FIG. 21 depicts THPTA/CuAAC labeling of properly quenched AHA-tagged T4 lysozyme.
Figure 22:
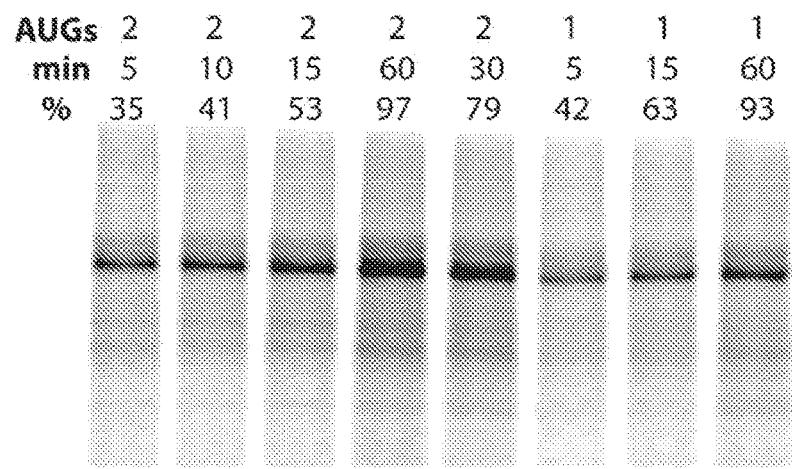
FIG. 22 depicts BTTP/CuAAC labeling kinetics of T4 lysozyme RNCs tagged with HPG at various positions.

Aerobic TBTA/CuSO$_4$/ascorbate CuAAC trials initially induced rapid target degradation and aggregation while aerobic TBTA/CuSO$_4$/TCEP reactions remained incomplete. Under anaerobic (i.e. <10 ppm O$_2$) conditions with HPG-tagged RNCs, the choice of accelerating ligand, total copper concentration, copper-to-ligand ratio, source of catalytic Cu$^I$ ions, sample deoxygenation protocol, concentrations of donor and acceptor azido-dyes, and buffer conditions to achieve reaction completion while minimizing ROS, RCS, or hydrolytic damage to our sensitive RNA and protein-containing targets were optomized. BPS/CuBr trials were rapid but sample degradation and inhibitory bis-bidentate complex formation proved limiting for this ligand (FIG. 20). Due to competing Cu-center aggregation ~1 millimolar doses of copper were required to achieve quantitative labeling using the water-soluble tris(triazolylmethyl)amine ligands THETA and THPTA (FIG. 21). In contrast, completion was robustly achieved in less than one hour using micromolar quantities of Cu$^I$ and a 2-fold excess of BTTES or BTTP (FIG. 3 and FIGS. 22-23). Under these conditions the peptidyl-tRNA bond remained intact, dye fluorescence and test protein activity remain unaltered and no RNC disassembly/aggregation or mRNA degradation was evident via sucrose gradient analysis (FIG. 24). That 4° C. labeling and 4 mM aminoguanidine didn't significantly compromise reaction kinetics or completion was also verified (FIG. 25). Notably, less stringently-anaerobic CuAAC labeling conditions have been applied to ribozymes and mRNA-display libraries without loss of activity or function. However, copper/ascorbate removal prior to sample reoxygenation is required to prevent sample degradation. Finally, extremely copper-sensitive targets can also be labeled at ~5-fold lower copper loads than described here by using commercially-available picolyl-azide dyes.

FIGS. 20-25 show CuAAC labeling optimizations. FIG. 20. BPS/CuAAC labeling of AHA-tagged T4 Lysozyme RNCs. The reaction remains incomplete either because of azide-inactivation prior to labeling (IVT reactions were not properly quenched with excess azide prior to sucrose pelleting) or inhibitory bis-bidenate complex formation during labeling. Peptidyl-tRNA band degradation is also evident at long times. Labeling conditions: 50 µM CuBr, 150 µM BPS, 17 µM Alexa647-alkyne, ~1 µM AHA-RNCs, <10 ppm O$_2$. FIG. 21. THPTA/CuAAC labeling of properly-quenched AHA-tagged T4 Lysozyme RNCs using different Cu$^I$-sources (Cu$^I$Br or Tetrakis (TK) acetonitrile Cu$^I$ triflate) and dosage schemes (mM units and number of doses are indicated). Conditions: 1 hr labeling time, Cu:THPTA=1:4, 16 uM dye, ~1 uM AHA-RNCs, <10 ppm $O_2$. FIG. 22. BTTP/CuAAC labeling kinetics of T4 Lysozyme RNCs tagged with HPG at positions 1-38 (lanes 1-5) or position 1-only (lanes 6-8). Conditions: 0.5 mM Cu, 1 mM BTTP, 1 mM ascorbic acid, ~0.75 uM RNCs, 12 uM dye. FIG. 23 Similar to FIG. 22 lanes 1-5 but at varying copper concentrations while holding Cu:BTTP ratio constant at 1:2. FIG. 24. Analytical sucrose gradient analyses of ribosomes (left), a PURE IVT reaction without BTTP/CuAAC labeling (second chromatograph), and PURE WT reactions with BTTP/CuAAC labeling (other chromatographs). Conditions: 1 hr at 0.75 mM Cu, 1 mM ascorbate, 1.5 mM BTTP, <10 ppm $O_2$. FIG. 25. Labeling at 4° C. or in the presence of 4 mM aminoaguanidine (AG) has a minor effect on the BTTP/CuAAC reaction. Conditions: similar to FIG. 22 and FIG. 23. The major band in all gels is the peptidyl-tRNA band for the full-length protein. In some gels images the released protein can also be observed (at lower $M_w$ but this is an artifact of SDS-PAGE gel loading and should not be taken to suggest that samples used for smFRET are not completely intact).

The sample preparation protocol is well-suited for high throughput studies. Since the current RNC purification protocol calls for an ultracentrifugation/sucrose pelleting, the throughput for single-turnover RNC sample preparation is limited to 20 parallel samples by the TLA-100 rotor used. For multi-turnover/released samples, the current purification protocol requires a low speed centrifugation/desalting step that is similarly limited to 24 parallel samples. Both of these throughputs can be scaled up by switching to 96-well desalting platforms as needed (e.g. Zeba 96-well spin plates, Thermo Scientific).

Single-Molecule FRET with Alternating Laser Excitation

Figure 4A:
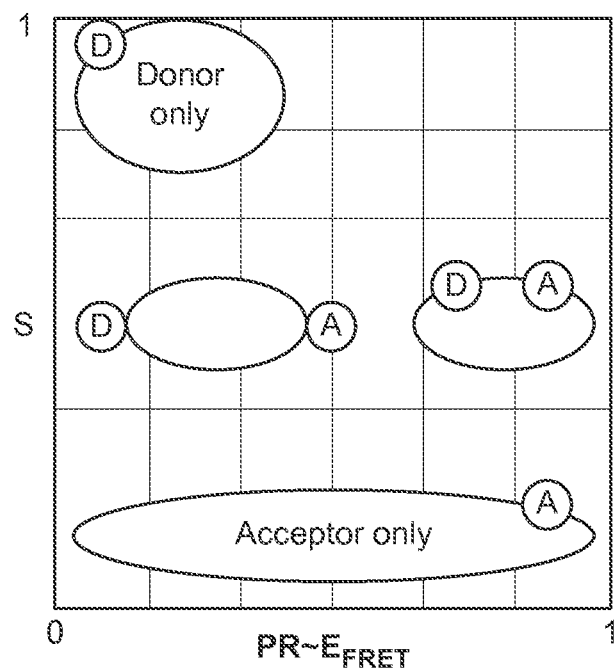
FIGS. 4A-4F depict Proximity Ratio (PR) and Stoichiometry (S) 2D histograms revealing sub-populations of labeled ribosome bound and freely-diffusing Barnase protein samples prepared for single molecule FRET with alternating laser excitation (sm-FRET-ALEX) studies of protein folding and dynamics. (A) Illustration of the various sub-populations of predicted single and dual-labeled Barnase protein samples on a PR-S 2D histogram. Measured PR-S 2D histograms of single-labeled (B) and dual-labeled (C-F) Barnase RNCs, either stalled (C and E) or non-stalled (D and F).
Figure 4B:
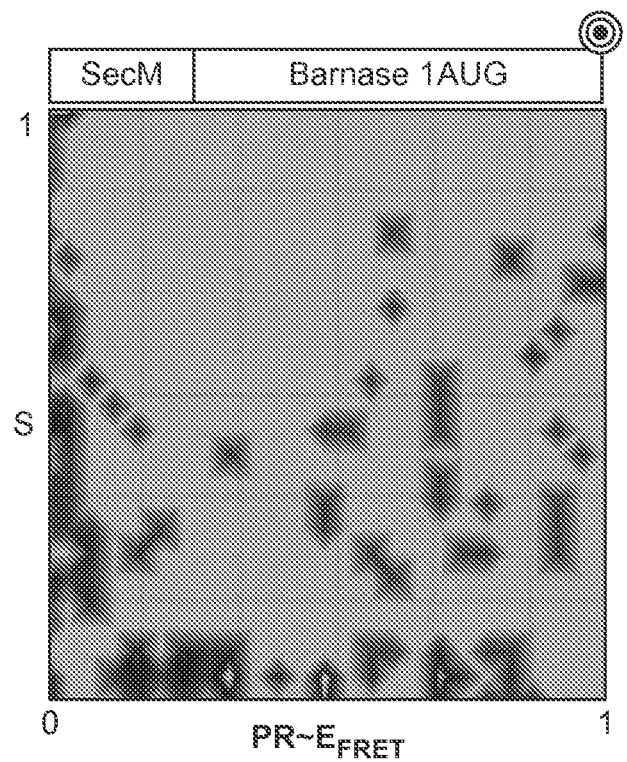
Figure 4C:
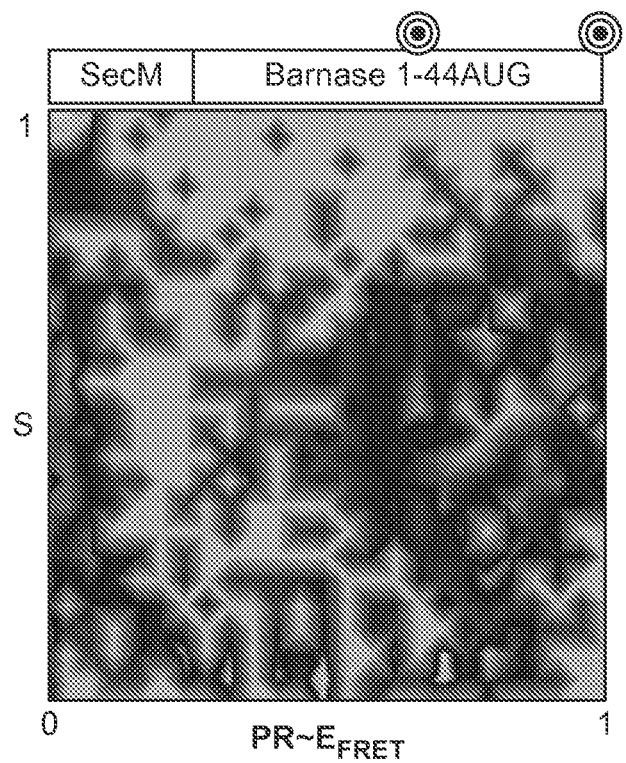
Figure 4D:
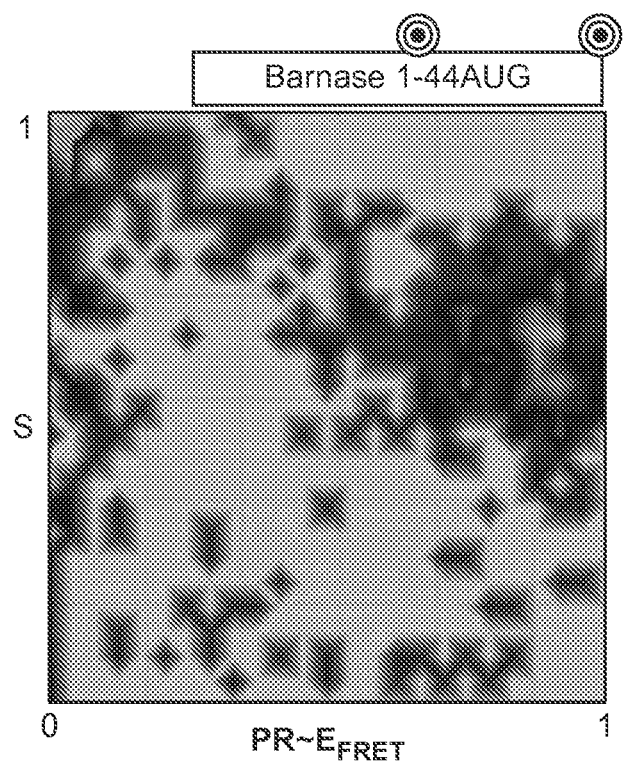
Figure 4E:
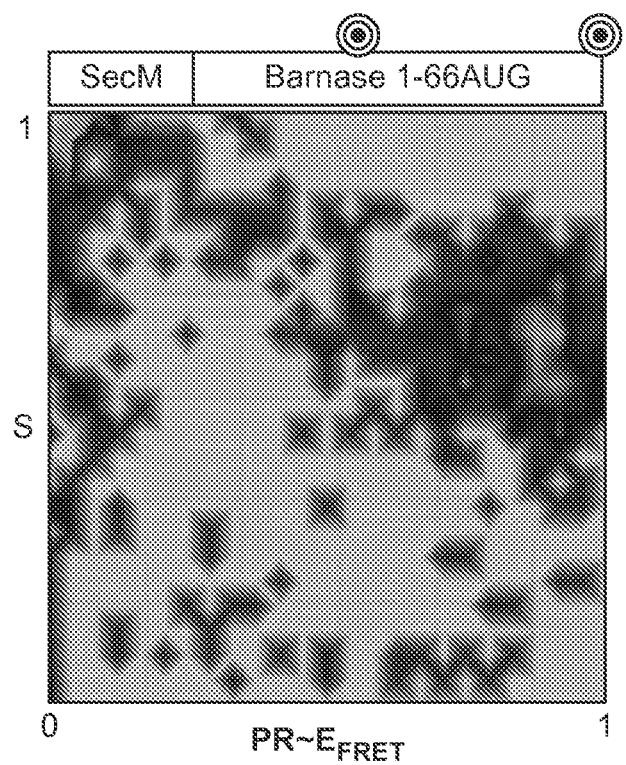
Figure 4F:
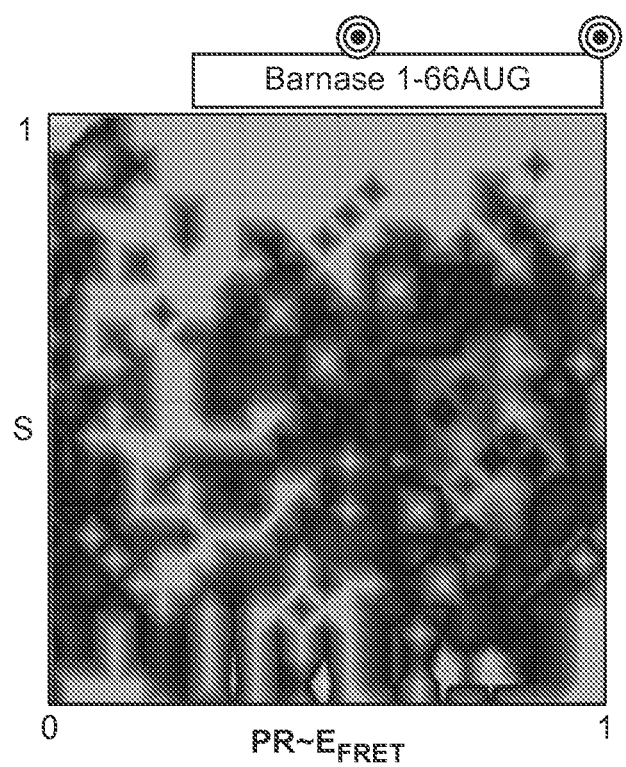

The above protocol results in samples suitable for smFRET studies. In order to obtain a more quantitative estimate of the degree of dual-labeled FRET-active RNCs resulting from the optimized BTTP/CuAAC reactions. A diffusion-based confocal smFRET microscope with alternating laser excitation (ALEX) capabilities was used (FIG. 10). Donor-only, acceptor-only, and dual-labeled fluorescence bursts arising from individual proteins and RNCs diffusing through the confocal observation volume were resolved along the molecular Stoichiometry (S) axis whereas FRET-active dual-labeled species (i.e. DA or AD) with different interfluorophore distances are resolved along the uncorrected FRET efficiency (EFRET) or Proximity Ratio (PR) axis (see FIG. 4A). FIG. 4 shows two-dimensional PR-S histograms obtained for various secM-stalled/RNC and non-stalled (released) barnase samples. Control samples programmed with secM-stalling mRNAs encoding the incorporation of HPG only at the initiator ATG codon (amino acid position 1) exhibited no dual-labeled population as expected (FIG. 4B). In contrast, secM-stalled (FIGS. 4C and 4E) and non-stalled (FIGS. 4D and 4F) barnase samples programmed with two ATGs either at positions 1 and 44 (1-44) or at 1 and 66 (1-66) yielded reproducible FRET-active dual-labeled (DA+AD) sub-populations of ~30%, consistent with an 80% degree of reaction completion in general agreement with in-gel fluorescence quantification data (FIG. 3).

Non-stalled constructs (FIGS. 4D and 4F), produced using a commercial PURE IVT kit and encoding barnase 1-44 and 1-66, yielded dual-labeled populations with mean PRs of ~0.84 and ~0.7, respectively. These values are consistent with the X-ray and NMR-determined native structures of barnase in which the inter-residue distances of the 1-44 and 1-66 labeling sites are ~2 nm and ~4 nm, respectively. In contrast, the secM-stalled and ribosome-bound barnase constructs labeled at the same sites (FIGS. 4C and 4E) both exhibited broad PR distributions centered at ~0.75 consistent with a collapsed, heterogeneous, and non-native conformational distribution. Based on cryo-EM reconstructions of secM-stalled RNCs, the minimal 17-residue SecM-stalling sequence used in the present studies would result in the sequestration of roughly 10-20 residues from the C-terminus of barnase within the exit tunnel of the ribosome. The results are therefore consistent with previous studies which found that the C-terminal 15 residues of Barnase are required for folding into a stable native conformation both off and on the ribosome.

Hundreds of released as well as ribosome-bound dual-labeled polypeptides and mutant polypeptides were generated by PURE IVT for the described smFRET studies (see Table 4 and Table 5 for lists of polypeptides generated and the constructs used in generating the polypeptides). Mutant polypeptides generated of barnase, T4 lysozyme (T4L), the R16 domain of chicken alpha-spectrin, and the 128 domain of human cardiac titin include but are not limited to, e.g., backbone truncations, C-terminal-extensions, side-chain truncations, circular permutants, labeling site mutants, etc. Stalled RNC complexes were generated using the 17-residue SecM stalling sequence and translation reactions were programmed using fully in vitro generated DNA or mRNA templates.

Using a non-parallelized and custom-built diffusion-based confocal smFRET microscope with alternating laser excitation (ALEX) capabilities two-dimensional FRET efficiency-molecular stoichiometry (i.e. "$E_{PR}$-S") histograms were acquired for the hundreds of individually-expressed and dual-labeled proteins and RNC constructs (FIGS. 4B-4F and FIG. 26-FIG. 55). Single-HPG templates yielded singly-labeled (i.e. donor-only or acceptor-only) products while dual-HPG templates yielded dual-labeled/FRET-active (i.e. DA or AD) sub-populations. These results illustrate—with single molecule sensitivity—the high specificity and efficiency achieved for both UAA-tagging and dye labeling using this approach. They also indicate that the labeling sites chosen, including those sites that were novel in the systems explored, were highly accessible. The $E_{PR}$ distributions of ribosome-bound, RNase/EDTA-released, and non-stalled constructs acquired under different solution conditions and in the context of different C-terminal sequences and (for RNC samples) different tethering lengths to the peptidyl-transferase-center (PTC) allowed the exploration of effects of the ribosome on nascent chain structure and folding.

Figure 26:
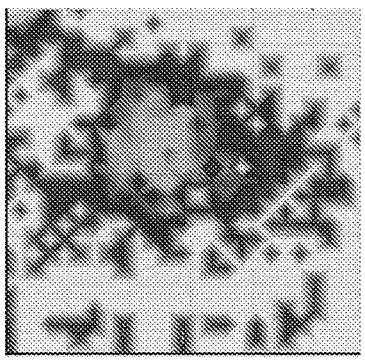
FIG. 26 depicts a representative single molecule $E_{PR}$-S histogram for Spectrin R16 KH M1-M39 wt EK-peptide released protein (0.1 M GdmHCl) tagged and labeled at M1-M39.
Figure 27:
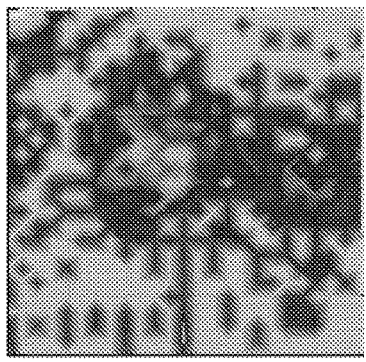
FIG. 27 depicts a representative single molecule $E_{PR}$-S histogram for Spectrin R16 KH M1-M39 L97A EK-peptide released protein (0.1 M GdmHCl) tagged and labeled at M1-M39.
Figure 28:
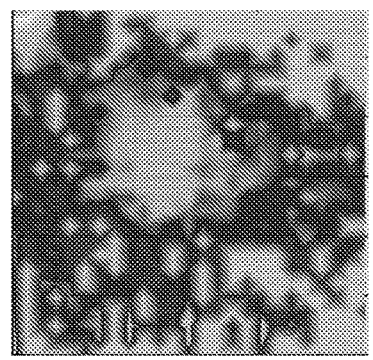
FIG. 28 depicts a representative single molecule $E_{PR}$-S histogram for Spectrin R16 KH M1-M39 R17a released protein (0.1 M GdmHCl) tagged and labeled at M1-M39.
Figure 29:
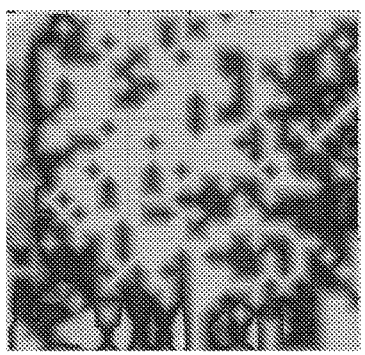
FIG. 29 depicts a representative single molecule $E_{PR}$-S histogram for Spectrin R16 KH M1 R17a-SecM RNC (0.1 M GdmHCl) tagged and labeled at M1.
Figure 30:
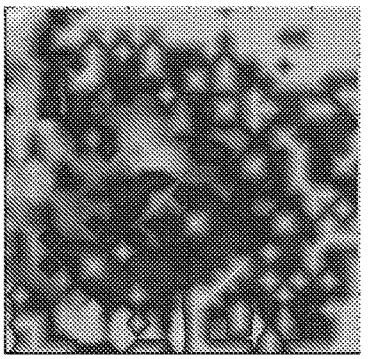
FIG. 30 depicts a representative single molecule $E_{PR}$-S histogram for Spectrin R16 KH M1-M39 R17a-SecM RNC (0.1 M GdmHCl) tagged and labeled at M1-M39.
Figure 31:
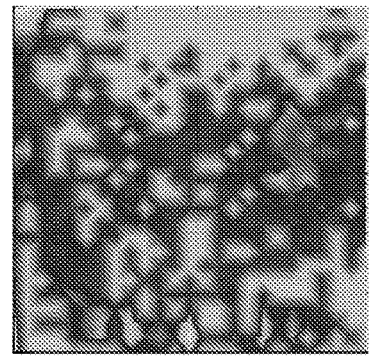
FIG. 31 depicts a representative single molecule $E_{PR}$-S histogram for Spectrin R16 KH M1-M92 wt R17a-SecM RNC (0.1 M GdmHCl) tagged and labeled at M1-M92.
Figure 32:
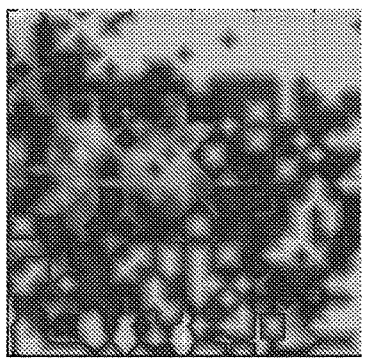
FIG. 32 depicts a representative single molecule $E_{PR}$-S histogram for Spectrin R16 KH M1-M39 R17a-SecM RNC (0.1 M GdmHCl)tagged and labeled at M1-M39.
Figure 33:
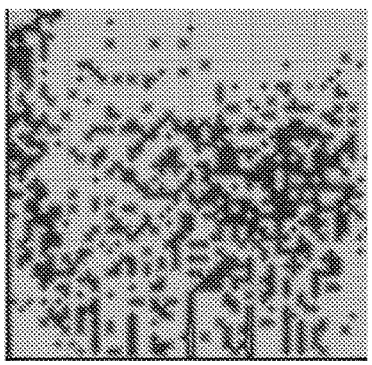
FIG. 33 depicts a representative single molecule $E_{PR}$-S histogram for Barnase M1-M66 Δ95 SecM RNC (0.1 M GdmHCl) tagged and labeled at M1-M66.
Figure 34:
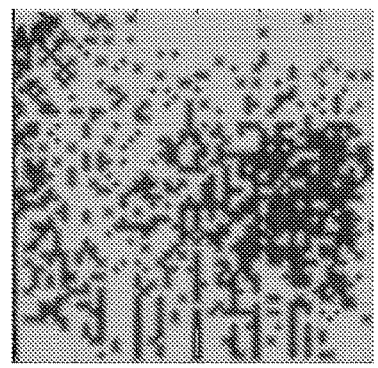
FIG. 34 depicts a representative single molecule $E_{PR}$-S histogram for Barnase M1-M66 (GS)$_{10}$-SecM RNC (0.1 M GdmHCl) tagged and labeled at M1-66.
Figure 35:
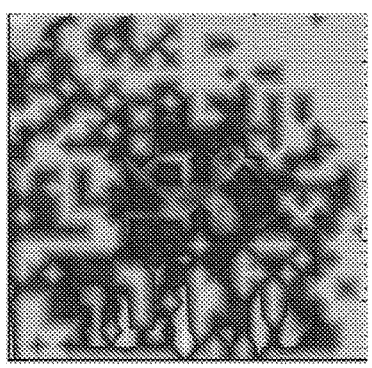
FIG. 35 depicts a representative single molecule $E_{PR}$-S histogram for Barnase M1-M66 wt-SecM RNC (2 M GdmHCl) tagged and labeled at M1-66.
Figure 36:
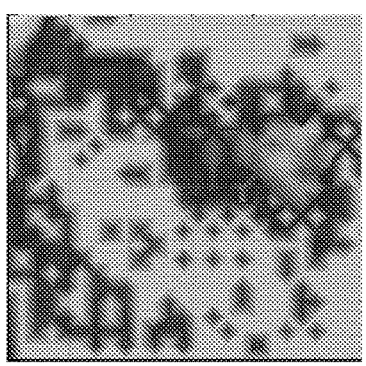
FIG. 36 depicts a representative single molecule $E_{PR}$-S histogram for Barnase M1-M66 wt released protein (1×PBS buffer) tagged and labeled at M1-M66.
Figure 37:
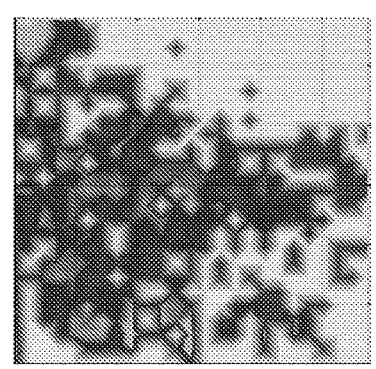
FIG. 37 depicts a representative single molecule $E_{PR}$-S histogram for Spectrin R16 KH M1-M39 R17a-SecM RNC released by Rnase/EDTA treatment (0.1 M GdmHCl) tagged and labeled at M1-M39.
Figure 38:
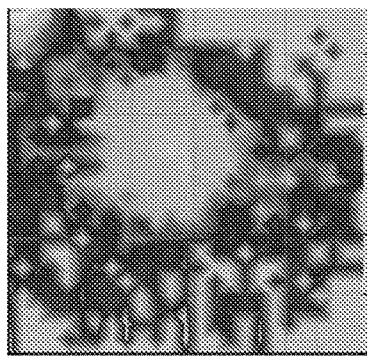
FIG. 38 depicts a representative single molecule $E_{PR}$-S histogram for Spectrin R16 KH M1-M39 G105A EK-peptide released protein (0.1 M GdmHCl) tagged and labeled at M1-M39.
Figure 39:
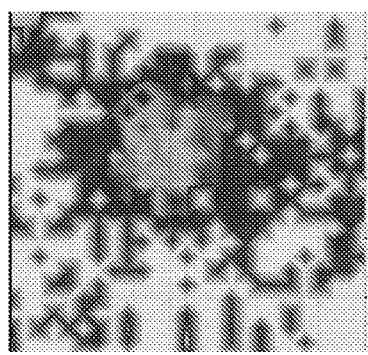
FIG. 39 depicts a representative single molecule $E_{PR}$-S histogram for Spectrin R16 KH M1-M39 G105A GEK-peptide released protein (0.1 M GdmHCl) tagged and labeled at M1-M39.
Figure 40:
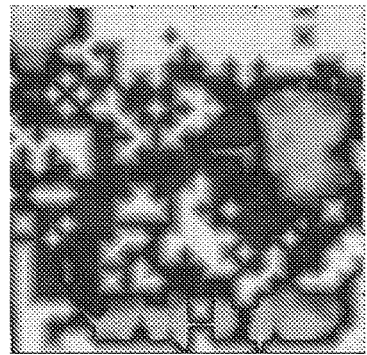
FIG. 40 depicts a representative single molecule $E_{PR}$-S histogram for Spectrin R16 KH M1-M36 R17a-SecM RNC (0.1 M GdmHCl) tagged and labeled at M1-M36.
Figure 41:
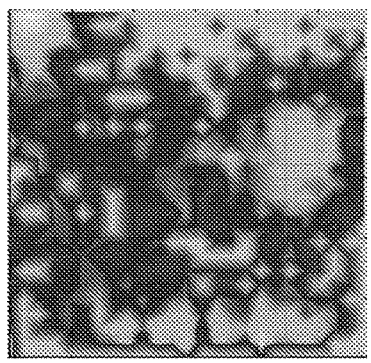
FIG. 41 depicts a representative single molecule $E_{PR}$-S histogram for Spectrin R16 KH M1-M39 R17a-SecM RNC (0.1 M GdmHCl) tagged and labeled at M1-M39.
Figure 42:
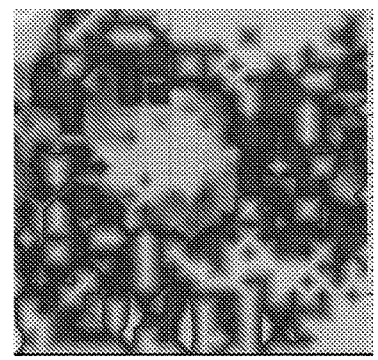
FIG. 42 depicts a representative single molecule $E_{PR}$-S histogram for Spectrin R16 KH M1-M39 R17a released protein (0.1 M GdmHCl) tagged and labeled at M1-M39.
Figure 43:
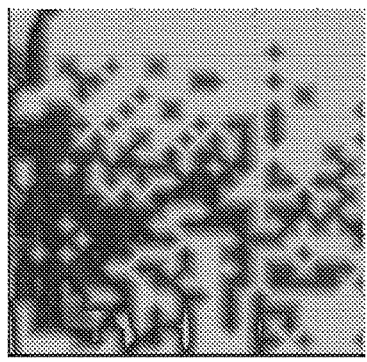
FIG. 43 depicts a representative single molecule $E_{PR}$-S histogram for Titin 128 M1 released (aggregated) protein (1×PBS) tagged and labeled at M1.
Figure 44:
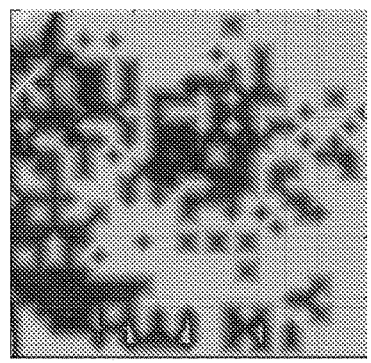
FIG. 44 depicts a representative single molecule $E_{PR}$-S histogram for Titin 128 M1-M70 released (aggregated) protein (1×PBS) tagged and labeled at M1-M70.
Figure 45:
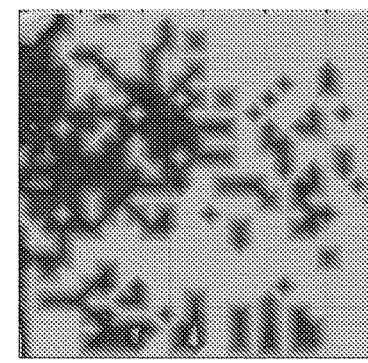
FIG. 45 depicts a representative single molecule $E_{PR}$-S histogram for Titin 128 M1-M94 released (aggregated) protein (1×PBS) tagged and labeled at M1-M94.
Figure 46:
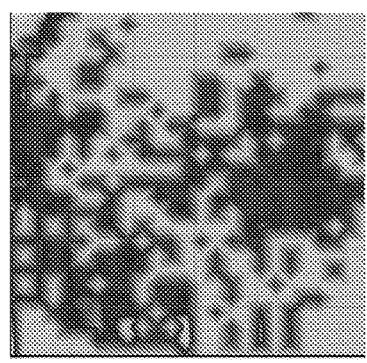
FIG. 46 depicts a representative single molecule $E_{PR}$-S histogram for Titin 128 M1-M72 released (denatured and refolded) protein (1×PBS) tagged and labeled at M1-M72.
Figure 47:
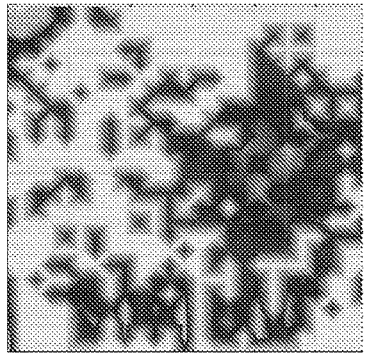
FIG. 47 depicts a representative single molecule $E_{PR}$-S histogram for T4 Lysozyme M1-M38-CTDA94-SecM RNC (2 M GdmHCl) tagged and labeled at M1-M38.
Figure 48:
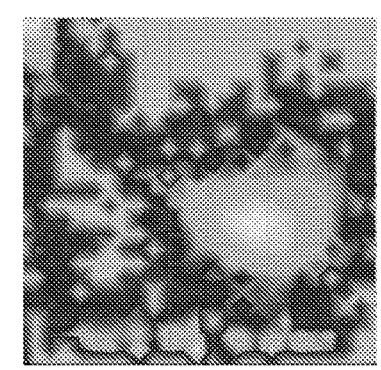
FIG. 48 depicts a representative single molecule $E_{PR}$-S histogram for T4 Lysozyme M1-M38-(GS)$_{15}$-SecM RNC (3 M GdmHCl) tagged and labeled at M1-M38.
Figure 49:
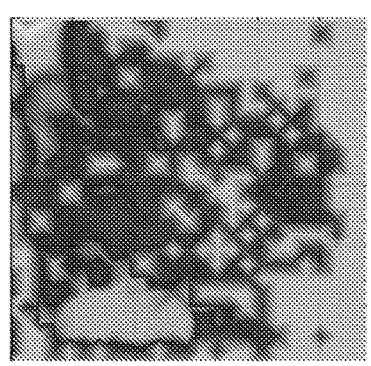
FIG. 49 depicts a representative single molecule $E_{PR}$-S histogram for T4 Lysozyme M1-SecM RNC (2 M GdmHCl), AHA-tagged tagged and labeled at M1.
Figure 50:
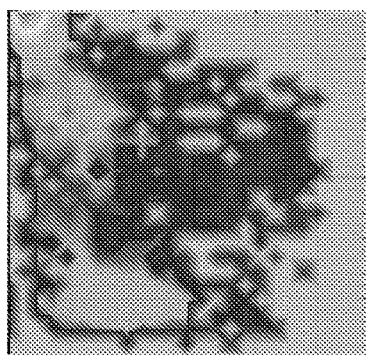
FIG. 50 depicts a representative single molecule $E_{PR}$-S histogram for T4 Lysozyme M1-M61-SecM RNC (2 M GdmHCl), AHA-tagged tagged and labeled at M1-M61.
Figure 51:
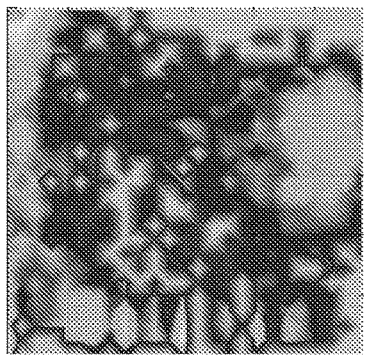
FIG. 51 depicts a representative single molecule $E_{PR}$-S histogram for T4 Lysozyme NTD M12-M55 EK-peptide-(GS)$_3$-SecM RNC (1×PBS 1 mM Mg(OAc)$_2$) tagged and labeled at M12-M55.
Figure 52:
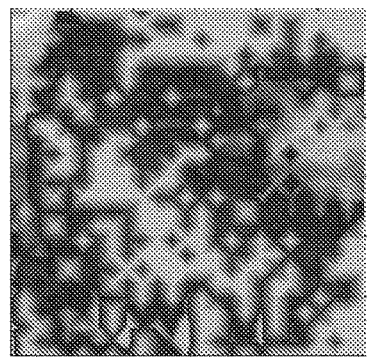
FIG. 52 depicts a representative single molecule $E_{PR}$-S histogram for T4 Lysozyme NTD M12-M53 PEK-peptide-(GS)$_3$-SecM RNC (1×PBS 1 mM Mg(OAc)$_2$) tagged and labeled at M12-M53.
Figure 53:
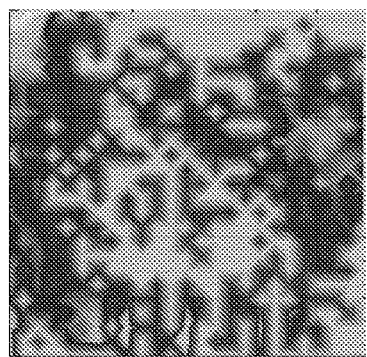
FIG. 53 depicts a representative single molecule $E_{PR}$-S histogram for T4 Lysozyme NTD M12-M55 PEK-peptide-(GS)$_3$-SecM RNC (1×PBS 1 mM Mg(OAc)$_2$) tagged and labeled at M12-M55.
Figure 54:
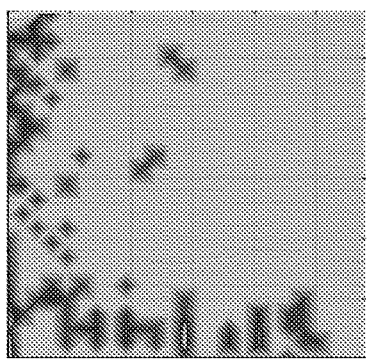
FIG. 54 depicts a representative single molecule $E_{PR}$-S histogram for T4 Lysozyme NTD M12 CTD A94-(GS)$_6$-SecM RNC (1×PBS 1 mM Mg(OAc)$_2$) tagged and labeled at M12.
Figure 55:
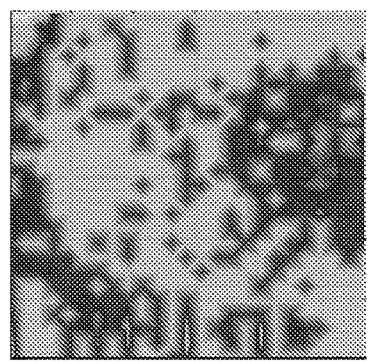
FIG. 55 depicts a representative single molecule $E_{PR}$-S histogram for T4 Lysozyme NTD M12-M53 EK-peptide-(GS)$_6$-SecM RNC (1×PBS 1 mM Mg(OAc)$_2$)tagged and labeled at M12-M53.

Highlights of these findings include the following. The $E_{PR}$ distributions of released dual-labeled constructs were all qualitatively consistent with their expected native structures. When folded and unfolded populations could be resolved along the $E_{PR}$ axis, mutations predicted to be destabilizing or stabilizing respectively shifted equilibria towards unfolded or folded sub-populations as expected (FIG. 26 and FIG. 27 illustrate the destabilizing effects L97A mutation and FIG. 28 and FIG. 26 illustrate stabilization imparted via C-terminal helical-peptide fusion in spectrin R16). Since RNCs and released proteins have a large difference in diffusion coefficients, the integrity of RNC samples used for smFRET analysis could also be verified using fluorescence correlation spectroscopy (see FIG. 29 to FIG. 32). Importantly, all (intact) RNC constructs yielded high-FRET populations qualitatively consistent with collapsed non-native nascent chain conformations for C-terminal PTC tethering lengths of up to 47 residues in general agreement with recent studies which explore nascent chain unfoldase activity of the ribosome.

Representative single molecule $E_{PR}$-S histograms for T4 Lysozyme, Barnase, Spectrin, and titin 128, e.g., as provided in FIGS. 4B-4F and FIG. 26-FIG. 55, display FRET efficiency ($E_{PR}$, horizontal axis) molecular stoichiometry (S, vertical axis) histograms acquired in approximately 5-15 minutes per sample (~20-100 pM labeled sample) in RNC buffer (unless otherwise noted) using the microscope system described. Tagged and labeled residues in each construct are indicated. FIG. 13 for more detailed information on each construct. Histograms were binned at 0.02 or 0.04 units between 0 and 1 and were colored according to the number of events detected and then converted to gray scale. Note that reported $E_{PR}$ values are intramolecular proximity ratios and are not corrected for leakage, direct excitation, or the instrumental γ-factor (assumed to be 1 for all datasets here). This results in some events having values outside the binned range. Note the absence of dual-labeled populations at intermediate S values for single-AUG programmed samples (indicating highly-specific UAA incorporation) and the presence of such populations in dual-AUG programmed samples (indicating complete labeling).

Sample Generation and Screening Strategies and Throughput

Figure 11:
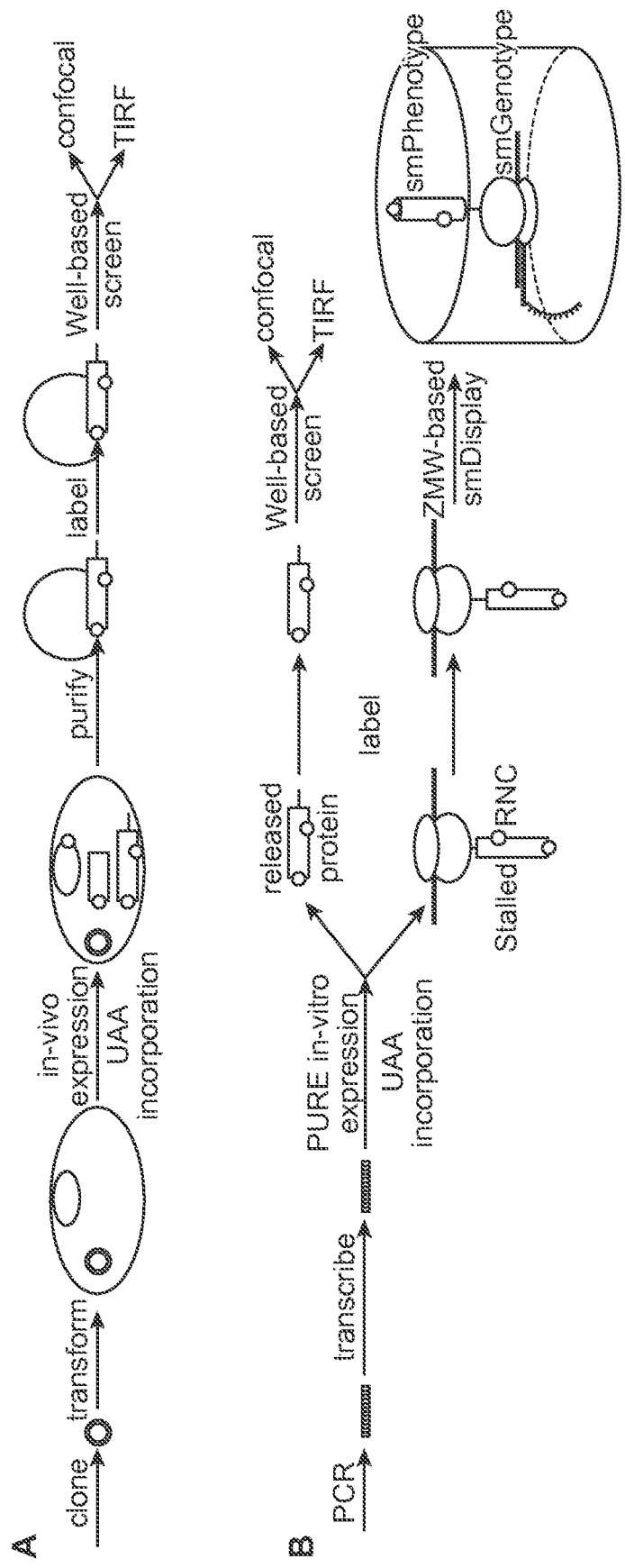
FIG. 11 provides a schematic comparison of in vivo (A) and in vitro (B) sample generation and screening strategies for single molecule FRET.

FIG. 11 provides a comparison of in-vivo (A) and in-vitro (B) tag-and-modify sample generation and screening strategies for single molecule FRET. In-vivo methods achieve site-specific UAA-incorporation and higher yields at the cost of lower throughputs imposed by traditional cloning and inefficient/non-specific suppression which necessitates protein purification. In contrast, in-vitro methods can potentially achieve higher throughputs using PCR-based cloning and robustly-quantitative and target-specific UAA-incorporation with suitable chemistries for labeling. While both approaches are ultimately limited by traditional (i.e. confocal or TIRF) single molecule screening throughputs, by generating dual-labeled RNCs and harnessing zero-mode-waveguides the in-vitro approach enables single-molecule co-localization of genotypes with phenotypes as well as multiplexed and highly parallelized single molecule screening.

Figure 15:
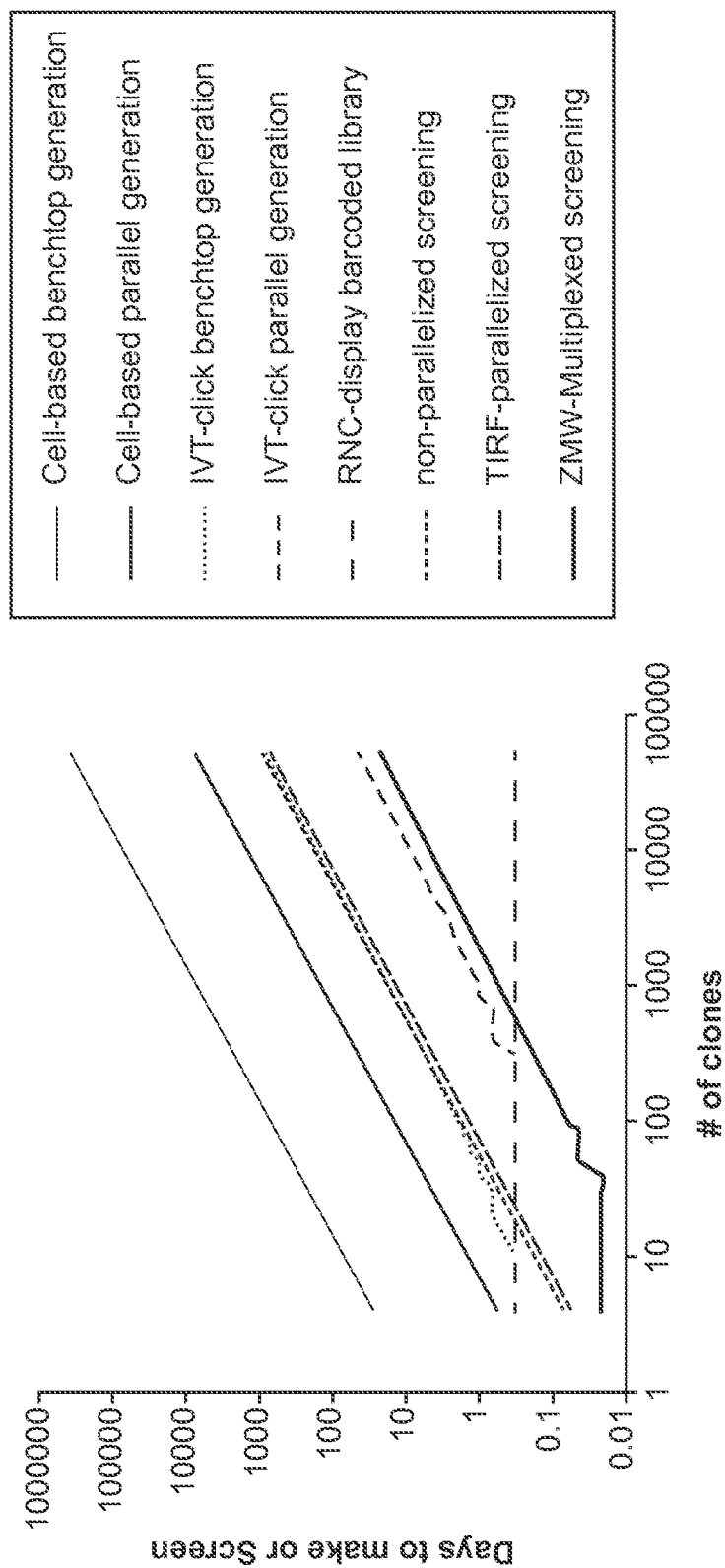
FIG. 15 depicts throughput calculations for sample generation and screening for various single-molecule phenotype approaches.
Figure 16:
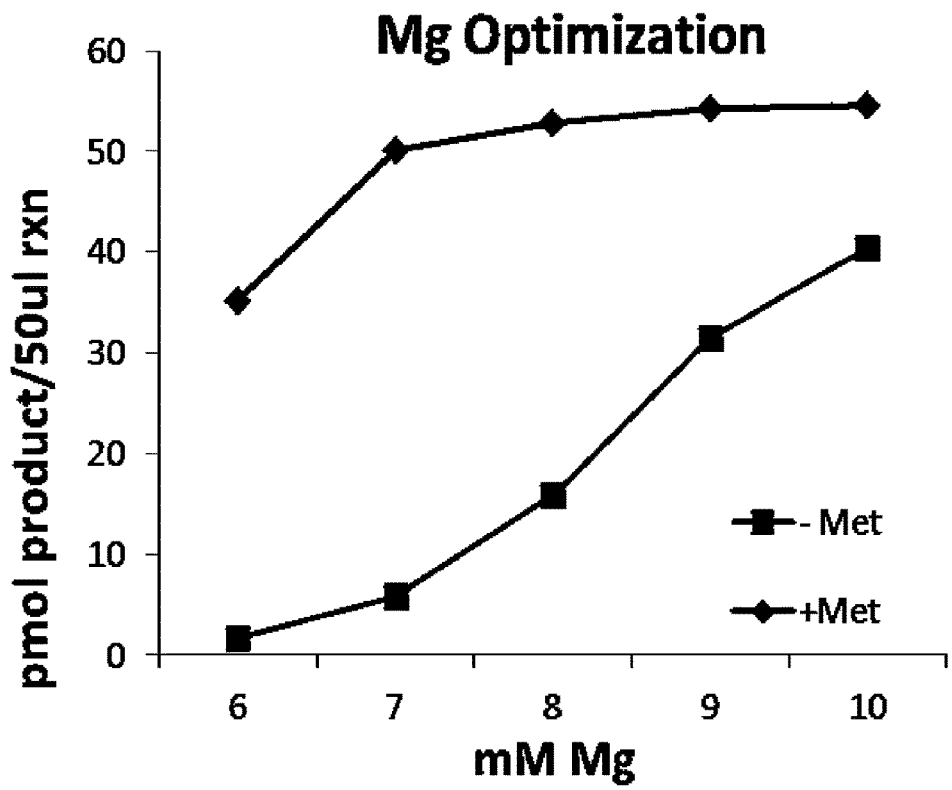
FIG. 16 depicts representative optimization of PURE-IVT pertaining to Mg concentration.
Figure 17:
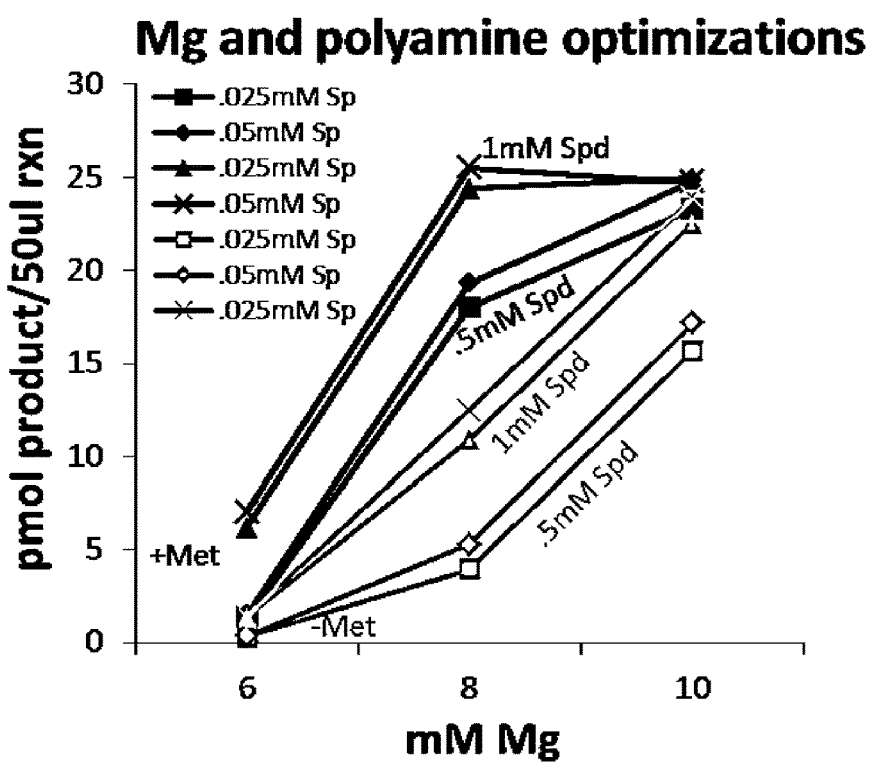
FIG. 17 depicts representative optimization of PURE-IVT pertaining to Mg and polyamine.

FIG. 15 provides throughput Calculations for sample generation and screening given as the number of days required to generate or screen a given number of clones/samples. The following assumptions were made for these calculations: 1). it takes roughly 7 days/clone for traditional cell-based benchtop sample generation methods (including plasmid-based cloning, sequencing, transformation, expression, purification, and labeling); 2). 48-fold parallelization is possible for the above steps; 3). 20 clones/8-hours can be produced using the benchtop in-vitro tag-and-modify sample generation methods present here (including PCR-based cloning, mRNA generation, PURE-IVT expression, and labeling); 4). 4×96-fold parallelization is possible for these in-vitro tag-and-modify steps; 5). generation of a dual-labeled RNC-display library of arbitrary size would take ~8 hours; 6). non-parallelized confocal screening rates of 2 molecules/second, 3000 molecules/ensemble, and no significant delay time between wells/clones; 7). parallelized TIRF-based screening at 300 molecules/field of view (FOV), 1 minute/FOV data acquisition, 3000 molecules/ensemble, and a 10 minute delay between wells or clones; and finally 8). 150000 molecules/FOV, 2 min/FOV, 3000 molecules/ensemble, and a 30 minute delay for binding/localization of molecules within each ZMW SMRT cell.

Elimination of Azide-Inactivation for Site-Specific Dual-Labeling

Figure 56:
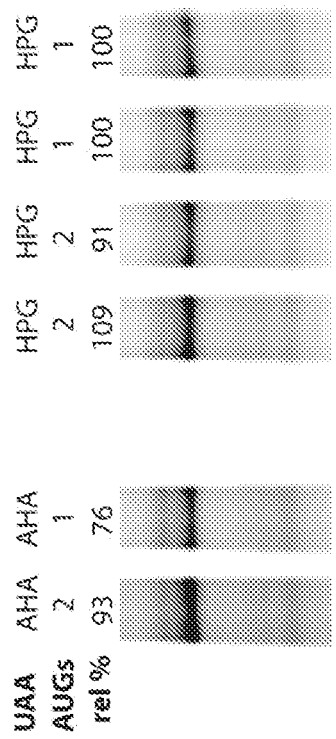
FIG. 56 shows that AHA can be maintained in a nearly completely reactive state if appropriate measures are taken to avoid and minimize inactivation.

We found that AHA is partially inactivated under the reducing conditions required for translation (FIGS. 16-25). Taking advantage of the developed fully-controllable PURE-IVT system translation and post-processing conditions were optimized to eliminate AHA-inactivation while maintaining high. This involved optimizing the concentration and type of reducing agent, the concentration of AHA, the pH of the translation reaction, protecting the translation reaction from ambient light, and quenching reducing agents with excess azide immediately following translation. Under these conditions HPG and AHA-tagged targets were both efficiently-labeled using BTTP/CuAAC (FIG. 56). Statistically-labeled AHA-tagged RNC products also exhibited significant dual-labeled FRET-active populations in $E_{PR}$-S histograms verifying this result.

Figure 57:
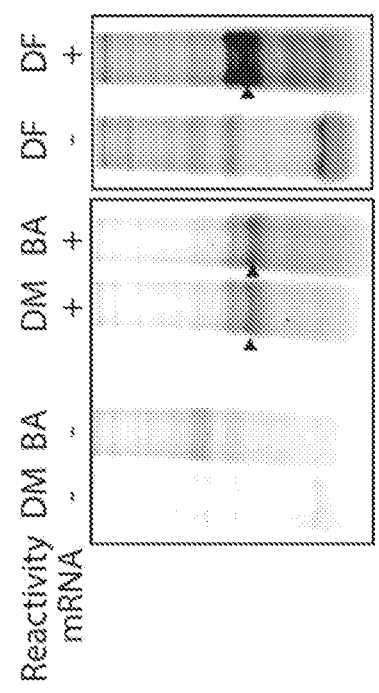
FIGS. 57-59 depict the consequences of measures taken to reduce background thiol-yne reactivity and enhance the sensitivity of SPAAC reagents as described herein.
Figure 59:
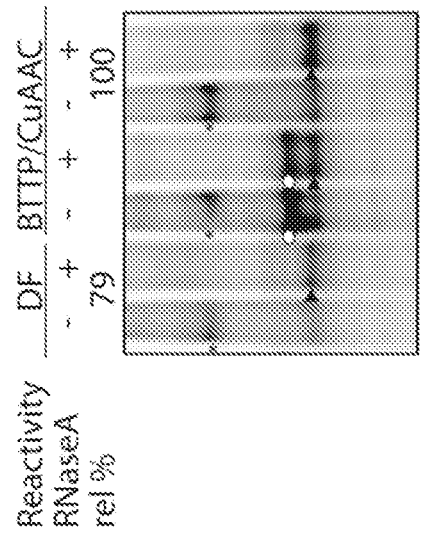

With the integrity of azide-tagged targets verified, background thiol-yne reactivity of copper-free SPAAC reagents was next minimized. Initially all SPAAC reagents tested exhibited prohibitively-high levels of background thiol-yne reactivity. This reactivity could be largely eliminated using thiol-capping reagents (FIGS. 56-57). However, in contrast to CuAAC reactions, residual AHA-dependent background levels remained in unpurified samples (FIG. 57, lanes 5-7). Sucrose cushions allowed simultaneous purification and concentration of AHA-tagged RNC targets away from other AHA-tagged translational components (e.g. AHA-tRNAs). Surprisingly it was found that such samples could be specifically and efficiently labeled at 2.5 μM concentrations using stoichiometric concentrations of thiol-yne-prone SPAAC reagents without resorting to thiol capping reagents (FIG. 59). This suggests a large and previously unappreciated rate-enhancement for SPAAC reactions in high-magnesium/ionic strength buffers.

Figure 18:
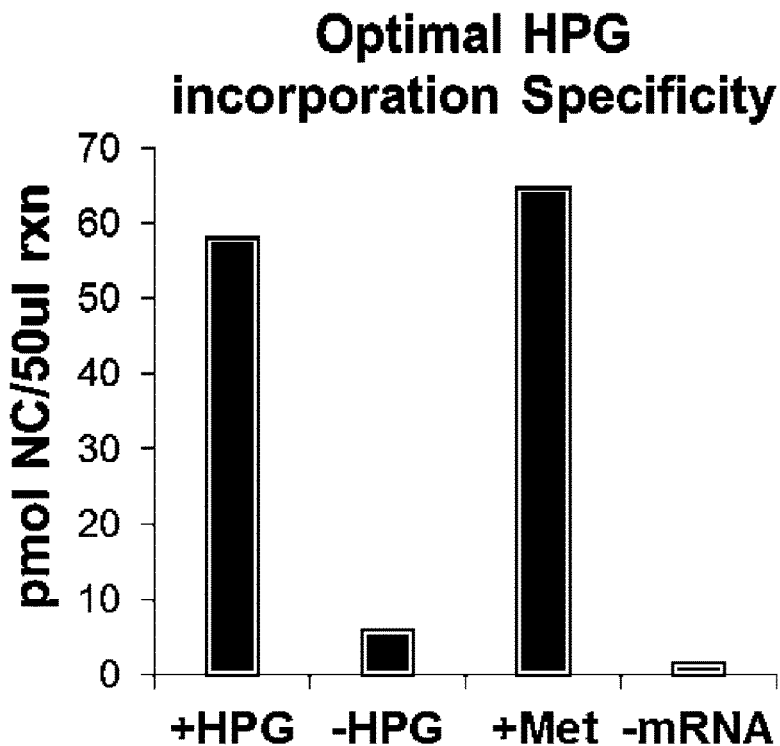
FIG. 18 depicts representative optimization of PURE-IVT pertaining to HPG incorporation specificity.
Figure 19:
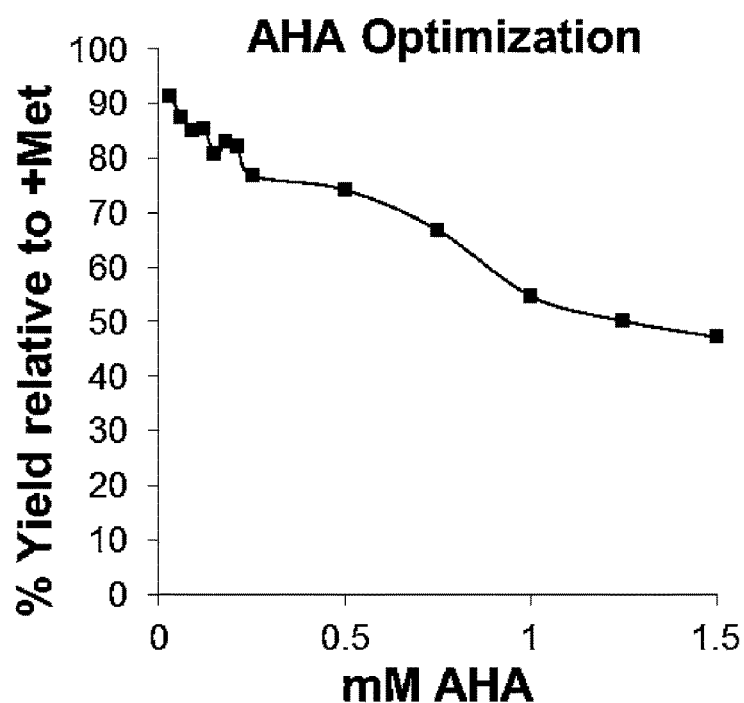
FIG. 19 depicts representative optimization of PURE-IVT pertaining to the relationship between yield and AHA concentration.

FIGS. 16-19 show representative PURE-IVT reaction condition optimizations. High-fidelity UAA-incorporation can be assured when product yields in the absence of methionine (−Met) are minimal whereas those in its presence (+Met) are maximized. The total NTP concentration was always 6 mM for these reactions thus the range of "free" magnesium tested in the panels was 0-4 mM. All mRNA templates have the same 5'-UTR sequence and only minor differences in the yields of different constructs was found under the different reaction conditions. The template used in the panel was T4 Lysozyme M1-M61-SecM. Final optimized conditions were: 8 mM Mg, 0.5 mM spermidine (Spd), 0 mM spermine (Sp), 0 mM putrescine, 2-5 μM Zn, 175 mM total monovalent ions ($NH_4^+ + K^+$), pH=7.6 (for HPG incorporations) and 7.0 (for AHA incorporations), 3 mM BME (for AHA incorporations) or 5 mM BME/DTT/Glutathione (for HPG incorporations). 50 μM HPG afforded high-yield and high-fidelity incorporation under these conditions (FIG. 18). In contrast, AHA levels above 30 μM significantly decreased yields (FIG. 19) most likely by reacting with the reducing agents required for translation.

FIG. 56 shows that AHA can be maintained in a nearly completely reactive state if appropriate measures are taken to avoid/minimize inactivation. BTTP/CuAAC labeling of AHA-tagged and HPG-tagged T4 Lysozyme RNCs with Atto647N-alkyne and Alexa647-azide, respectively. The pmols of dye conjugated to each RNC sample was calculated. The pmols of Atto647N-alkyne dye conjugated to AHA-tagged targets with a given number of AUGs was divided by the average pmols of Alexa647-azide dye conjugated to HPG-tagged targets with the same number of AUGs to obtain the relative % (rel %) values. Replicate labeling of the two different HPG constructs suggests a ±9% yield variability for all post-translational procedures. Since AHA-tagged targets were labeled with a brighter dye (Atto647N) than that used to label the HPG-tagged targets (Alexa647), the bands on the left of the figure below appear slightly brighter than those on the right even though they represent slightly lower amounts of actual dye.

Figure 58:
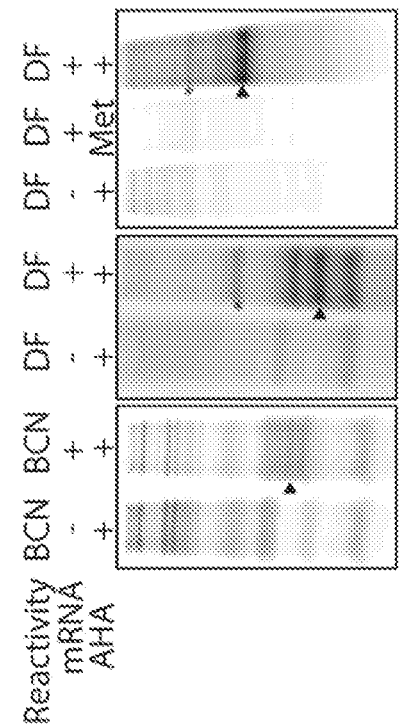

FIGS. 57-59 demonstrates reduced background thiol-yne reactivity and enhanced sensitivity of SPAAC reagents. Difluorinated cyclooctyne (DF), 6,7-dimethoxyazacyclooct-4-yne (DM), biarylazacyclooctynone (BA), and bicyclononyne (BCN) dye conjugates were added to unpurified, uncapped, AHA-tagged, and RnaseA/EDTA-treated RNCs (FIG. 57) or similarly processed but N-ethylmaleimide-capped intact RNCs (FIG. 58). Reactions carried out with AHA present during the translation reaction but without mRNA served as negative controls for global background levels. NEM-capping significantly reduced but did not eliminate background levels. An additional control reaction using methionine instead of AHA (second to last lane in FIG. 58) indicated that the remaining background sources are AHA-dependent (e.g. AHA-charged tRNAs). By purifying and concentrating AHA-tagged RNCs using a sucrose cushion and by using stoichiometric amounts of DIFO-dye conjugate, specific and efficient dye attachment could be achieved without resorting to thiol-capping reagents (FIG. 59). Conditions: FIG. 56). ~1 µM T4 Lysozyme AHA-RNCs in RNC buffer with 12 µM dye-conjugate, 15 hr labeling, RNaseA/EDTA treatment prior to analysis; FIG. 57). ~1 µM AHA-RNCs in RNC buffer with 2 µM dye conjugate, 48 hr labeling; FIG. 59). ~2.5 µM AHA-RNCs in RNC Buffer with 5 µM DIFO-Alexa647 (lanes 1,2), or already optimized BTTP/CuAAC labeling conditions (lanes 3-6), 16 hr labeling. An azide-inactivation control (○) is also shown (lanes 3-4).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A method of producing modified polypeptides suitable for structural and functional single molecule screening applications, the method comprising:
    carrying out in vitro cell-free translation of a polynucleotide in the presence of an unnatural amino acid and a plurality of natural amino acids,
    incorporating the unnatural amino acid and a plurality of natural amino acids at genetically-encoded positions in a target polypeptide, wherein incorporating comprises an incorporation efficiency, an incorporation specificity and a post-incorporation stability,
    generating between 5 and 500 picomoles of a target polypeptide comprising the unnatural amino acid and a plurality of natural amino acids incorporated at genetically-encoded target positions in the target polypeptide, wherein the unnatural amino acid comprises a reactive group, wherein the incorporation efficiency of the unnatural amino acid incorporation events at each of the genetically-encoded target positions in the target polypeptide is at least 91%, as compared to the efficiency of incorporating non-target natural amino acid or the efficiency of terminating translation via peptide releases, wherein the incorporation specificity of the unnatural amino-acid incorporation events for the particular genetically-encoded target positions in the target polypeptide is at least 91%, as compared to incorporation of the target unnatural amino acid into a non-target polypeptide or a non-target position in the target polypeptide, wherein the post-incorporation stability of the unnatural amino acid reactive group is at least about 91%, as compared to the level of inactivation of the reactive group; and wherein the combination such that when combined the incorporation efficiency, the incorporation specificity, and the post-incorporation stability renders target purification and concentration unnecessary for a purpose of achieving the labeling efficiencies and specificities required for single molecule screening applications; and
    modifying the reactive unnatural amino acid by cycloaddition of a heterologous moiety thereby producing a modified polypeptide comprising the heterologous moiety, wherein modifying is quantified using a labeling efficiency and a labeling specificity.

2. The method of claim 1, wherein the heterologous moiety comprises a fluorophore and is directly detectable using single molecule methods.

3. The method of claim 1, wherein the labeling efficiency is not less than 70% and the labeling specificity is not less than 90%.

4. The method of claim 1, wherein the reactive group is an azide-containing reactive group protected from undesirable inactivation under the reducing conditions required for translation such that post-incorporation stability remains greater than 90%.

5. The method of claim 1, wherein the reactive group is an azide-containing or an alkyne-containing reactive group and the cycloaddition is a ligand-assisted copper(I)-catalyzed azide-alkyne cycloaddition reaction.

6. The method of claim 1, wherein the reactive group is an azide-containing reactive group and the cycloaddition is a copper-free azide-alkyne cycloaddition reaction, wherein the heterologous moiety is protected from non-specific thiolyne side reactions.

7. The method of claim 5, wherein the ligand is selected from:
    bathophenanthrolinedisulfonate (BPS), tris-(hydroxyethyltriazolylmethyl)amine (THETA), tris-(hydroxypropyltriazolylmethyl)amine (THPTA), 2-[4-([bis([tert-butyltriazol-4-yl]methyl)-amino]methyl)-triazol-1-yl] ethyl sulfate (BTTES), or 344-([bis([tert-butyltriazol-4-yl]methyl)amino]methyl)-triazol-1-yl]propanol (BTTP).

8. The method of claim 1, wherein the unnatural amino acid is azidohomoalanine or homopropargylglycine.

9. The method of claim 1, further comprising producing a corresponding library of modified polypeptides, wherein the resulting library of modified polypeptides comprises:
    at least one modified polynucleotide-bound polypeptide comprising a monovalent genotype-phenotype linkage, wherein the linkage comprises either a stalled ribosome-bound nascent chain held together by a peptidyl-tRNA bond or a modified polypeptide-mRNA-complex held together by a puromycin moiety, wherein the cycloaddition modification does not disrupt the stability of the linkage, wherein all library members are simultaneously compatible with both single molecule direct sequencing of their polynucleotide components and single molecule phenotyping of their modified polypeptide components, and wherein the genotypes and phenotypes of each library member within a mixed library can be associated or registered by colocalized single molecule direct detection of the modified polynucleotide-bound polypeptide library members.

* * * * *

SEQUENCE LISTING

```
<160> NUMBER OF SEQ ID NOS: 3

<210> SEQ ID NO 1
<211> LENGTH: 189
<212> TYPE: PRT
<213> ORGANISM: Artificial Sequence
<220> FEATURE:
<223> OTHER INFORMATION: synthetic peptide sequence

<400> SEQUENCE: 1

Met Gly Ile Phe Glu Leu Leu Arg Ile Asp Glu Gly Leu Arg Leu Lys
1               5                   10                  15

Ile Tyr Lys Asp Thr Glu Gly Tyr Tyr Thr Ile Gly Ile Gly His Leu
            20                  25                  30

Leu Thr Lys Ser Pro Ser Leu Asn Ala Ala Lys Ser Glu Leu Asp Lys
        35                  40                  45

Ala Ile Gly Arg Asn Thr Asn Gly Val Ile Thr Lys Met Glu Ala Glu
    50                  55                  60

Lys Leu Phe Asn Gln Asp Val Asp Ala Ala Val Arg Gly Ile Leu Arg
65                  70                  75                  80

Asn Ala Lys Leu Lys Pro Val Tyr Asp Ser Leu Asp Ala Val Arg Arg
                85                  90                  95

Ala Ala Leu Ile Asn Leu Val Phe Gln Leu Gly Glu Thr Gly Val Ala
            100                 105                 110

Gly Phe Thr Asn Ser Leu Arg Leu Leu Gln Gln Lys Arg Trp Asp Glu
        115                 120                 125

Ala Ala Val Asn Leu Ala Lys Ser Arg Trp Tyr Asn Gln Thr Pro Asn
    130                 135                 140

Arg Ala Lys Arg Val Ile Thr Thr Phe Arg Thr Gly Thr Trp Cys Ala
145                 150                 155                 160

Tyr Lys Asn Leu Glu Phe Leu Pro Tyr Arg Gln Phe Ser Thr Pro Val
                165                 170                 175

Trp Ile Ser Gln Ala Gln Gly Ile Arg Ala Gly Pro Gln
            180                 185
```

```
<210> SEQ ID NO 2
<211> LENGTH: 18
<212> TYPE: PRT
<213> ORGANISM: Artificial Sequence
<220> FEATURE:
<223> OTHER INFORMATION: synthetic peptide sequence

<400> SEQUENCE: 2

Phe Ser Thr Pro Val Trp Ile Ser Gln Ala Gln Gly Ile Arg Ala Gly
1               5                   10                  15

Pro Gln

<210> SEQ ID NO 3
<211> LENGTH: 21
<212> TYPE: RNA
<213> ORGANISM: Artificial Sequence
<220> FEATURE:
<223> OTHER INFORMATION: synthetic polynucleotide sequence

<400> SEQUENCE: 3
gggagaccac aacgguuucc c                                                     21
```